(12) United States Patent
Chory et al.

(10) Patent No.: US 11,267,809 B2
(45) Date of Patent: Mar. 8, 2022

(54) BAF COMPLEX MODULATING COMPOUNDS AND METHODS OF USING THE SAME

(71) Applicant: THE BOARD OF TRUSTEES OF THE LELAND STANFORD JUNIOR UNIVERSITY, Stanford, CA (US)

(72) Inventors: Emma J. Chory, Menlo Park, CA (US); Gerald R. Crabtree, Woodside, CA (US); Emily C. Dykhuizen, West Lafayette, IN (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 16/635,542

(22) PCT Filed: Sep. 13, 2018

(86) PCT No.: PCT/US2018/050888
§ 371 (c)(1),
(2) Date: Jan. 30, 2020

(87) PCT Pub. No.: WO2019/055657
PCT Pub. Date: Mar. 21, 2019

(65) Prior Publication Data
US 2020/0255416 A1    Aug. 13, 2020

Related U.S. Application Data

(60) Provisional application No. 62/697,033, filed on Jul. 12, 2018, provisional application No. 62/558,784, filed on Sep. 14, 2017.

(51) Int. Cl.
| | | |
|---|---|---|
| C07D 413/14 | (2006.01) | |
| C07D 273/02 | (2006.01) | |
| C07D 413/10 | (2006.01) | |

(52) U.S. Cl.
CPC ......... *C07D 413/14* (2013.01); *C07D 273/02* (2013.01); *C07D 413/10* (2013.01)

(58) Field of Classification Search
CPC ... C07D 413/14; C07D 273/02; C07D 413/10
See application file for complete search history.

(56) References Cited

U.S. PATENT DOCUMENTS

| | | |
|---|---|---|
| 9,410,943 B2 | 8/2016 | Kadoch et al. |
| 9,663,535 B2 | 5/2017 | Breslin et al. |
| 2012/0202821 A1 | 8/2012 | Obrecht et al. |
| 2015/0246907 A1 | 9/2015 | Altmann et al. |
| 2021/0315876 A1* | 10/2021 | Dykhuizen ........... A61K 31/395 |

FOREIGN PATENT DOCUMENTS

WO    WO200177113 A2    6/2002

OTHER PUBLICATIONS

National Center for Biotechnology Information. PubChem Substance Record for SID 131428141, BRD-K69367836-001-01-4, Source: Broad Institute, https://pubchem.ncbi.nlm.nih.gov/substance/131428141. Date Available: Dec. 20, 2011. (Year: 2011).*
National Center for Biotechnology Information. PubChem Substance Record for SID 172131385, BRD-K51299478-001-01-2, Source: Broad Institute, https://pubchem.ncbi.nlm.nih.gov/substance/172131385. Date Available: Feb. 7, 2015. (Year: 2015).*
National Center for Biotechnology Information. PubChem Substance Record for SID 131429945, BRD-K98645985-001-01-7, Source: Broad Institute, https://pubchem.ncbi.nlm.nih.gov/substance/131429945. Date Available: Dec. 20, 2011. (Year: 2011).*
Hohmann; Trends in Genetics 2014, 30(8), 356-363. https://doi.org/10.1016/j.tig.2014.05.001 (Year: 2014).*
Marian; Cell Chemical Biology 2018, 25, 1443-1455. https://doi.org/10.1016/j.chembiol.2018.08.004 (Year: 2018).*
Weber; Pharmacology & Therapeutics 2015, 149, 124-138. http://dx.doi.org/10.1016/j.pharmthera.2014.12.001 (Year: 2015).*
Arasappan, et al."Novel Dipeptide Macrocycles from 4-Oxo, -Thio, and -Amino-Substituted Proline Derivatives",: J. Org. Chem. 2002, 67, 11, 3923-3926.
Fitzgerald, et al. "Build/Couple/Pair Strategy for the Synthesis of Stereochemically Diverse Macrolactams via Head-to-Tail Cyclization", American Chemical Society, 2012, 14, 89-96.
Fitzgerald, et al. "A Build/Couple/Pair Strategy for the Synthesis of Stereochemically Diverse Macrolactams via Head-to-Tail Cyclization", A. J. Org. Chem. 1997, 62, 7512-7515.
Marsault, et al."Potent Macrocyclic Antagonists to the Motilin Receptor Presenting Novel Unnatural Amino Acids", Bioorg Med Chem Lett. Aug. 1, 2007;17(15):4187-90.
Over, et al "Structural and conformational determinants of macrocycle cell permeability", Nature Chemical Biology 12, 1065-1074 (2016).
Shirakawa, et al. "Reactivation of latent HIV by histone deacetylase inhibitors", Trends Microbiol. Jun. 2013 ; 21(6): 277-285.
Son, et al. "The role of BAF (mSWI/SNF) complexes in mammalian neural development", Am J Med Genet C Semin Med Genet. Sep. 2014 ; 0(3): 333-349.
Hill, et al. "Predicting the outcomes of treatment to eradicate the latent reservoir for HIV-1", PNAS Sep. 16, 2014. 111 (37) 13475-13480.

* cited by examiner

*Primary Examiner* — Daniel R Carcanague
(74) *Attorney, Agent, or Firm* — Bret E. Field; Bozicevic, Field & Francis LLP

(57) ABSTRACT

The invention provided here creates a new paradigm for the treatment of a variety of conditions where modulation of a BAF complex is desired. The disclosure that follows outlines a strategy for modulating a BAF complex in a cell, and provides effective compounds, pharmaceutical compositions, development strategies, and treatment protocols, and describes many of the ensuing benefits. A new family of BAF complex modulating compounds has been developed based on a new chemical scaffold including a 12-membered macrolactam core structures. Contacting target cells in vitro or in vivo with the compounds and compositions of this invention can selectively inhibit the activity of BAF complexes in such cells. Some of the BAF complex modulating compounds in this family are particularly effective agents for treating cancer in conjunction with a ATR inhibitor.

9 Claims, 23 Drawing Sheets

Specification includes a Sequence Listing.

Baficillin1

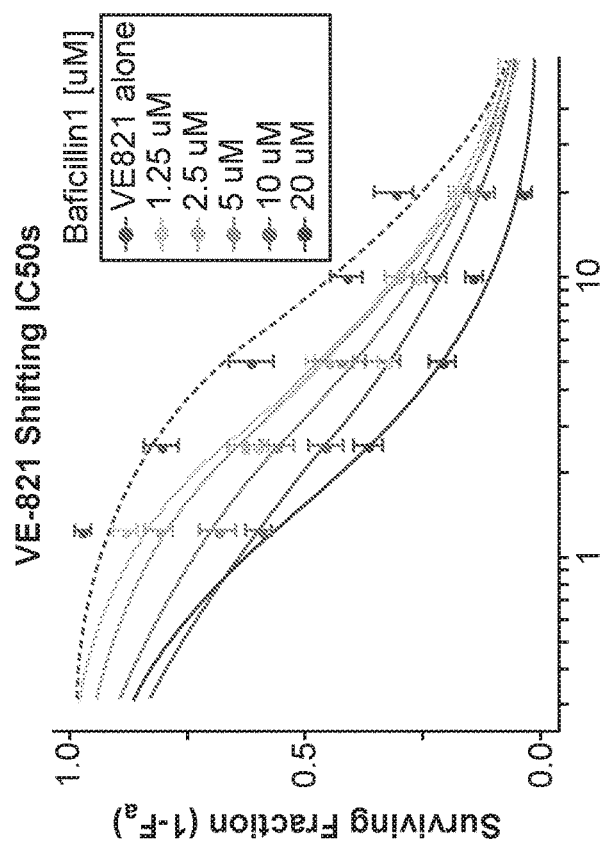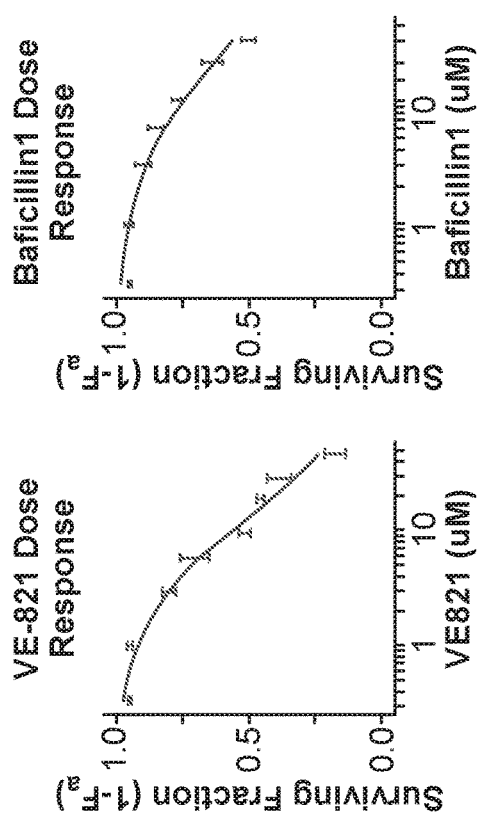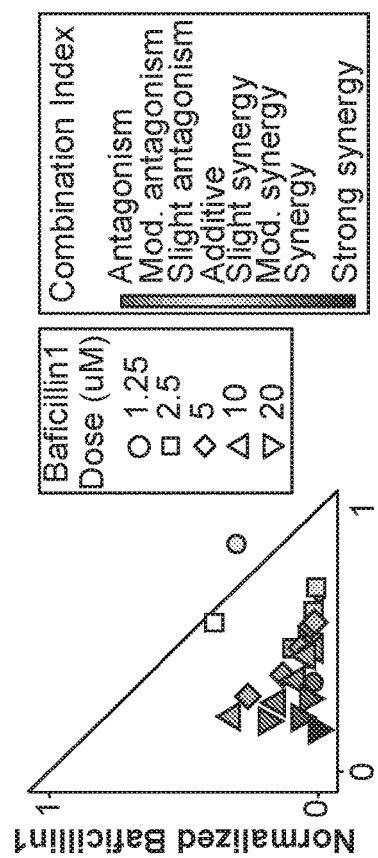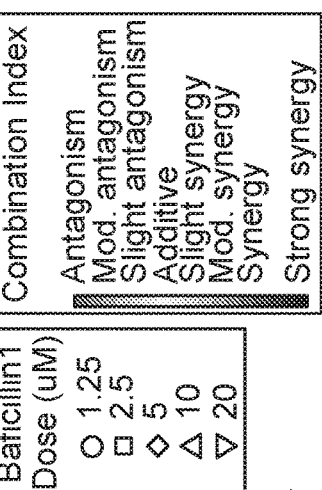
FIG. 2A  FIG. 2B  FIG. 2C

BAF COMPLEX MODULATING COMPOUNDS AND METHODS OF USING THE SAME

CROSS REFERENCE

This application claims the benefit of U.S. Provisional Application No. 62/697,033, filed Jul. 12, 2018, and U.S. Provisional Application No. 62/558,784, filed Sep. 14, 2017, which applications are incorporated herein by reference.

GOVERNMENT RIGHTS

This invention was made with Government support under contract DA032469 awarded by the National Institutes of Health. The Government has certain rights in the invention.

FIELD OF THE INVENTION

The technology disclosed and claimed below relates generally to the field of BAF complex modulation. In particular, this disclosure provides a new scaffold for chemical structures that inhibit BAF complexes.

SUMMARY

The invention provided here creates a new paradigm for the treatment of a variety of conditions where modulation of a BAF complex is desired. The disclosure that follows outlines a strategy for modulating BAF complex in a cell, and provides effective compounds, pharmaceutical compositions, development strategies, and treatment protocols, and describes many of the ensuing benefits.

A new family of BAF complex modulating compounds has been developed based on a new chemical scaffold. Contacting target cells in vitro or in vivo with the compounds and compositions of this invention can selectively inhibit the activity of BAF complexes in such cells. The inhibitors can be used for administration to a target tissue or cell in a subject having a condition associated with a BAF complex or in which targeting a BAF complex is of interest, thereby selectively modulating (e.g., inhibiting) formation of a BAF complex in target cells in or around the tissue and relieving one or more symptoms or signs of the conditions. Some of the BAF complex modulating compounds in this family are particularly effective agents for treating cancer in conjunction with a ATR inhibitor.

The invention is put forth in the description that follows, in the figures, and in the appended claims.

DRAWINGS

Figure 1B:
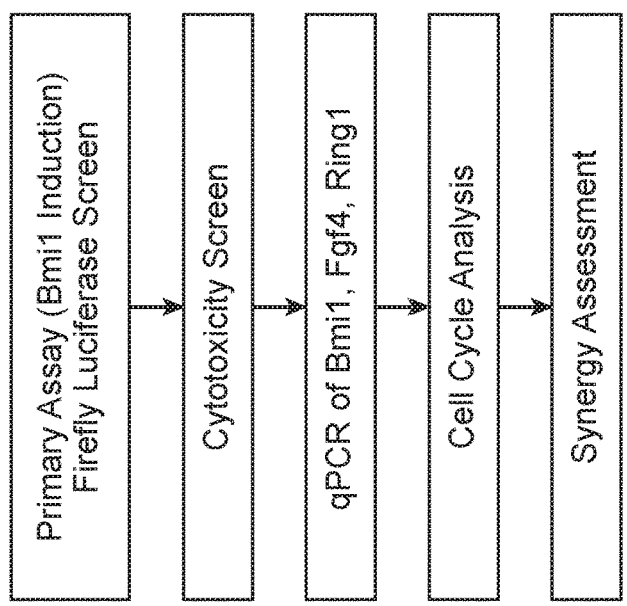
FIG. 1 illustrates a strategy for assessing hyper-synthetic lethality of combination BAFi and ATRi.

Further details of these drawings are provided in the experimental section below.

DETAILED DESCRIPTION

Modulation of BAF complexes

Human SWI/SNF (BAF) complexes are a diverse family of ATP-dependent chromatin remodelers that exhibit combinatorial specificity to regulate specific genetic programs. BAF complexes regulate transcription, replication and DNA repair through a variety of mechanisms.

The technology described and claimed below represents the first description of a new class of BAF complex modulating compounds that can be used to inhibit the functions of mammalian BAF complexes for purposes of modulating various targets, e.g., modulating genetic targets whose expression is associated with the BAF complex.

It has now been discovered that compounds based on the new scaffold described herein can provide strong BAF complex inhibition and upregulate target genes repressed by embryonic BAF complex (esBAF). These compounds can be developed as highly potent and specific cancer therapeutics having synergistic hyper-synthetic-lethality with ATR inhibitors, as described in the sections that follow.

BAF Complex Modulating Compounds

This invention includes BAF complex modulating compounds having a scaffold based on a 12-membered macrolactam that can provide for potent BAF complex inhibition. Exemplary compounds including 12-membered macrolactam core structures are described in the following formulae I-III and structures 1-10.

As such, the invention can be practiced with a BAF modulating compound of formula (I):

(I)

wherein:

$R^1$ is amine, substituted amine, alkylaminocarbonylamino, substituted alkylaminocarbonylamino, alkanoylamino, substituted alkanoylamino, arylaminocarbonylamino, substituted arylaminocarbonlamino, carbamate, substituted carbamate, aroylamino or substituted aroylamino;

R² is a heteroaryl-aryl-alkyl, substituted heteroaryl-arylalkyl, aryl-heteroaryl-alkyl, substituted aryl-heteroaryl alkyl, alkanoyl or substituted alkanoyl;

R³ to R⁶ are each independently H, alkyl or substituted alkyl;

or a pharmaceutically acceptable salt thereof.

It will be understood that unless indicated otherwise, in any BAF modulating compound described herein having one or more chiral centers, if an absolute stereochemistry is not expressly indicated, then each center may independently be of R-configuration or S-configuration or a mixture thereof. In certain embodiments of formula (I), the stereochemistry at C2, C5 and C6 is configured to provide the S, S, R stereoisomer at C2, C5 and C6 respectively. In other embodiments, the stereochemistry of the compound of formula (I) is configured to provide the R, S, R stereoisomer at C2, C5 and C6 respectively.

In some cases, the subject BAF modulating compound is of the formula (IA):

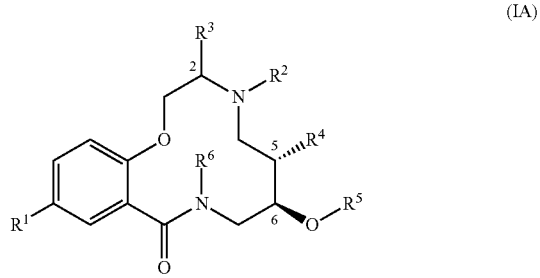

(IA)

wherein:

R¹ is amine, substituted amine, alkylaminocarbonylamino, substituted alkylaminocarbonylamino, alkanoylamino, substituted alkanoylamino, arylaminocarbonylamino, substituted arylaminocarbonlamino, carbamate, substituted carbamate, aroylamino or substituted aroylamino;

R² is a heteroaryl-aryl-alkyl, substituted heteroaryl-arylalkyl, aryl-heteroaryl-alkyl, substituted aryl-heteroaryl alkyl, alkanoyl or substituted alkanoyl;

R³ to R⁶ are each independently H, alkyl or substituted alkyl; or a pharmaceutically acceptable salt thereof.

In certain embodiments the compound of formula (IA), the stereochemistry at C2 is configured to provide the S, S, R stereoisomer at C2, C5 and C6 respectively. In other embodiments, the stereochemistry of the compound of formula (IA) is configured to provide the R, S, R stereoisomer at C2, C5 and C6 respectively.

In some cases, the subject BAF modulating compound is of the formula (IB):

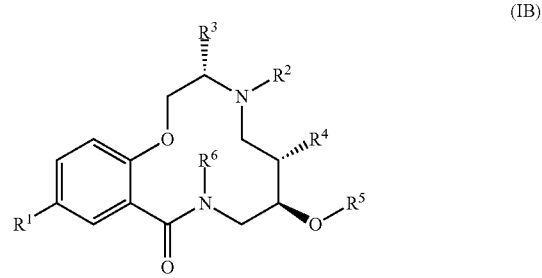

(IB)

wherein:

R¹ is amine, substituted amine, alkylaminocarbonylamino, substituted alkylaminocarbonylamino, alkanoylamino, substituted alkanoylamino, arylaminocarbonylamino, substituted arylaminocarbonlamino, carbamate, substituted carbamate, aroylamino or substituted aroylamino;

R² is a heteroaryl-aryl-alkyl, substituted heteroaryl-arylalkyl, aryl-heteroaryl-alkyl, substituted aryl-heteroaryl alkyl, alkanoyl or substituted alkanoyl;

R³ to R⁶ are each independently H, alkyl or substituted alkyl; or a pharmaceutically acceptable salt thereof.

In some embodiments of any of formulae (I) to (IB), R¹ is an alkylaminocarbonylamino. Particular examples of alkylaminocarbonylamino groups include, but are not limited to isopropyl-NHCONH— and propyl-NHCONH. In other cases, R¹ is an arylaminocarbonylamino group. A particular example of an arylaminocarbonylamino group includes, but is not limited to phenyl-NHCONH—. In some cases, R¹ is an amine. Particular example of amines include, but are not limited to —NH2 and pyrimidine-NH—. In some cases, R¹ is a carbamate. A particular example of a carbamate includes, but is not limited to isopropyl-OCONH—. In some cases, R¹ is an alkanoylamino. Particular exmaples of alkanoylamino groups include, but are not limited to isopropyl-CONH— and propyl-CONH—. In some other cases, R¹ is an aroylamino. A particular example of an aroylamino group includes, but is not limited to phenyl-CONH—. It will be understood that any of the R¹ groups disclosed herein may be optionally substituted, e.g., with a substituent as described herein.

In some embodiments of any of formulae (I) to (TB), R¹ is selected from:

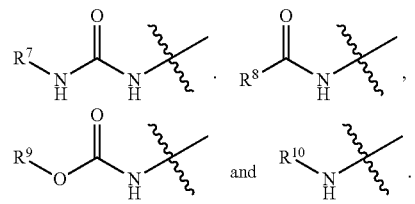

In some cases, R⁷, R⁸ and R⁹ are each independently selected from, alkyl, substituted alkyl, aryl, substituted aryl, heteroaryl, substituted heteroaryl, cycloalkyl, substituted cycloalkyl, heterocycle, substituted heterocycle; and R¹⁰ is substituted H, alkyl, substituted alkyl, aryl, subsitututed aryl, heteroaryl, substituted heteroaryl, cycloalkyl, substituted cycloalkyl, heterocycle and substituted heterocycle.

In certain cases, R⁷ is alkyl or substituted alkyl. In some cases R⁷ is methyl, ethyl, propyl, isopropyl, butyl, sec-butyl, tert-butyl, pentyl, hexyl. In some cases, R⁷ is an aryl or a substituted aryl group. In some cases R⁷ is phenyl or substituted phenyl. In some cases R⁷ is heteroaryl or substituted heteroaryl. In some cases, R⁷ is cycloalkyl or substituted cycloalkyl. In certain cases, R⁷ is a heterocycle or substituted heterocycle.

In certain cases, R⁸ is alkyl or substituted alkyl. In some cases R⁸ is methyl, ethyl, propyl, isopropyl, butyl, sec-butyl, tert-butyl, pentyl, hexyl. In some cases, R⁸ is an aryl or a substituted aryl group. In some cases R⁸ is phenyl or substituted phenyl. In some cases R⁸ is heteroaryl or substituted heteroaryl. In some cases, R⁸ is cycloalkyl or substituted cycloalkyl. In certain cases, R⁸ is a heterocycle or substituted heterocycle.

In certain cases, R⁹ is alkyl or substituted alkyl. In some cases R⁹ is methyl, ethyl, propyl, isopropyl, butyl, sec-butyl, tert-butyl, pentyl, hexyl. In some cases, R⁹ is an aryl or a substituted aryl group. In some cases R⁹ is phenyl or substituted phenyl. In some cases, R⁹ is heteroaryl or substituted heteroaryl. In some cases, R⁹ is cycloalkyl or substituted cycloalkyl. In certain cases, R⁹ is a heterocycle or substituted heterocycle.

In some cases, R¹⁰ is H. In certain cases, R¹⁰ is alkyl or substituted alkyl. In some cases R¹⁰ is methyl, ethyl, propyl, isopropyl, butyl, sec-butyl, tert-butyl, pentyl, hexyl. In some cases, R¹⁰ is an aryl or a substituted aryl group. In some cases R¹⁰ is phenyl or substituted phenyl. In some cases R¹⁰ is heteroaryl or substituted heteroaryl. In some cases, R¹⁰ is cycloalkyl or substituted cycloalkyl. In certain cases, R¹⁰ is a heterocycle or substituted heterocycle. In some cases R¹⁰ is a nitrogen containing heteroaryl, e.g., pyridine, pyrimidine, pyridazine, pyrazine, triazine. In certain cases, R¹⁰ is pyrimidine.

In some embodiments of any of formulae (I) to (IB) R¹ is selected from:

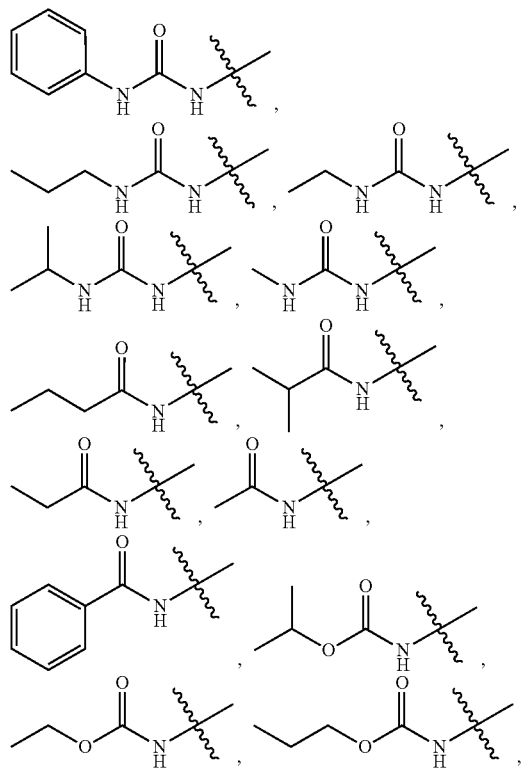

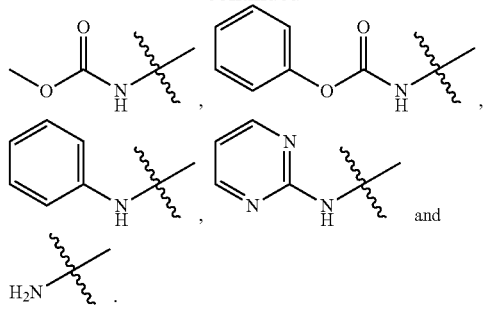

In certain cases of any of formulae (I) to (IB), R¹ is selected from:

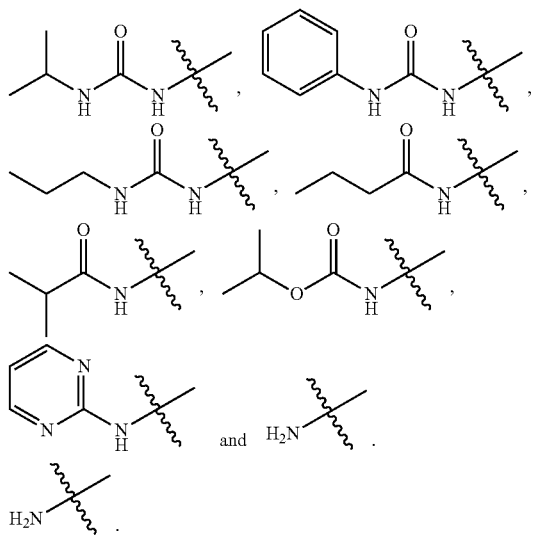

In some embodiments of any of formulae (I) to (IB), R² is heteroaryl-aryl-alkyl. Particular examples of heteroaryl-aryl-alkyl include, but are not limited to, 4-(pyridin-2-yl)-benzyl, 4-(pyridin-3-yl)-benzyl and 4-(pyridine-4-yl)-benzyl. In some cases, R² is aryl-heteroaryl-alkyl. In some cases, R² is alkanoyl. A particular example of an alkanoyl includes, but is not limited to cyclopropyl-acetyl. In will be understood that any of the R² groups disclosed herein may be optionally substituted, e.g., with a substituent as described herein.

In some embodiments of any of formulae (I) to (IB), R² is of the formula:

-L¹-Z (IC); or

-L²—C(O)-L³-R¹¹ (ID)

wherein, L¹ is an alkyl linker or a substituted alkyl linker; L² and L³ are each independently selected from a covalent bond, an alkyl linker and a substituted alkyl linker; Z is heteroaryl-aryl, substituted heteroaryl-aryl, aryl-heteroaryl or substituted heteroaryl-aryl; and R¹¹ is alkyl, substituted alkyl, $C_{3-10}$ cycloalkyl, substituted $C_{3-10}$ cycloalkyl, $C_{3-10}$ heterocycle or substituted $C_{3-10}$ heterocycle.

In some cases, any of L¹, L² or L³ is a $(C_1-C_{12})$alkyl linker, which may be straight or branched, e.g., methyl, ethyl, n-propyl, 1-methylethyl (iso-propyl), n-butyl, n-pentyl, 1,1-dimethylethyl (t-butyl), and the like. In some cases L¹ is methyl. In some cases L² is a covalent bond. In some cases L³ is methyl.

In some embodiments, the $R^2$ group of formula (IC), has the formula (IE):

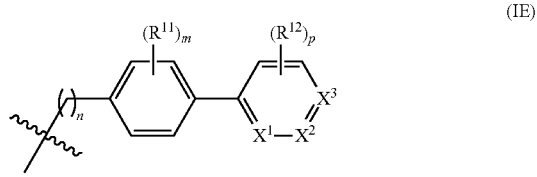

(IE)

wherein:
two of $X^1$, $X^2$ and $X^3$ are carbon atoms and one of $X^1$, $X^2$ and $X^3$ is a nitrogen atom;
$R^{11}$ and $R^{12}$ are independently selected from OH, alkyl, substituted alkyl, alkenyl, substituted alkenyl, aryl, substituted aryl, alkoxy, substituted alkoxy, —OCF$_3$, —CF3, halogen, azide, amine, substituted amine, amide, cycloalkyl, substituted cycloalkyl, heterocycle and substituted heterocycle;
n is an integer from 1 to 12;
m is an integer from 0 to 4; and
p is an integer from 0 to 5.

In some cases of formula (IE), $X^1$ is a nitrogen atom, $X^2$ and $X^3$ are carbon atoms, n is 1, m is 0 and p is 0. In other cases of formula (IE), $X^2$ is a nitrogen atom, $X^1$ and $X^3$ are carbon atoms, n is 1, m is 0 and p is 0. In other cases of formula (IE), $X^3$ is a nitrogen atom, $X^1$ and $X^2$ are carbon atoms, n is 1, m is 0 and p is 0.

In some embodiments, the $R^2$ group of formula (ID), has a formula of any of (IF 1)-(IF4):

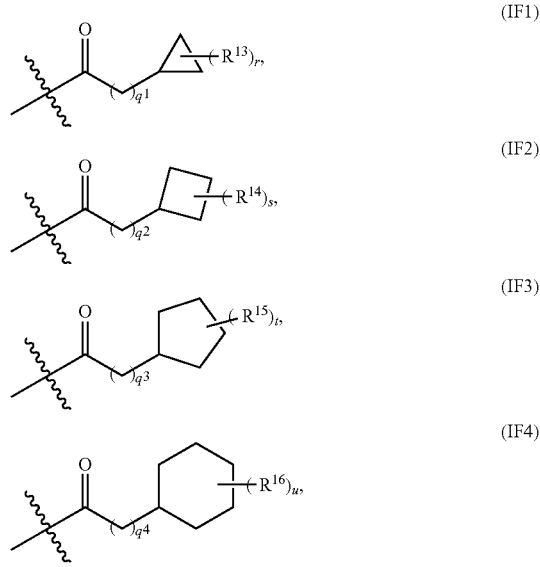

wherein:
$R^{13}$, $R^{14}$, $R^{15}$ and $R^{16}$ are independently selected from OH, alkyl, substituted alkyl, alkenyl, substituted alkenyl, aryl, substituted aryl, alkoxy, substituted alkoxy, —OCF$_3$, —CF$_3$, halogen, azide, amine, substituted amine, amide, cycloalkyl, substituted cycloalkyl, heterocycle and substituted heterocycle;

$q^1$ to $q^4$ are each independently an integer from 0 to 12;
r is an integer from 0 to 5;
s is an integer from 0 to 7;
t is an integer from 0 to 9; and
u is an integer from 0 to 11.

In some cases the $R^2$ group of formula (ID) is of the formula (IF1). In some instances of formula (IF1), q1 is 1 and r is 0.

In some embodiments of any of formulae (I) to (ID), $R^2$ is selected from:

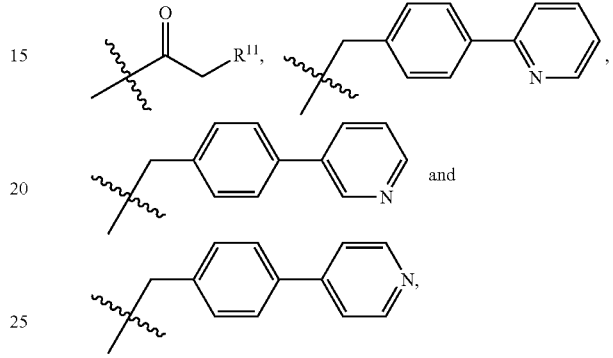

wherein $R^{11}$ is alkyl, substituted alkyl, $C_{3-10}$ cycloalkyl, substituted $C_{3-10}$ cycloalkyl, $C_{3-10}$ heterocycle or substituted $C_{3-10}$ heterocycle. In certain embodiments, $R^{11}$ is a lower alkyl, e.g., methyl, ethyl, propyl, isopropyl, butyl, sec-butyl, tert-butyl, pentyl or hexyl. In other embodiments, $R^{11}$ is selected from $C_{3-10}$ cycloalkyl, e.g., cyclopropyl, cyclobutyl, cyclopentyl, cyclohexyl, cycloheptyl, cyclooctyl. In some cases, $R^{11}$ is a cyclopropyl group.

In some cases of any of formulae (I) to (IB), $R^2$ is:

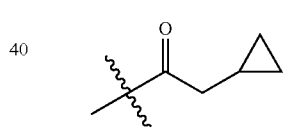

In some cases of any of formulae (I) to (IB), $R^2$ is:

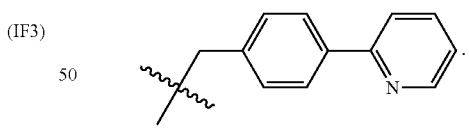

In some embodiments of any of formulae (I) to (TB), each of $R^3$ to $R^6$ is a lower alkyl group selected from methyl, ethyl, n-propyl, isopropyl, n-butyl, isobutyl, t-butyl, pentyl and hexyl. In some embodiments of any of formulae (I) to (TB) $R^3$ is methyl. In some embodiments of any of formulae (I) to (TB) $R^4$ is methyl. In some embodiments of any of formulae (I) to (TB) $R^5$ is methyl. In some embodiments of any of formulae (I) to (TB) $R^6$ is methyl. In some embodiments of any of formulae (I) to (TB) at least two of $R^3$ to $R^6$ is methyl. In some embodiments of any of formulae (I) to (TB) at least three of $R^3$ to $R^6$ is methyl. In some embodiments, each of $R^3$, $R^4$, $R^5$ and $R^6$ are methyl groups.

In some embodiments of any of formulae (I) to (TB), the structure has the formula (II):

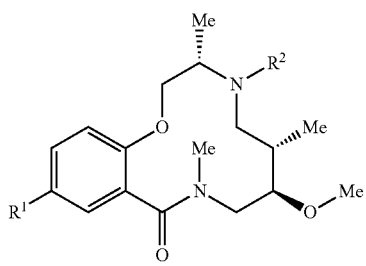

wherein:

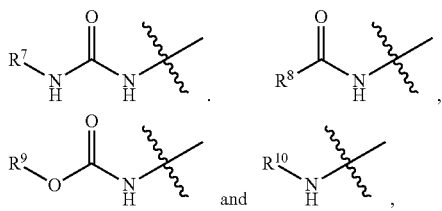

$R^1$ is wherein $R^7$, $R^8$ and $R^9$ are each independently selected from, methyl, ethyl, propyl, isopropyl, butyl, sec-butyl, tert-butyl, pentyl, hexyl, aryl, substituted aryl, heteroaryl, substituted heteroaryl, cycloalkyl, substituted cycloalkyl, heterocycle, substituted heterocycle; and $R^{10}$ is selected from H, alkyl, substituted alkyl, aryl, substituted aryl, heteroaryl, substituted heteroaryl, cycloalkyl, substituted cycloalkyl, heterocycle and substituted heterocycle; and $R^2$ is selected from

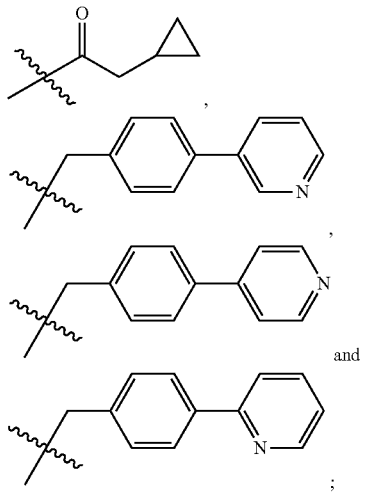

or a pharmaceutically acceptable salt thereof.

In some cases of formula (II), $R^2$ is:

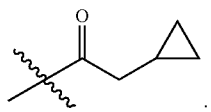 [SMILES: *C(=O)CC1CC1]

In some cases of formula (II), $R^2$ is:

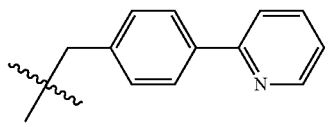

In some embodiments of formula (II), the structure has the formula (III):

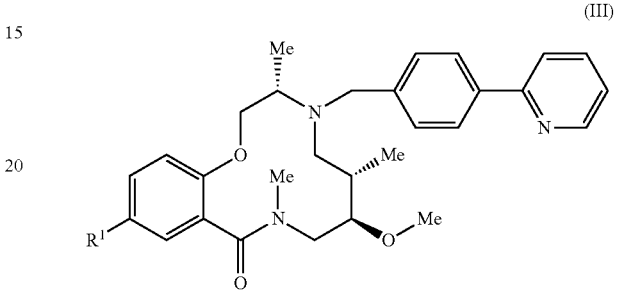

wherein:
$R^1$ is

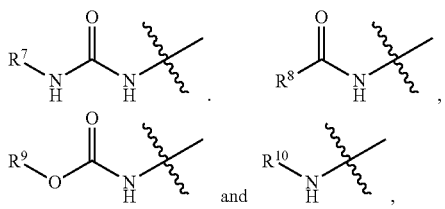

wherein:
$R^7$, $R^8$ and $R^9$ are each independently selected from, methyl, ethyl, propyl, isopropyl, butyl, sec-butyl, tert-butyl, pentyl, hexyl, aryl, substituted aryl, heteroaryl, substituted heteroaryl, cycloalkyl, substituted cycloalkyl, heterocycle, substituted heterocycle;
or a pharmaceutically acceptable salt thereof.

In some embodiments of formulae (II) or (III), $R^1$ is selected from:

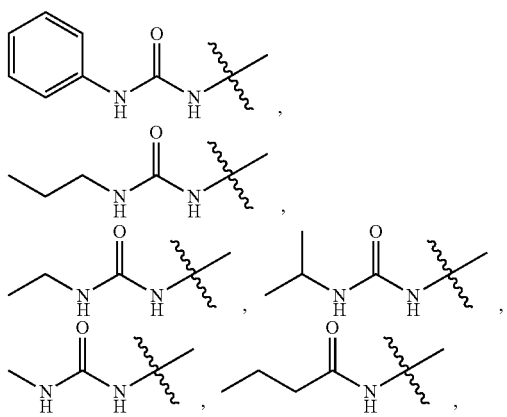

-continued
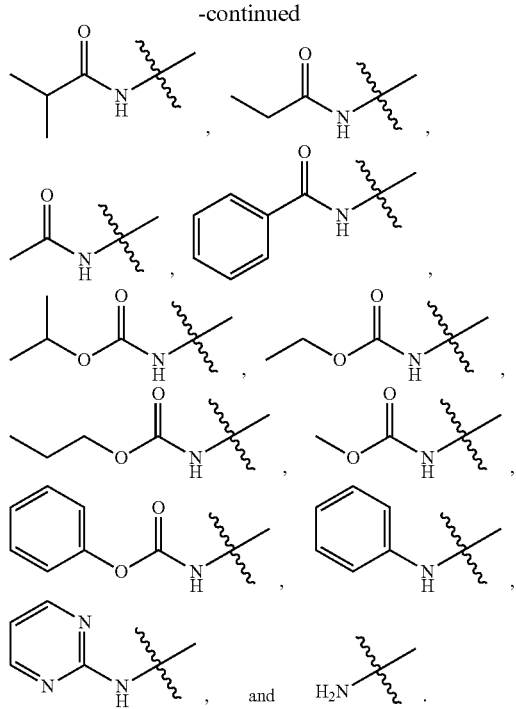
In certain cases of formula (II) or (III), R¹ is selected from:
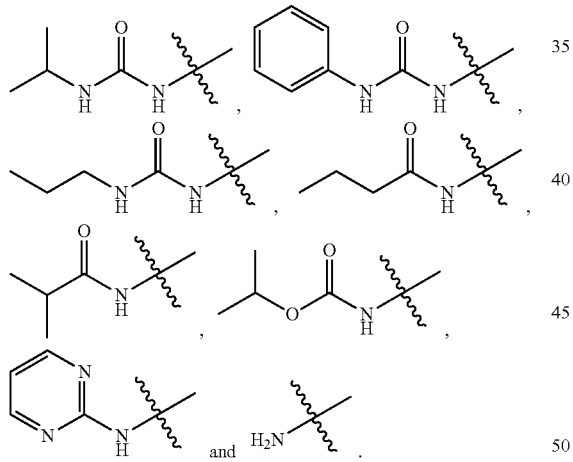
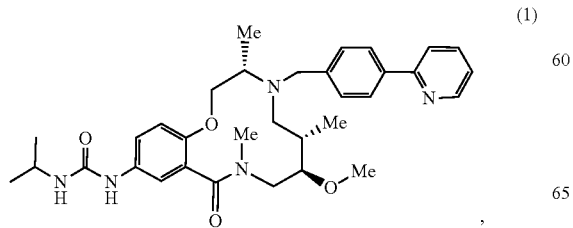
In some embodiments, the subject BAF modulating compound is described by the structure of any one of compounds (1) to (10).
(1)
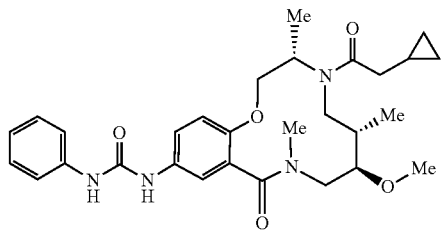
-continued
(2)
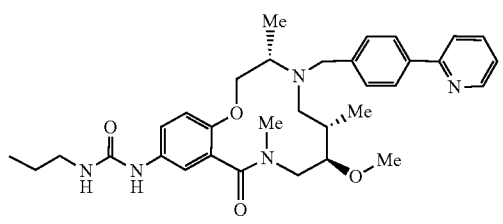
(3)
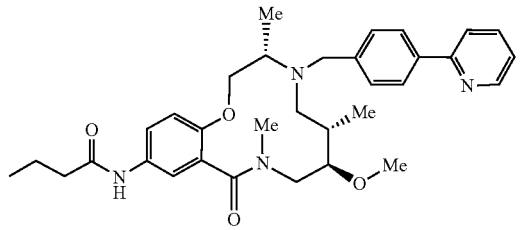
(4)
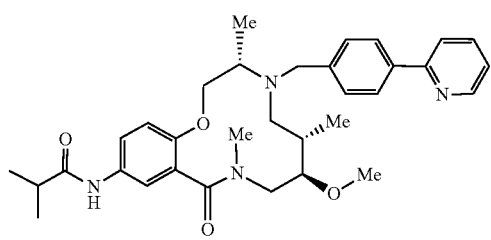
(5)
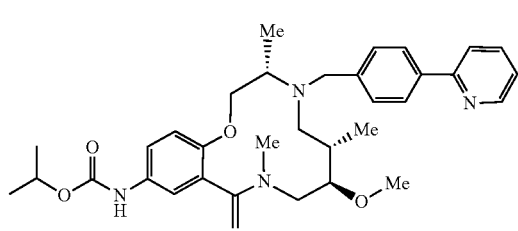
(6)
(7)
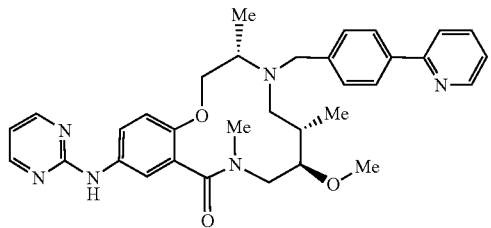

(8)

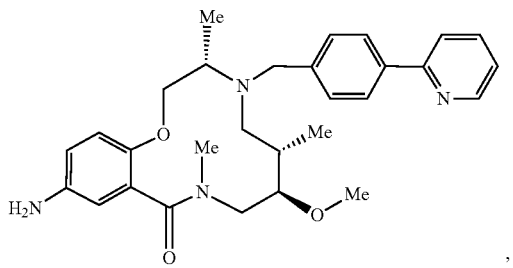

(9)

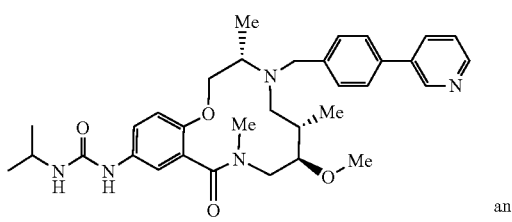

and (10)

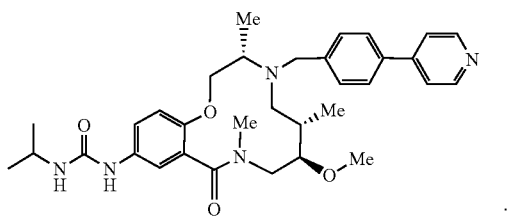

In certain embodiments, the subject BAF modulating compound is described by the structure of (1), also referred to as Baficillin 1.

(1)

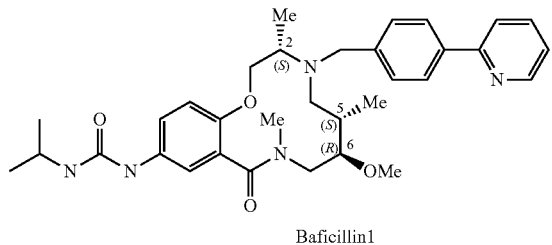

Baficillin1

This disclosure includes any one of the described BAF modulating compound, stereoisomers thereof, salts thereof (e.g., pharmaceutically acceptable salts), and/or solvate, hydrate and/or prodrug forms thereof. It will be appreciated that all permutations of stereoisomers, salts, solvates, hydrates, and prodrugs are meant to be included in this disclosure.

The invention can be practiced with a pharmaceutical composition that includes any one of the BAF modulating compounds of this disclosure (either alone or in the presence of one or more additional active agents) present in a pharmaceutically acceptable vehicle.

In some cases, the BAF modulating compounds, or a prodrug form thereof, are provided in the form of pharmaceutically acceptable salts. Compounds containing an amine or nitrogen containing heteraryl group may be basic in nature and accordingly may react with any number of inorganic and organic acids to form pharmaceutically acceptable acid addition salts. Acids commonly employed to form such salts include inorganic acids such as hydrochloric, hydrobromic, hydriodic, sulfuric and phosphoric acid, as well as organic acids such as para-toluenesulfonic, methanesulfonic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, β-hydroxybutyrate, glycollate, maleate, tartrate, methanesulfonate, propanesulfonates, naphthalene-1-sulfonate, naphthalene-2-sulfonate, mandelate, hippurate, gluconate, lactobionate, and the like salts. In certain specific embodiments, pharmaceutically acceptable acid addition salts include those formed with mineral acids such as hydrochloric acid and hydrobromic acid, and those formed with organic acids such as fumaric acid and maleic acid.

In some embodiments, the subject compounds, prodrugs, stereoisomers or salts thereof are provided in the form of a solvate (e.g., a hydrate). The term "solvate" as used herein refers to a complex or aggregate formed by one or more molecules of a solute, e.g. a prodrug or a pharmaceutically-acceptable salt thereof, and one or more molecules of a solvent. Such solvates are typically crystalline solids having a substantially fixed molar ratio of solute and solvent. Representative solvents include by way of example, water, methanol, ethanol, isopropanol, acetic acid, and the like. When the solvent is water, the solvate formed is a hydrate.

Formulation of Medicaments

Preparation and formulation of pharmaceutical agents for use according to this invention can incorporate standard technology, as described, for example, in the current edition of *Remington: The Science and Practice of Pharmacy*. The Formulation will typically be optimized for administration to the target tissue, for example, by local administration, in a manner that enhances access of the active agent to the target cells and providing the optimal duration of effect, while minimizing side effects or exposure to tissues that are not involved in the condition being treated.

Pharmaceutical preparations for use in treating BAF complex-related conditions and other diseases can be prepared by mixing a BAF complex modulating compound with a pharmaceutically acceptable base or carrier and as needed one or more pharmaceutically acceptable excipients. Exemplary excipients and additives that can be used include surfactants (for example, polyoxyethylene and block copolymers); buffers and pH adjusting agents (for example, hydrochloric acid, sodium hydroxide, phosphate, citrate, and sodium cyanide); tonicity agents (for example, sodium bisulfite, sodium sulfite, glycerin, and propylene glycol); and chelating agents (for example, ascorbic acid, sodium edetate, and citric acid).

Depending on the target tissue, it may be appropriate to formulate the pharmaceutical composition for sustained or timed release. Oral timed release formulations may include a mixture of isomeric variants, binding agents, or coatings.

Injectable time release formulations may include the active agent in combination with a binding agent, encapsulating agent, or microparticle.

This invention provides commercial products that are kits that enclose unit doses of one or more of the agents or compositions described in this disclosure. Such kits typically comprise a pharmaceutical preparation in one or more containers. The preparations may be provided as one or more unit doses (either combined or separate). The kit may contain a device such as a syringe for administration of the agent or composition in or around the target tissue of a subject in need thereof. The product may also contain or be accompanied by an informational package insert describing the use and attendant benefits of the drugs in treating the target condition, and optionally an appliance or device for delivery of the composition.

BAF Complex-Related Conditions Suitable for Treatment

The BAF complex modulating compounds of this disclosure can be used to inhibit a SWI/SNF (BAF) chromatin remodeling complex of interest, and find use in the treatment of various diseases, disorders, or conditions related to mutations in or malfunction of SWI/SNF. Human SWI/SNF (BAF) complexes are a diverse family of ATP-dependent chromatin remodelers that exhibit combinatorial specificity to regulate specific genetic programs. Due to the many diverse functions of the BAF complex, ranging from opposition of Polycomb-repressed genes to direct interaction with Topoisomerases and mediated genome stability, inhibitors of the SWI/SNF complex are of broad utility in human disease. The SWI/SNF or BAF complex is mutated in roughly 20% of human cancers, and associated with a host of neurological diseases including Coffin-Siris syndrome, autism, Nicholaides-Baraitser Syndrome, Kleefstra Syndrome, among others. Further, the SWI/SNF complex has been implicated in HIV-1 Tat mediated transcription, indicating a potential use for reversing HIV latency. Non-limiting examples of current interest include the treatment fo a neurological disease and the treatment of cancer, as illustrated in the following section.

Treatment of Cancer

It has now been discovered that compounds of this disclosure find use in methods of treating cancer involving BAF inhibition and ATR inhibition. Ataxia telengiectasia and rad3-related (ATR) protein kinase is integral to the replication stress response. This disclosure provides BAF complex modulating compounds that can act as inhibitors on ARID1A-containing BAF complexes. Methods of treating cancer are provided that include a combination therapy using the subject BAF complex modulating compounds with inhibitors of the ATR kinase. The subject methods can lead to non-BAF mutated cancer cells undergoing a hyper-synthetic lethal effect, particularly in highly mutated cancer lines. In some cases, the BAF complex modulating compounds can block the de-repressive function of a target BAF complex and have low or no toxicity to cells when used alone. Administration of the subject compounds can sensitize the target cells to ATR inhibition. As such, in some cases, the subject methods provide a synergistic effect, e.g., synergistic hyper-synthetic-lethality on the target cells.

Another aspect of this invention is directed towards a method of treating cancer in a subject in need thereof, comprising administration of a compound of this invention or a pharmaceutically acceptable salt thereof, in combination with an additional therapeutic agent that is an ATR inihibitor. In some embodiments, said method comprises the sequential or co-administration of the compound or a pharmaceutically acceptable salt thereof, and the additional therapeutic agent, e.g., an ATR inhibitor. In some embodiments, the cancer is a highly mutated cancer, and the pharmaceutical composition and the ATR inhibitor act synergistically to kill cancer cells of the subject. In some embodiments, the synergistic action allows a reduction in the effective dose of the ATR inhibitor to an amount below a threshold of toxicity.

In some embodiments, the subject has cancer cells harboring a BAF complex mutation.

In some embodiments, a method is provided for treating a BRCA1 cancer, the method comprising administering to a subject in need thereof an effective amount of the pharmaceutical composition disclosed herein to treat the BRCA1 cancer.

One aspect of the invention relates to a method of inhibiting BAF complex and ATR kinase activity in a patient, which method comprises administering to the patient a compound described herein, or a composition comprising said compound, and a ATR inhibitor compound or composition. In some embodiments, said method is used to treat or prevent a condition selected from proliferative and hyperproliferative diseases, such as cancer.

ATR suppression to clinically relevant levels has the potential to be effective in a wide spectrum of cancers. ATR belongs to a family of kinases, i.e., phosphatidyl inositol 3' kinase-related kinases (PIKKs), that are involved in the signaling and repair of DNA damage. While other members of this family (ataxia-telangiectasia mutated (ATM) and DNA-dependent protein kinase catalytic subunit (DNA-PKcs)) are required for the repair of double strand breaks (DSBs), ATR is recruited to, and activated by, single strand DNA (ssDNA) generated at stalled replication forks or as an intermediate in the repair of DSBs. Upon replication fork stalling activated ATR phosphorylates the downstream kinase Chk1 resulting in stabilization of the replication fork and inhibition of cell-cycle progression, thus allowing time for resolution of the stress and continued replication. When the ATR-Chk1 pathway is disrupted stalled replication forks collapse into DSBs, thus if unresolved, replication stress can cause genomic instability and negatively impact cell survival.

ATR inhibition is synthetically lethal in cancers with mutations that cause oncogenic stress or disruption of the DNA damage response (DDR). Genetic changes associated with cancer promote the activation of the replicative stress response and other DNA damage response (DDR) pathways. Such oncogenic stress inducing alterations include K-RasG12D and H-RasG12V mutations, and c-Myc amplification. Activation of the DDR by oncogenic stress has been proposed to contribute to selection for mutation, and loss of, p53 and ATM. Mutations in the tumor suppressor p53 are found in about 50% of all human cancers. Similar mutation frequencies are observed in the oncogene Myc, while significant numbers of cancers also harbor mutations in the Ras family of genes and to a lesser degree the DDR protein ATM. Alterations in these genes cause an increased reliance on the ATR-Chk1 pathway for genome maintenance. ATR inhibition elicits synthetic lethality under each of these cancer associated conditions.

Any convenient ATR inhibitors can be utilized in conjunction with the BAF complex modulating compounds (e.g., as described herein), compositions, kits and methods of this disclosure. ATR inhibitors of interest include, but are not limited to, VE-821 (CAS# 1232410-49-9), VE-822 (CAS# 1232416-25-9), ETP-46464 (CAS# 1345675-02-6), NU6027 (CAS# 220036-08-8), BEZ235 (CAS# 915019-65-7), AZD6738 (CAS# 1352226-88-0) and those ATR inhibitors described by Brelin et al. in U.S. Pat. No. 9,981,989, Ahmad et al. in U.S. Pat. No. 9,718,827 and Toledo et al. (Nat Struct Mol Biol. 2011 Jun; 18(6): 721-727), the disclosures of which are herein incorporated by reference in their entirety.

The macrocyclic compounds, compositions containing the same and methods of treatment of the present invention have utility in treating many disease conditions, including cancer (e.g., central nerve system, breast, pancreatic, lung, ovarian, leukemia, Lymphoma, melanoma, renal, prostate, colorectal, brain, and glioblastoma).

In at least one embodiment, the compositions and methods of the present invention are used to treat diseases such as ocular melanoma, desmoplastic round cell tumor, chondrosarcoma, leptomengial disease, diffuse large B-cell lymphoma, Acute Lymphoblastic Leukemia, Acute Myeloid Leukemia, Adrenocortical Carcinoma, AIDS-Related Cancers, AIDS-Related Lymphoma, Anal or Rectal Cancer, Appendix Cancer, Astrocytomas, and Atypical Teratoid/Rhabdoid Tumor. In at least one embodiment, the compositions and methods of the present invention are used to treat diseases such as Basal Cell Carcinoma, Bile Duct Cancer, Bladder Cancer, Bone Cancer, Osteosarcoma and Malignant Fibrous Histiocytoma, Brain Tumor, Breast Cancer, Prostate Cancer, Bronchial Tumors, Burkitt Lymphoma, and Spinal Cord Tumors. In at least one embodiment, the compositions and methods of the present invention are used to treat diseases such as Carcinoid Tumor, Carcinoma of Unknown Primary, Central Nervous System Atypical Teratoid/Rhabdoid Tumor, Leptomeningeal Disease, Central Nervous System Embryonal Tumors, Central Nervous System Lymphoma, Cervical Cancer, Chordoma, Chronic Lymphocytic Leukemia, Chronic Myelogenous Leukemia, Chronic Myeloproliferative Disorders, Colon Cancer, Colorectal Cancer, Craniopharyngioma, and Cutaneous T-Cell Lymphoma. In at least one embodiment, the compositions and methods of the present invention are used to treat diseases such as Endometrial Cancer, Ependymoblastoma, Ependymoma, Esophageal Cancer, Ewing Sarcoma Family of Tumors, Extracranial Germ Cell Tumor, Extragonadal Germ Cell Tumor, Extrahepatic Bile Duct Cancer, and Eye Cancer.

In at least one embodiment, the compositions and methods of the present invention are used to treat diseases such as Gallbladder Cancer, Gastric (Stomach) Cancer, Gastrointestinal Carcinoid Tumor, Gastrointestinal Stromal Tumor (GIST), Germ Cell Tumor, Gestational Trophoblastic Tumor, and Glioma. In at least one embodiment, the compositions and methods of the present invention are used to treat cancer selected from the group consisting of Hairy Cell Leukemia, Head and Neck Cancer, Hepatocellular (Liver) Cancer, Histiocytosis, Hodgkin Lymphoma, and Hypopharyngeal Cancer. In at least one embodiment, the compositions and methods of the present invention are used to treat diseases such as Kaposi Sarcoma, and Kidney (Renal Cell) Cancer. In at least one embodiment, the compositions and methods of the present invention are used to treat diseases such as Langerhans Cell Histiocytosis, Laryngeal Cancer, Lip and Oral Cavity Cancer, Liver Cancer, Lung Cancer, Non-Hodgkin Lymphoma, and Primary Central Nervous System Lymphoma. In at least one embodiment, the compositions and methods of the present invention are used to treat diseases such as Waldenstrom's macroglobulinemia (lymphoplasmacytic lymphoma), Malignant Fibrous Histiocytoma of Bone and Osteosarcoma, Medulloblastoma, Medulloepithelioma, Melanoma, Merkel Cell Carcinoma, Mesothelioma, Metastatic Squamous Neck Cancer with Occult Primary, Multiple Endocrine Neoplasia Syndrome, Mouth Cancer, Multiple Myeloma/Plasma Cell Neoplasm, Mycosis Fungoides, Myelodysplastic Syndromes, Myelodysplastic/Myeloproliferative Neoplasms, Multiple Myeloma, and Myeloproliferative Disorders.

In at least one embodiment, the compositions and methods of the present invention are used to treat diseases such as Nasal Cavity and Paranasal Sinus Cancer, Nasopharyngeal Cancer, and Neuroblastoma. In at least one embodiment, the compositions and methods of the present invention are used to treat diseases such as Oral Cancer, Lip and Oral Cavity Cancer, Oropharyngeal Cancer, Osteosarcoma and Malignant Fibrous Histiocytoma of Bone, Ovarian Cancer, Ovarian Germ Cell Tumor, Ovarian Epithelial Cancer, and Ovarian Low Malignant Potential Tumor. In at least one embodiment, the compositions and methods of the present invention are used to treat diseases such as Pancreatic Cancer, Papillomatosis, Paranasal Sinus and Nasal Cavity Cancer, Parathyroid Cancer, Penile Cancer, Pharyngeal Cancer, Pineal Parenchymal Tumors of Intermediate Differentiation, Pineoblastoma and Supratentorial Primitive Neuroectodermal Tumors, Pituitary Tumor, Pleuropulmonary Blastoma, Pregnancy and Breast Cancer, and Prostate Cancer. In at least one embodiment, the compositions and methods of the present invention are used to treat cancer selected from the group consisting of Rectal Cancer, Renal Pelvis and Ureter, Respiratory Tract Carcinoma Involving the NUT Gene on Chromosome 15, Retinoblastoma, and Rhabdomyosarcoma.

In some embodiments, the cancer is selected from the cancers described herein. In some embodiments, said cancer is lung cancer, head and neck cancer, pancreatic cancer, gastric cancer, or brain cancer. In other embodiments, the cancer is selected from a cancer of the lung or the pancreas. In at least one embodiment, the compositions and methods of the present invention are used to treat prostate cancer. In yet other embodiments, the cancer is selected from non-small cell lung cancer, small cell lung cancer, pancreatic cancer, biliary tract cancer, head and neck cancer, bladder cancer, colorectal cancer, glioblastoma, esophageal cancer, breast cancer, hepatocellular carcinoma, or ovarian cancer. In at least one embodiment, the compositions and methods of the present invention are used to treat a proliferative skin disorder.

The utility of the methods and compositions of the present invention is not limited to any particular animal species. In at least one embodiment, a subject treated according to methods and using compositions of the present invention, can be mammalian or non-mammalian. In at least one embodiment, a mammalian subject can be any mammal including, but not limited to, a human; a non-human primate; a rodent such as a mouse, rat, or guinea pig; a domesticated pet such as a cat or dog; a horse, cow, pig, sheep, goat, or rabbit. In at least one embodiment, a non-mammalian subject can be any non-mammal including, but not limited to, a bird such as a duck, goose, chicken, or turkey. In at least one embodiment, subjects can be either gender and can be any age.

Modes of Administration and Dosage Forms

The exact amount of compound(s) required for treatment will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the condition being treated. In certain embodiments, the compounds of the invention may be administered orally at dosage levels of about 0.01 mg/kg to about 100 mg/kg, one or more times a day, to obtain the desired therapeutic effect.

Liquid dosage forms for oral administration include, but are not limited to, pharmaceutically acceptable emulsions, microemulsions, solutions, suspensions, syrups and elixirs. Injectable preparations, for example, sterile injectable aqueous or oleaginous suspensions may be formulated according to the known art using suitable dispersing or wetting agents and suspending agents. In order to prolong the effect of a compound of the present invention, it is often desirable to slow the absorption of the compound from subcutaneous or intramuscular injection. This may be accomplished by the use of a liquid suspension of crystalline or amorphous material with poor water solubility.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. The compositions of the present invention may be administered orally, parenterally, by inhalation spray, topically, rectally, nasally, buccally, vaginally or via an implanted reservoir. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of inhibitor will also depend upon the particular compound in the composition.

Methods of Inhibiting BAF Complexes

The subject agent may be employed to inhibit the formation or function/activity of BAF complexes in cells in vitro or in vivo. For example, in some aspects of the methods, the methods comprise contacting a cell with a subject agent, e.g. as described herein, in vitro, for research purposes. In some aspects of the methods, the methods comprise contacting a cell with an agent in vivo, e.g. administering to the individual in need thereof an effective amount of an agent that inhibits the formation or function of BAF complexes and treat synovial sarcoma. In some cases, the BAF complex is a wild type BAF complex.

Cells to be contacted may be from or in any mammalian species, e.g. murine, rodent, canine, feline, equine, bovine, ovine, primate, human, etc. When performing the subject methods in vitro, cells may be from established cell lines or they may be primary cells, where "primary cells", "primary cell lines", and "primary cultures" are used interchangeably herein to refer to cells and cells cultures that have been derived from a subject and allowed to grow in vitro for a limited number of passages, i.e. splittings, of the culture. For example, primary cultures are cultures that may have been passaged 0 times, 1 time, 2 times, 4 times, 5 times, 10 times, or 15 times, but not enough times go through the crisis stage. Typically, the primary cell lines of the present invention are maintained for fewer than 10 passages in vitro.

If the cells are primary cells, they may be harvested from an individual by any convenient method. For example, cells, e.g. skin, muscle, bone marrow, spleen, liver, pancreas, lung, intestine, stomach tissue, etc. may be harvested by biopsy. Of particular interest are cells of muscle, fat, fibrous tissue, blood vessels, or other supporting tissue of the body, including synovial tissue, from which synovial sarcomas more usually arise. An appropriate solution may be used for dispersion or suspension of the harvested cells. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc. The cells may be used immediately, or they may be stored, frozen, for long periods of time, being thawed and capable of being reused. In such cases, the cells will usually be frozen in 10% DMSO, 50% serum, 40% buffered medium, or some other such solution as is commonly used in the art to preserve cells at such freezing temperatures, and thawed in a manner as commonly known in the art for thawing frozen cultured cells.

To inhibit the formation or function of target BAF complexes, the subject compound is provided to the cells for about 30 minutes to about 24 hours, e.g., 1 hour, 1.5 hours, 2 hours, 2.5 hours, 3 hours, 3.5 hours 4 hours, 5 hours, 6 hours, 7 hours, 8 hours, 12 hours, 16 hours, 18 hours, 20 hours, or any other period from about 30 minutes to about 24 hours, which may be repeated with a frequency of about every day to about every 4 days, e.g., every 1.5 days, every 2 days, every 3 days, or any other frequency from about every day to about every four days. The agent(s) may be provided to the subject cells one or more times, e.g. one time, twice, three times, or more than three times, and the cells allowed to incubate with the agent(s) for some amount of time following each contacting event e.g. 16-24 hours, after which time the media is replaced with fresh media and the cells are cultured further.

Contacting the cells with the subject agent may occur in any culture media and under any culture conditions that promote the survival of the cells. For example, cells may be suspended in any appropriate nutrient medium that is convenient, such as Iscove's modified DMEM or RPMI 1640, supplemented with fetal calf serum or heat inactivated goat serum (about 5-10%), L-glutamine, a thiol, particularly 2-mercaptoethanol, and antibiotics, e.g. penicillin and streptomycin. The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors.

In certain embodiments, the subject compounds have no significant effect on the viability of a mammalian cell, as determined by a cell cytotoxicity assay, e.g., as determined by administering a subject compound to a target cell and determining the number of viable cells present. The subject compounds may exhibit a % cell viability, as compared to a control (e.g., a DMSO control), of 15% or more, such as 20% or more, 30% or more, 40% or more, 50% or more, 60% or more, 70% or more, 80% or more, 90% or more, 100% or more, 120% or more, or even higher.

A subject compound (e.g., as described herein) may inhibit at least one activity or function of the BAF complex in the range of 10% to 100%, e.g., by 10% or more, 20% or more, 30% or more, 40% or more, 50% or more, 60% or more, 70% or more, 80% or more, or 90% or more. Any convenient assays may be utilized to measure the inhibition of a complex, either directly or indirectly, e.g., via observation of an acitivty or function in a cell that is associated with the target BAF complex. The protocols that may be employed in determining activity are numerous, and include but are not limited to cell-free assays, e.g., binding assays; assays using purified BAF complex, cellular assays in which a cellular phenotype is measured, e.g., gene expression assays; and in vivo assays that involve a particular animal (which, in certain embodiments may be an animal model for a condition related to the target condition). In certain assays, a subject compound may inhibit its target with an $IC_{50}$ of $1\times10^{-6}$ M or less (e.g., $1\times10^{-6}$ M or less, $1\times10^{-7}$ M or less, $1\times10^{-8}$ M or less, $1\times10^{-9}$ M or less, $1\times10^{-10}$ M or less, or $1\times10^{-11}$ M or less).

Definitions

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

By "BAF complexes" (also called mSWI/SNF, for mammalian SWItch/Sucrose NonFermentable, complexes), it is meant ATP-dependent chromatin remodeling complexes comprising proteins encoded by the SWI/SNF genes and other polypeptides, e.g. SMARCA4 (BRG1), SMARCA2 (BRM), ARID1A (BAF250A), ARID1B (BAF250B), ARID2 (BAF200), PBRM1 (BAF180), BCL11A, BCL11B, BCL7A, BCL7B, BCL7C, SMARCB1 (BAF47), SMARCD1 (BAF60A), SMARCD2 (BAF60B), SMARCD3 (BAF60c), SMARCC1 (BAF155), SMARCC2 (BAF170), PHF10 (BAF45A), DPF1 (BAF45B), DPF2 (BAF45C), DPF3 (BAF45D), ACTL6A (BAF53A), ACTL6B (BAF53B), BRD9, BRD7, SS18, CREST (SS18L1), and SMARCE1 (BAF57), that remodel the way DNA is packaged. The interaction of the SWI/SNF complex with chromatin modulates the binding of transcription factors to that chromatin and the transcriptional activity at those loci.

Successful "treatment" of a condition according to this invention may have any effect that is beneficial to the subject being treated. This includes decreasing severity, duration, or progression of a condition, or of any adverse signs or symptoms resulting therefrom. In some circumstances, agents can also be used to prevent or inhibit presentation of a condition for which a subject is susceptible, for example, because of an inherited susceptibility of because of medical history.

A "therapeutically effective amount" is an amount of a compound of this disclosure that (i) treats the particular disease, condition, or disorder, (ii) attenuates, ameliorates, or eliminates one or more symptoms of the particular disease, condition, or disorder, (iii) prevents or delays the onset of one or more symptoms of the particular disease, condition, or disorder described herein, (iv) prevents or delays progression of the particular disease, condition or disorder, or (v) at least partially reverses damage caused by the condition prior to treatment.

The term "salt thereof" means a compound formed when a proton of an acid is replaced by a cation, such as a metal cation or an organic cation and the like. Where applicable, the salt is a pharmaceutically acceptable salt, although this is not required for salts of intermediate compounds that are not intended for administration to a patient. By way of example, salts of the present compounds include those wherein the compound is protonated by an inorganic or organic acid to form a cation, with the conjugate base of the inorganic or organic acid as the anionic component of the salt.

The term "pharmaceutically acceptable salt" means a salt which is acceptable for administration to a patient, such as a mammal (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

A "pharmaceutically acceptable vehicle" may be a vehicle approved by a regulatory agency of the Federal or a state government or listed in the U.S. Pharmacopeia or other generally recognized pharmacopeia for use in mammals, such as humans. The term "vehicle" refers to a diluent, adjuvant, excipient, or carrier with which a Bcl inhibitor compound is formulated for administration to a mammal.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

"Stereoisomer" and "stereoisomers" refer to compounds that have same atomic connectivity but different atomic arrangement in space. Stereoisomers include cis-trans isomers, E and Z isomers, enantiomers, and diastereomers.

"Tautomer" refers to alternate forms of a molecule that differ only in electronic bonding of atoms and/or in the position of a proton, such as enol-keto and imine-enamine tautomers, or the tautomeric forms of heteroaryl groups containing a —N=C(H)-NH— ring atom arrangement, such as pyrazoles, imidazoles, benzimidazoles, triazoles, and tetrazoles. A person of ordinary skill in the art would recognize that other tautomeric ring atom arrangements are possible.

"Enantiomer" refers to one of a pair of chiral molecules that are mirror images of each other. Enantiomers can be referred to as (+) or −) enantiomers. Enantiomers can be referred to as (S)— or (R)-enantiomers. The term "racemic" or "racemate", and other like terms refer to generally equimolar proportions of a (+)-enantiomer and a (−)-enantiomer of a compound in a composition.

The term "enantiomerically enriched" or "enriched enantiomer" denotes that the compound comprises 75% or more by weight of the enantiomer, such as 80% or more by weight, 85% or more by weight, more than 90% or more by weight, more than 91% or more by weight, more than 92% or more by weight, more than 93% or more by weight, more than 94% or more by weight, more than 95% or more by weight, more than 96% or more by weight, or more than 97% or more by weight of the enantiomer.

The term "stereoisomerically enriched" or "enriched stereoisomer" denotes that the compound comprises 75% or more by weight of the stereoisomer, such as 80% or more by weight, 85% or more by weight, more than 90% or more by weight, more than 91% or more by weight, more than 92% or more by weight, more than 93% or more by weight, more than 94% or more by weight, more than 95% or more by weight, more than 96% or more by weight, or more than 97% or more by weight of the stereoisomer.

It will be appreciated that the term "or a stereoisomer, solvate or salt thereof" is intended to include all permutations of salts, solvates and stereoisomers, such as a solvate of a pharmaceutically acceptable salt of a stereoisomer of the subject compound.

The term "solvate" refers to a complex or aggregate formed by one or more molecules of a solute, e.g. a prodrug or a pharmaceutically-acceptable salt thereof, and one or more molecules of a solvent. Such solvates are typically crystalline solids having a substantially fixed molar ratio of solute and solvent. Representative solvents include by way of example, water, methanol, ethanol, isopropanol, acetic acid, and the like. When the solvent is water, the solvate formed is a hydrate.

"Prodrug" refers to a derivative of an active agent that requires a transformation within the body to release the active agent. The transformation can be an enzymatic transformation. Prodrugs are frequently, although not necessarily, pharmacologically inactive until converted to the active agent. "Promoiety" refers to a form of protecting group that, when used to mask a functional group within an active agent, converts the active agent into a prodrug. The promoiety can be attached to the agent via bond(s) that are cleaved by enzymatic or non enzymatic means in vivo. Any convenient prodrug forms of the compounds can be prepared, e.g., according to the strategies and methods described by Rautio et al. ("Prodrugs: design and clinical applications", Nature Reviews Drug Discovery 7, 255-270 (February 2008)).

Unless otherwise stated or required, each of the compound structures referred to in the invention include conjugate acids and bases having the same structure, crystalline and amorphous forms of those compounds, pharmaceutically acceptable salts, and prodrugs. This includes, for example, polymorphs, solvates, hydrates, unsolvated polymorphs (including anhydrates), and phosphorylated and unphosphorylated forms of the compounds.

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Where compounds described herein contain one or more chiral centers and/or double-bond isomers (i.e., geometric isomers), enantiomers or diastereomers, all possible enantiomers and stereoisomers of the compounds including the stereoisomerically pure form (e.g., geometrically pure, enantiomerically pure or diastereomerically pure) and enantiomeric and stereoisomeric mixtures are included in the description of the compounds herein. Enantiomeric and stereoisomeric mixtures can be resolved into their component enantiomers or stereoisomers using separation techniques or chiral synthesis techniques well known to the skilled artisan. The compounds can also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that can be incorporated into the compounds disclosed herein include, but are not limited to, $^{2}H$, $^{3}H$, $^{11}C$, $^{13}C$, $^{14}C$, $^{15}N$, $^{18}O$, $^{17}O$, etc. Compounds can exist in unsolvated forms as well as solvated forms, including hydrated forms. In general, compounds can be hydrated or solvated. Certain compounds can exist in multiple crystalline or amorphous forms. In general, all physical forms are equivalent for the uses contemplated herein and are intended to be within the scope of the present disclosure.

The term "alkyl" as used herein refers to a branched or unbranched saturated hydrocarbon group (i.e., a monoradical) typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although not necessarily, alkyl groups herein may contain 1 to about 18 carbon atoms, and such groups may contain 1 to about 12 carbon atoms.

The term "lower alkyl" intends an alkyl group of 1 to 6 carbon atoms. "Substituted alkyl" refers to alkyl substituted with one or more substituent groups, and this includes instances wherein two hydrogen atoms from the same carbon atom in an alkyl substituent are replaced, such as in a carbonyl group (i.e., a substituted alkyl group may include a —C(=O)— moiety). The terms "heteroatom-containing alkyl" and "heteroalkyl" refer to an alkyl substituent in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The term "substituted alkyl" refers to an alkyl group as defined herein wherein one or more carbon atoms in the alkyl chain have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxyalkyl, thioaryloxy, thioheteroarylyoxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R' and R" may be the same or different and are chosen from hydrogen, optionally substituted alkyl, cycloalkyl, alkenyl, cycloalkenyl, alkynyl, aryl, heteroaryl and heterocyclic.

The term "alkenyl" as used herein refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Generally, although again not necessarily, alkenyl groups herein may contain 2 to about 18 carbon atoms, and for example may contain 2 to 12 carbon atoms. The term "lower alkenyl" intends an alkenyl group of 2 to 6 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

"Substituted alkylene" refers to an alkylene group having from 1 to 3 hydrogens replaced with substituents as described for carbons in the definition of "substituted" below.

The term "alkynyl" as used herein refers to a linear or branched hydrocarbon group of 2 to 24 carbon atoms containing at least one triple bond, such as ethynyl, n-propynyl, and the like. Generally, although again not necessarily, alkynyl groups herein may contain 2 to about 18 carbon atoms, and such groups may further contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkaryl" or "aralkyl" refers to the groups -alkylene-aryl and -substituted alkylene-aryl where alkylene, substituted alkylene and aryl are defined herein.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like. The term "alkoxy" also refers to the groups alkenyl-O—, cycloalkyl-O—, cycloalkenyl-O—, and alkynyl-O—, where alkenyl, cycloalkyl, cycloalkenyl, and alkynyl are as defined herein.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "haloalkyl" refers to a substituted alkyl group as described above, wherein one or more hydrogen atoms on the alkyl group have been substituted with a halo group. Examples of such groups include, without limitation, fluoroalkyl groups, such as trifluoromethyl, difluoromethyl, trifluoroethyl and the like.

"Alkenyl" refers to straight chain or branched hydrocarbyl groups having from 2 to 6 carbon atoms and preferably 2 to 4 carbon atoms and having at least 1 and preferably from 1 to 2 sites of double bond unsaturation. This term includes, by way of example, bi-vinyl, allyl, and but-3-en-1-yl. Included within this term are the cis and trans isomers or mixtures of these isomers.

The term "substituted alkenyl" refers to an alkenyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclyl-C(O)—, and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. For example, acyl includes the "acetyl" group CH$_3$C(O)—.

The term "aryl" as used herein, and unless otherwise specified, refers to an aromatic substituent generally, although not necessarily, containing 5 to 30 carbon atoms and containing a single aromatic ring or multiple aromatic rings that are fused together, directly linked, or indirectly linked (such that the different aromatic rings are bound to a common group such as a methylene or ethylene moiety). Aryl groups may, for example, contain 5 to 20 carbon atoms, and as a further example, aryl groups may contain 5 to 12 carbon atoms. For example, aryl groups may contain one aromatic ring or two or more fused or linked aromatic rings (i.e., biaryl, aryl-substituted aryl, etc.). Examples include phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom, as will be described in further detail infra. Aryl is intended to include stable cyclic, heterocyclic, polycyclic, and polyheterocyclic unsaturated $C_3$-$C_{14}$ moieties, exemplified but not limited to phenyl, biphenyl, naphthyl, pyridyl, furyl, thiophenyl, imidazoyl, pyrimidinyl, and oxazoyl; which may further be substituted with one to five members selected from the group consisting of hydroxy, $C_1$-$C_8$ alkoxy, $C_1$-$C_8$ branched or straight-chain alkyl, acyloxy, carbamoyl, amino, N-acylamino, nitro, halogen, trifluoromethyl, cyano, and carboxyl (see e.g. Katritzky, Handbook of Heterocyclic Chemistry). If not otherwise indicated, the term "aryl" includes unsubstituted, substituted, and/or heteroatom-containing aromatic substituents.

The term "aralkyl" refers to an alkyl group with an aryl substituent, and the term "alkaryl" refers to an aryl group with an alkyl substituent, wherein "alkyl" and "aryl" are as defined above. In general, aralkyl and alkaryl groups herein contain 6 to 30 carbon atoms. Aralkyl and alkaryl groups may, for example, contain 6 to 20 carbon atoms, and as a further example, such groups may contain 6 to 12 carbon atoms.

"Aryloxy" refers to the group —O-aryl, wherein aryl is as defined herein, including, by way of example, phenoxy, naphthoxy, and the like, including optionally substituted aryl groups as also defined herein.

"Amino" refers to the group —NH$_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen.

The term "azido" or "azide" refers to the group —N$_3$.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclohexyl and the like. Such cycloalkyl groups include, by way of example, single ring structures such as cyclopropyl, cyclobutyl, cyclopentyl, cyclohexyl, and the like, or multiple ring structures such as adamantanyl, and the like.

The term "substituted cycloalkyl" refers to cycloalkyl groups having from 1 to 5 substituents, or from 1 to 3 substituents, selected from alkyl, substituted alkyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkenyl" refers to non-aromatic cyclic alkyl groups of from 3 to 10 carbon atoms having single or multiple rings and having at least one double bond and preferably from 1 to 2 double bonds.

The term "substituted cycloalkenyl" refers to cycloalkenyl groups having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Halo" or "halogen" refers to fluoro, chloro, bromo, and iodo.

"Hydroxy" or "hydroxyl" refers to the group —OH.

"Heteroaryl" refers to an aromatic group of from 1 to 15 carbon atoms, such as from 1 to 10 carbon atoms and 1 to 10 heteroatoms selected from the group consisting of oxygen, nitrogen, and sulfur within the ring. Such heteroaryl groups can have a single ring (such as, pyridinyl, imidazolyl or furyl) or multiple condensed rings in a ring system (for example as in groups such as, indolizinyl, quinolinyl, benzofuran, benzimidazolyl or benzothienyl), wherein at least one ring within the ring system is aromatic and at least one ring within the ring system is aromatic , provided that the point of attachment is through an atom of an aromatic ring. In certain embodiments, the nitrogen and/or sulfur ring atom(s) of the heteroaryl group are optionally oxidized to provide for the N-oxide (N→O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl, and trihalomethyl.

The term "heteroaralkyl" refers to the groups -alkylene-heteroaryl where alkylene and heteroaryl are defined herein. This term includes, by way of example, pyridylmethyl, pyridylethyl, indolylmethyl, and the like.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 20 ring atoms, including 1 to 10 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO$_2$-moieties.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and fused heterocycle.

In addition to the disclosure herein, the term "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with =O, =NR$^{70}$, =N—OR$^{70}$, =N$_2$ or =S) on saturated carbon atoms in the specified group or radical are, unless otherwise specified, —R$^{60}$, halo, =O, —OR$^{70}$, —SR$^{70}$, —NR$^{80}$R$^{80}$, trihalomethyl, —CN, —OCN, —SCN, —NO, —NO$_2$, =N$_2$, —N$_3$, —SO$_2$R$^{70}$, —SO$_2$O$^-$ M$^+$, —SO$_2$OR$^{70}$, —OSO$_2$R$^{70}$, —OSO$_2$O$^-$M$^+$, —OSO$_2$OR$^{70}$, —P(O)(O$^-$)$_2$(M$^+$)$_2$, —P(O)(OR$^{70}$)O$^-$ M$^+$, —P(O)(OR$^{70}$)$_2$, —C(O)R$^{70}$, —C(S)R$^{70}$, —C(NR$^{70}$)R$^{70}$, —C(O)O$^-$ M$^+$, —C(O)OR$^{70}$, —C(S)OR$^{70}$, —C(O)NR$^{80}$R$^{80}$, —OC(NR$^{70}$)NR$^{80}$R$^{80}$, —OC(O)R$^{70}$, OC(S)R$^{70}$, —OC(O)O $^-$M$^+$, —OC(O)OR$^{70}$, —OC(S)OR$^{70}$, —NR$^{70}$C(O)R$^{70}$, —NR$^{70}$C(S)R$^{70}$, —NR$^{70}$CO$_2^-$ M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each R$^{70}$ is independently hydrogen or R$^{60}$; each R$^{80}$ is independently R$^{70}$ or alternatively, two R$^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or C$_1$-C$_3$ alkyl substitution; and each M$^+$ is a counter ion with a net single positive charge. Each M$^+$ may independently be, for example, an alkali ion, such as K$^+$, Na$^+$, Li$^+$; an ammonium ion, such as $^+$N(R$^{60}$)$_4$; or an alkaline earth ion, such as [Ca$^{2+}$]$_{0.5}$, [Mg$^{2+}$]$_{0.5}$, or [Ba$^{2+}$]$_{0.5}$ ("subscript 0.5 means that one of the counter ions for such divalent alkali earth ions can be an ionized form of a compound of the invention and the other a typical counter ion such as chloride, or two ionized compounds disclosed herein can serve as counter ions for such divalent alkali earth ions, or a doubly ionized compound of the invention can serve as the counter ion for such divalent alkali earth ions). As specific examples, —NR$^{80}$R$^{80}$ is meant to include —NH$_2$, —NH-alkyl, N-pyrrolidinyl, N-piperazinyl, 4N-methyl-piperazin-1-yl and N-morpholinyl.

In addition to the disclosure herein, substituent groups for hydrogens on unsaturated carbon atoms in "substituted" alkene, alkyne, aryl and heteroaryl groups are, unless otherwise specified, —R$^{60}$, halo, —O$^-$M$^+$, —OR$^{70}$, —SR$^{70}$, —S$^-$M$^+$, —NR$^{80}$R$^{80}$, trihalomethyl, —CF$_3$, —CN, —OCN, —SCN, —NO, —NO$_2$, —N$_3$, —SO$_2$R$^{70}$, —SO$_3^-$M$^+$, —SO$_3$R$^{70}$, —OSO$_2$R$^{70}$, —OSO$_3^-$M$^+$, —OSO$_3$R$^{70}$, —PO$_3^{-2}$ (M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —CO$_2^-$M$^+$, —CO$_2$R$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OCO$_2^-$M$^+$, —OCO$_2$R$^{70}$, —OC(S)OR$^{70}$, —NR$^{70}$C(O)R$^{70}$, —NR$^{70}$C(S) R$^{70}$, —NR$^{70}$CO$_2^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined, provided that in case of substituted alkene or alkyne, the substituents are not —O$^-$M$^+$, —OR$^{70}$, —SR$^{70}$, or —S$^-$M$^+$.

In addition to the groups disclosed with respect to the individual terms herein, substituent groups for hydrogens on nitrogen atoms in "substituted" heteroalkyl and cycloheteroalkyl groups are, unless otherwise specified, —R$^{60}$, —O$^-$M$^+$, —OR$^{70}$, —SR$^{70}$, —S$^-$M$^+$, —NR$^{80}$R$^{80}$, trihalomethyl, —CF$_3$, —CN, —NO, —NO$_2$, —S(O)$_2$R$^{70}$, —S(O)$_2$O$^-$M$^+$, —S(O)$_2$OR$^{70}$, —OS(O)$_2$R$^{70}$, —OS(O)$_2$O$^-$M$^+$, —OS(O)$_2$OR$^{70}$, —P(O)(O$^-$)$_2$(M$^+$)$_2$, —P(O)(OR$^{70}$)O$^-$M$^+$, —P(O)(OR$^{70}$)(OR$^{70}$), —C(O)R$^{70}$, —C(S)R$^{70}$, —C(NR$^{70}$) R$^{70}$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O) OR$^{70}$, —OC(S)OR$^{70}$, —NR$^{70}$C(O)R$^{70}$, —NR$^{70}$C(S)R$^{70}$, —NR$^{70}$C(O)OR$^{70}$, —NR$^{70}$C(S)OR$^{70}$, —NR$^{70}$C(O) NR$^{80}$R$^{80}$, —NR$^{70}$C(NR$^{70}$)R$^{70}$ and —NR$^{70}$C(NR$^{70}$) NR$^{80}$R$^{80}$, where R$^{60}$, R$^{70}$, R$^{80}$ and M$^+$ are as previously defined.

In addition to the disclosure herein, in a certain embodiment, a group that is substituted has 1, 2, 3, or 4 substituents, 1, 2, or 3 substituents, 1 or 2 substituents, or 1 substituent.

Unless indicated otherwise, the nomenclature of substituents that are not explicitly defined herein are arrived at by naming the terminal portion of the functionality followed by the adjacent functionality toward the point of attachment. For example, the substituent "alkylaminocarbonylamino" refers to the group (alkyl)-NH—C(O)—NH—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

The term "pharmaceutically acceptable salt" means a salt which is acceptable for administration to a patient, such as a mammal (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

"Pharmaceutically effective amount" and "therapeutically effective amount" refer to an amount of a compound sufficient to elicit the desired therapeutic effect (e.g., treatment of a specified disorder or disease or one or more of its symptoms and/or prevention of the occurrence of the disease or disorder). In reference to polyglutamine diseases, a pharmaceutically or therapeutically effective amount includes an amount sufficient to, among other things, prevent or cause a reduction of proteinaceous deposits in the brain of a subject.

The term "salt thereof" means a compound formed when a proton of an acid is replaced by a cation, such as a metal cation or an organic cation and the like. Where applicable, the salt is a pharmaceutically acceptable salt, although this is not required for salts of intermediate compounds that are not intended for administration to a patient. By way of example, salts of the present compounds include those wherein the compound is protonated by an inorganic or organic acid to form a cation, with the conjugate base of the inorganic or organic acid as the anionic component of the salt.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

"Stereoisomer" and "stereoisomers" refer to compounds that have same atomic connectivity but different atomic arrangement in space. Stereoisomers include cis-trans isomers, E and Z isomers, enantiomers, and diastereomers.

"Tautomer" refers to alternate forms of a molecule that differ only in electronic bonding of atoms and/or in the position of a proton, such as enol-keto and imine-enamine tautomers, or the tautomeric forms of heteroaryl groups containing a —N=C(H)—NH— ring atom arrangement, such as pyrazoles, imidazoles, benzimidazoles, triazoles, and tetrazoles. A person of ordinary skill in the art would recognize that other tautomeric ring atom arrangements are possible.

By "linking" or "linker" as in "linking group," "linker moiety," etc., is meant a linking moiety that connects two groups via covalent bonds. The linker may be linear, branched, cyclic or a single atom. Examples of such linking groups include alkyl, alkenylene, alkynylene, arylene, alkarylene, aralkylene, and linking moieties containing functional groups including, without limitation: amido (—NH—CO—), ureylene (—NH—CO—NH—), imide (—CO—NH—CO—) , epoxy (—O—), epithio (—S—), epidioxy (—O—O—), epidithio (—S—S—), carbonyldioxy (—O—CO—O—), alkyldioxy (—O—(CH2)n—O—), epoxyimino (—O—NH—), epimino (—NH—), carbonyl (—CO—), etc. In certain cases, one, two, three, four or five or more carbon atoms of a linker backbone may be optionally substituted with a sulfur, nitrogen or oxygen heteroatom. The bonds between backbone atoms may be saturated or unsaturated, usually not more than one, two, or three unsaturated bonds will be present in a linker backbone. The linker may include one or more substituent groups, for example with an alkyl, aryl or alkenyl group. A linker may include, without limitations, poly(ethylene glycol) unit(s) (e.g., —(CH$_2$—CH$_2$—O)—); ethers, thioethers, amines, alkyls (e.g., (C$_1$-C$_{12}$)alkyl) , which may be straight or branched, e.g., methyl, ethyl, n-propyl, 1-methylethyl (iso-propyl), n-butyl, n-pentyl, 1,1-dimethylethyl (t-butyl), and the like. The linker backbone may include a cyclic group, for example, an aryl, a heterocycle or a cycloalkyl group, where 2 or more atoms, e.g., 2, 3 or 4 atoms, of the cyclic group are included in the backbone. A linker may be cleavable or non-cleavable. Any convenient orientation and/or connections of the linkers to the linked groups may be used.

It will be appreciated that the term "or a salt or solvate or stereoisomer thereof" is intended to include all permutations of salts, solvates and stereoisomers, such as a solvate of a pharmaceutically acceptable salt of a stereoisomer of subject compound.

In certain embodiments, a substituent may contribute to optical isomerism and/or stereo isomerism of a compound. Salts, solvates, hydrates, and prodrug forms of a compound are also of interest. All such forms are embraced by the present disclosure. Thus the compounds described herein include salts, solvates, hydrates, prodrug and isomer forms thereof, including the pharmaceutically acceptable salts, solvates, hydrates, prodrugs and isomers thereof. In certain embodiments, a compound may be metabolized into a pharmaceutically active derivative.

Unless otherwise specified, reference to an atom is meant to include isotopes of that atom. For example, reference to H is meant to include $^1$H, $^2$H (i.e., D) and $^3$H (i.e., T), and reference to C is meant to include $^{12}$C and all isotopes of carbon (such as $^{13}$C).

The terms "individual," "subject," "host," and "patient," used interchangeably herein, refer to an individual organism, e.g., a mammal, including, but not limited to, murines, simians, non-human primates, humans, mammalian farm animals, mammalian sport animals, and mammalian pets.

The term "treating" or "treatment" as used herein means the treating or treatment of a disease or medical condition in a patient, such as a mammal (particularly a human) that includes: (a) preventing the disease or medical condition from occurring, such as, prophylactic treatment of a subject; (b) ameliorating the disease or medical condition, such as, eliminating or causing regression of the disease or medical condition in a patient; (c) suppressing the disease or medical condition, for example by, slowing or arresting the development of the disease or medical condition in a patient; or (d) alleviating a symptom of the disease or medical condition in a patient.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a BAF complex modulating compound" includes a plurality of such BAF complex modulating compounds and reference to "the kinase inhibitor" includes reference to one or more kinase inhibitors and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. For all purposes in the United States and in other jurisdictions where effective, each and every publication and patent document cited in this disclosure is hereby incorporated herein by reference in its entirety for all purposes to the same extent as if each such publication or document was specifically and individually indicated to be incorporated herein by reference.

Definitions of other terms and concepts appear throughout the detailed description below.

Additional Embodiments

The present disclosure is also described by the following clauses.

Clause 1. A pharmaceutical composition comprising:
a BAF complex modulating compound of formula (IA):

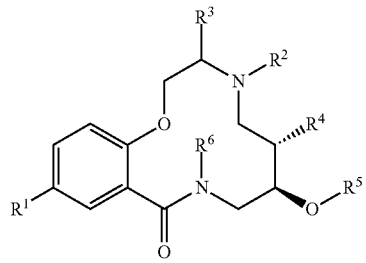

wherein:
$R^1$ is amine, substituted amine, alkylaminocarbonylamino, substituted alkylaminocarbonylamino, alkanoylamino, substituted alkanoylamino, arylaminocarbonylamino, substituted arylaminocarbonlamino, carbamate, substituted carbamate, aroylamino or substituted aroyl amino;

$R^2$ is heteroaryl-aryl-alkyl, substituted heteroaryl-arylalkyl, aryl-heteroaryl-alkyl, substituted aryl-heteroaryl alkyl, alkanoyl or substituted alkanoyl;

$R^3$ to $R^6$ are each independently H, alkyl or substituted alkyl;

or a pharmaceutically acceptable salt thereof; and
a pharmaceutically acceptable excipient.

Clause 2. The pharmaceutical composition of clause 1, wherein $R^1$ is selected from:

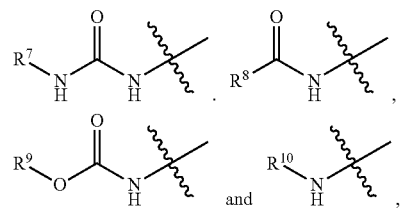

wherein:
$R^7$, $R^8$ and $R^9$ are each independently selected from, alkyl, substituted alkyl, aryl, substituted aryl, heteroaryl, substituted heteroaryl, cycloalkyl, substituted cycloalkyl, heterocycle, substituted heterocycle; and $R^{10}$ is selected from H, alkyl, substituted alkyl, aryl, subsitututed aryl, heteroaryl, substituted heteroaryl, cycloalkyl, substituted cycloalkyl, heterocycle and substituted heterocycle.

Clause 3. The pharmaceutical composition of clause 2, wherein $R^1$ is selected from:

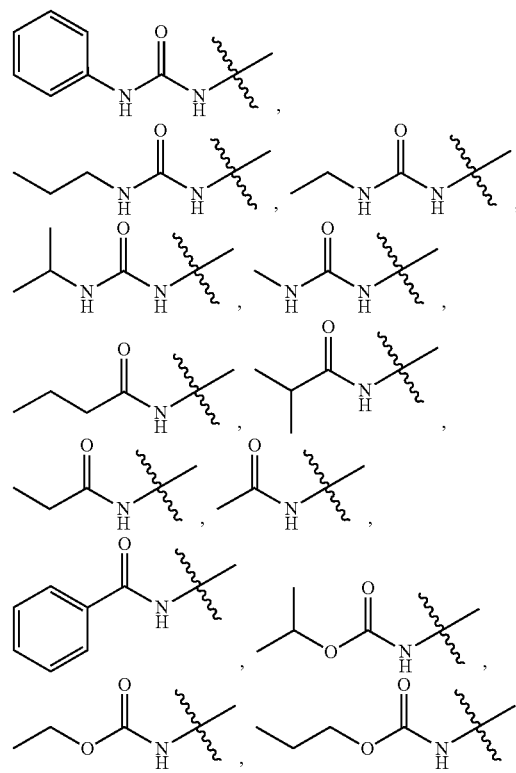

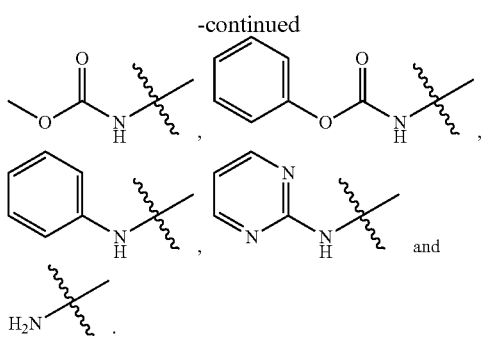

Clause 4. The pharmaceutical composition of any one of clauses 1 to 3, wherein $R^2$ is of the formula:

-$L^1$-Z (IC); or

-$L^2$-C(O)-$L^3$-$R^{11}$ (ID)

wherein:
$L^1$ is an alkyl linker or a substituted alkyl linker;
$L^2$ and $L^3$ are each independently selected from a covalent bond, an alkyl linker and a substituted alkyl linker;
Z is heteroaryl-aryl, substituted heteroaryl-aryl, aryl-heteraryl or substituted heteroaryl-aryl; and
$R^{11}$ is alkyl, substituted alkyl, $C_{3-10}$ cycloalkyl, substituted $C_{3-10}$ cycloalkyl, $C_{3-10}$ heterocycle or substituted $C_{3-10}$ heterocycle.

Clause 5. The pharmaceutical composition of any one of clauses 1 to 4, wherein $R^2$ is selected from:

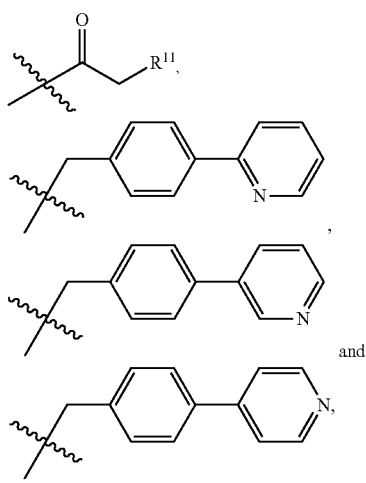

wherein:
$R^{11}$ is alkyl group, substituted alkyl group, $C_{3-10}$ cycloalkyl, substituted $C_{3-10}$ cycloalkyl, $C_{3-10}$ heterocycle or substituted $C_{3-10}$ heterocycle.

Clause 6. The pharmaceutical composition of clause 5, wherein $R^2$ is:

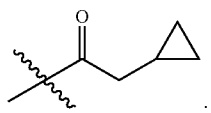

Clause 7. The pharmaceutical composition of clause 5, wherein $R^2$ is:

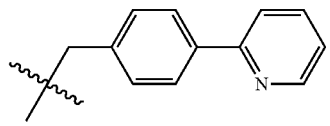

Clause 8. The pharmaceutical composition of any one of clauses 1 to 7, wherein each of $R^3$, $R^4$, $R^5$ and $R^6$ are lower alkyl or substituted lower alkyl.

Clause 9. The pharmaceutical composition of clause 8, wherein each of $R^3$, $R^4$, $R^5$ and $R^6$ are methyl groups.

Clause 10. The pharmaceutical composition of any one of clauses 1 to 9, wherein the compound is of formula (II):

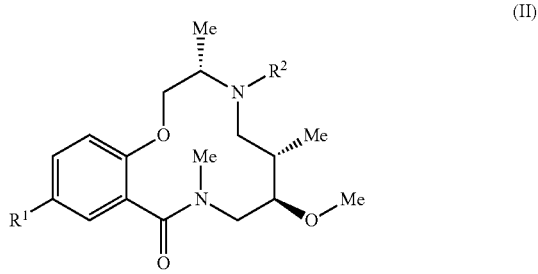

(II)

wherein:
$R^1$ is

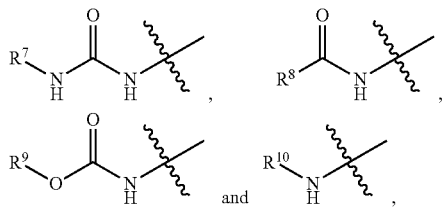

wherein:
$R^7$, $R^8$ and $R^9$ are each independently selected from, methyl, ethyl, propyl, isopropyl, butyl, sec-butyl, tert-butyl, pentyl, hexyl, aryl, substituted aryl, heteroaryl, substituted heteroaryl, cycloalkyl, substituted heteroraryl, heterocycle, substituted heterocycle; and
$R^{10}$ is selected from H, alkyl, substituted alkyl, aryl, subsitututed aryl, heteroaryl, substituted heteroaryl, cycloalkyl, substituted cycloalkyl, heterocycle and substituted heterocycle; and
$R^2$ is selected from

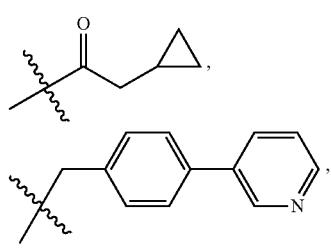

-continued

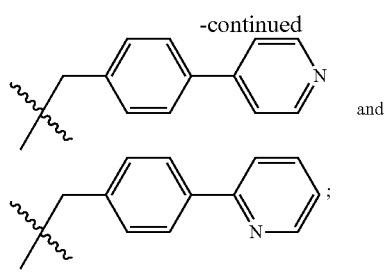

or a pharmaceutically acceptable salt thereof.

Clause 11. The pharmaceutical composition of clause 10, wherein the compound is of formula (III):

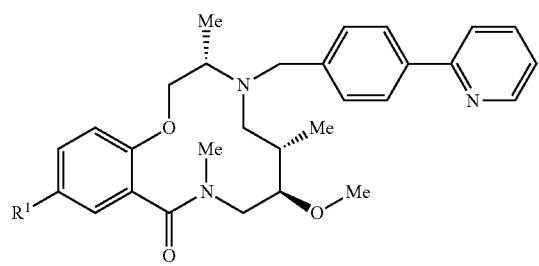

wherein:

$R^1$ is

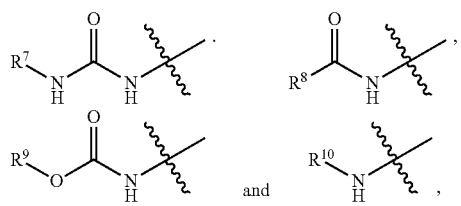

wherein:

$R^7$, $R^8$ and $R^9$ are each independently selected from, methyl, ethyl, propyl, isopropyl, butyl, sec-butyl, tert-butyl, penyl, hexyl, aryl, substituted aryl, heteroaryl, substituted heteroaryl, cycloalkyl, heteroaryl, substituted heterocycle;

or a pharmaceutically acceptable salt thereof.

Clause 12. The pharmaceutical composition of clause 10 or 11, wherein $R^1$ is selected from:

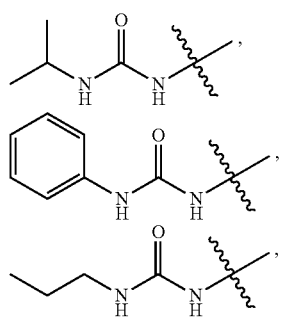

-continued

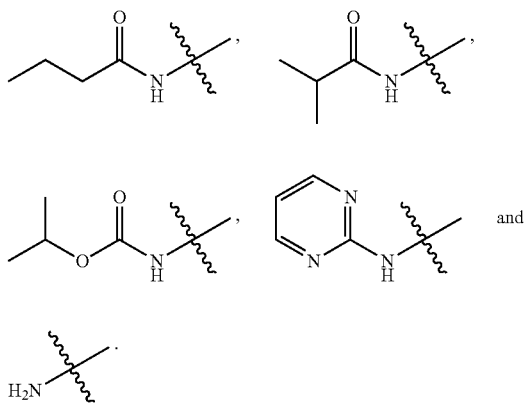

Clause 13. The pharmaceutical composition of any one of clauses 1 to 10, wherein the compound has a structure selected from:

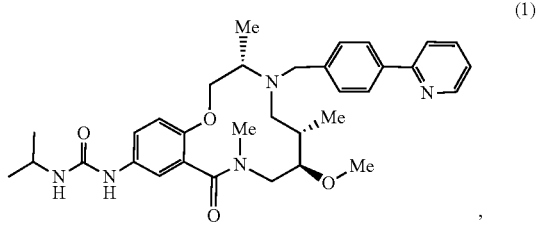
(1)

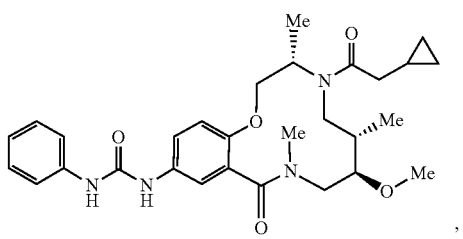
(2)

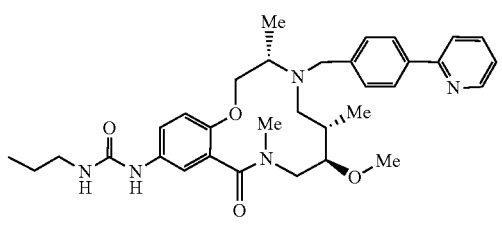
(3)

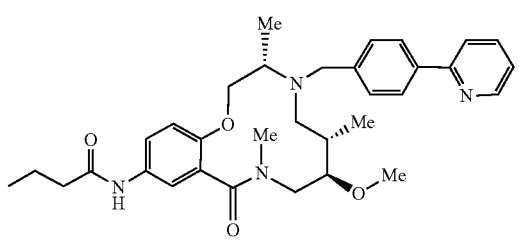
(4)

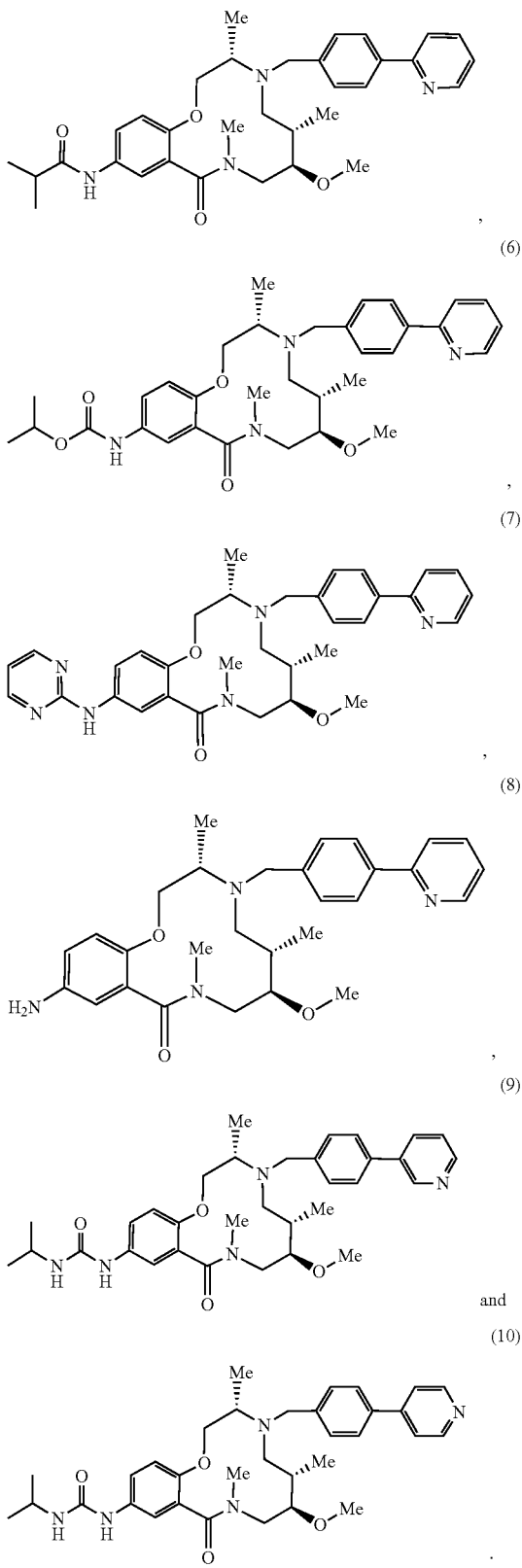

Clause 14. The pharmaceutical composition of any one of clauses 1 to 13, wherein the compound has the structure:

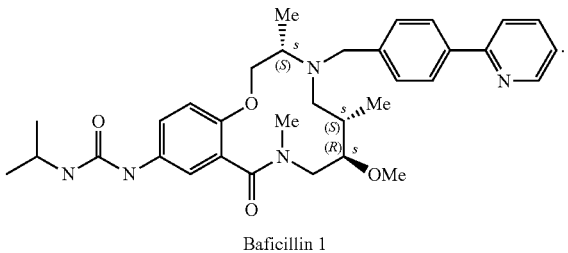

Baficillin 1

Clause 15. A method of modulating a BAF complex in a cell, the method comprising:
  contacting a cell comprising a BAF complex with a BAF complex modulating compound of any one of clauses 1-14 to modulate the activity of a BAF complex in the cell.

Clause 16. The method of clause 15, wherein modulating the activity of the BAF complex comprises inhibiting an activity of the BAF complex.

Clause 17. The method of clause 16, wherein inhibiting the activity of the BAF complex comprises blocking a de-repressive function of the BAF complex in the cell.

Clause 18. The method of clause 16, wherein inhibiting the activity of the BAF complex comprises activating BAF complex-repressed genes Clause 19. The method of clause 16, wherein inhibiting the activity of the BAF complex comprises activating Polycomb complex-repressed genes.

Clause 20. The method according to any one of clauses 15 to 19, wherein the cell is in vivo.

Clause 21. The method according to any one of clauses 15 to 19, wherein the cell is in vitro.

Clause 22. A method of treating cancer, the method comprising:
  co-administering to a subject with cancer:
    a therapeutically effective amount of a pharmaceutical composition according to any one of clauses 1-14; and
    an ATR inhibitor;
  to treat the subject for cancer.

Clause 23. The method of clause 22, wherein the subject has cancer cells having a ARID1A-containing BAF complex and administration of the BAF complex modulating compound sensitizes the cancer cells to inhibition of ATR kinase.

Clause 24. The method of clause 22 or 23, wherein the cancer is a highly mutated cancer and the pharmaceutical composition and the ATR inhibitor act synergistically to kill cancer cells of the subject.

Clause 25. The method of clause 24, wherein the synergistic action allows a reduction in the effective dose of the ATR inhibitor to an amount below a threshold of toxicity.

Clause 26. The method of clause 22, wherein the subject has cancer cells harboring a BAF complex mutation.

Clause 27. A method of treating a BRCA1 cancer, the method comprising:
  administering to a subject with a BRCA1 cancer a therapeutically effective amount of a pharmaceutical composition according to any one of clauses 1-14 to treat the BRCA1 cancer.

Clause 28. The method of any one of clauses 22-27, wherein the cancer is Breast Cancer, Prostate Cancer, Pancreatic Cancer, Lung Cancer, Colon Cancer, Ovarian Cancer, Liver Cancer, Melanoma, Renal Cancer, Central Nervous System Cancer, or Leukemia Lymphoma.

EXAMPLES

Example 1: Inhibition of the SWI/SNF Complex as a Synthetic Lethal Therapy of Cancer through Synergy with ATR Inhibitors.

Summary

Human SWI/SNF (BAF) complexes are a diverse family of ATP-dependent chromatin remodelers that exhibit combinatorial specificity to regulate specific genetic programs[1-6]. SWI/SNF complexes regulate transcription, replication and DNA repair through a variety of mechanisms including nucleosome mobilization, polycomb opposition, and Top2-mediated decatenation[4,7-11]. Subunits of the BAF complex are mutated in about 20% of human cancers and a large number of neurologic diseases[12-15]. Here we show that a molecule, Baficilin1, discovered in a screen for mammalian SWI/SNF inhibitors[16] functions synergistically with inhibitors of the ATR/ATM kinase, which are under investigation for treatment of a broad group of human cancers. Since Baficilin1 is not detectably toxic, these studies suggest an avenue for therapeutic enhancement of ATR/ATM inhibition without additional toxicity.

Introduction

BAF complexes play an essential role in the regulation of enhancers and promoters[17,18] and oppose polycomb repressive complexes by direct, ATP-dependent eviction of PRC1[11] and facilitation of Topo resolution of heterochromatin[9]. To date, only two inhibitors of the SMARCA4 (Brg1) ATPase subunit have been reported (FIG. 1a)[19-21]. The first, PFI-3, targets the bromodomains of Brg1 and Brm, and has been shown to have no measureable effects on inhibiting the growth of cancer cells[19,22]. The second is a phosphor-aminoglycoside which inhibits the yeast SWI2/SNF2 complex but has limited utility in mammalian cells and is a relatively non-specific, broad-spectrum ATPase inhibitor[21].

Activation of the ATR kinase (Ataxia-Telangiectasia Mutated and Rad3-related protein kinase) is required for initiating the replication stress response and the associated DNA damage cell cycle checkpoint[23,24]. As such, inhibitors of ATR, which are currently in Phase I-II clinical trials, have been shown to enhance the chemotoxic effects of DNA damaging agents[25,26]. In addition, potent small molecule inhibitors of ATR have recently been shown to induce a synthetic lethal function in cancer cell lines deficient in the ARID1A subunit of the BAF complex. This synthetic lethal interaction has been attributed to the increased dependency of ARID1A-deficient cells on the ATR-mediated G2/M decatenation checkpoint following loss of ARID1A-mediated interactions of the BAF complex with TOP2A[7,27]. Utilizing the knowledge that one of the BAF complex's diverse and essential functions involves repression of specific genes in embryonic stem cells[28], we developed a screening strategy to identify compounds that upregulate target genes repressed by the embryonic BAF complex (esBAF) in mESCs including Bmi1, Ring1, and Fgf4 (FIG. 1b)[16,29]. Given that the loss of ARID1A (a functionally critical, mechanistically elusive, and frequently mutated subunit of the BAF complex) sensitizes cancer cells to inhibition of the ATR kinase, we sought to identify whether our putative esBAF inhibitors (FIG. 1c) might phenocopy the loss of ARID1A in cancer cells and thereby synergize with ATR inhibitors. Utilizing the Chou-Talalay method of synergy assessment (FIG. 1d), we demonstrate a synergistic hyper-synthetic-lethality in highly mutated cancers through acquired DNA damage, and provide a first-in-kind validation for the development of chemical probes targeting SWI/SNF complexes as cancer therapeutics.

Results

BAF Complex Inhibition Sensitizes Cancer Cells to ATRi

Figure 1A:
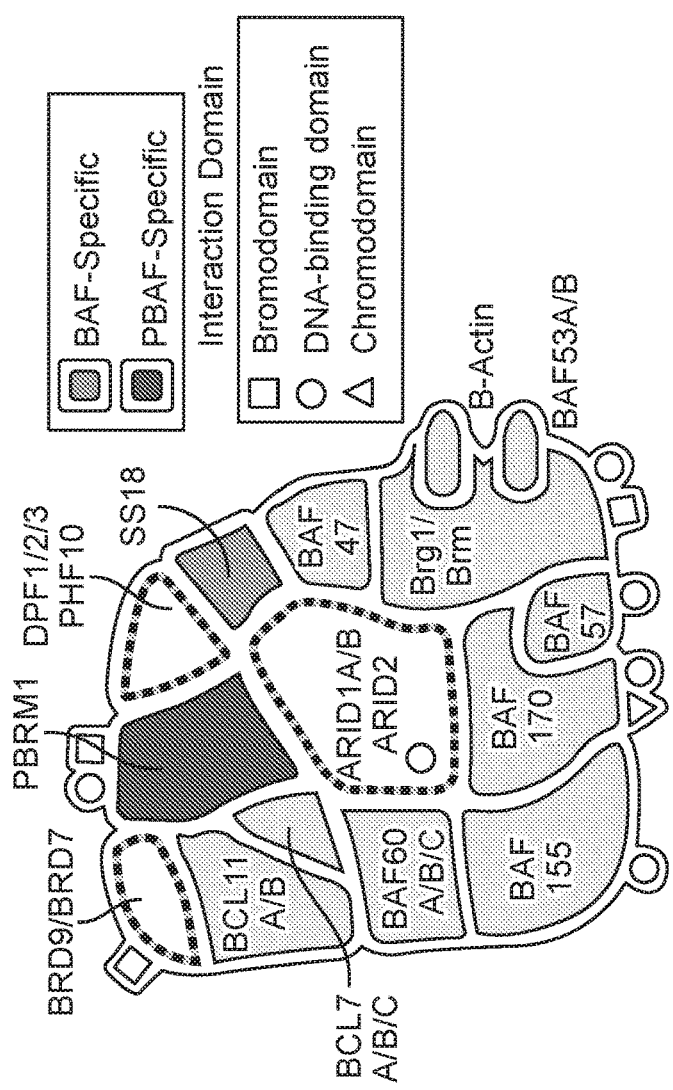
Figure 1C:
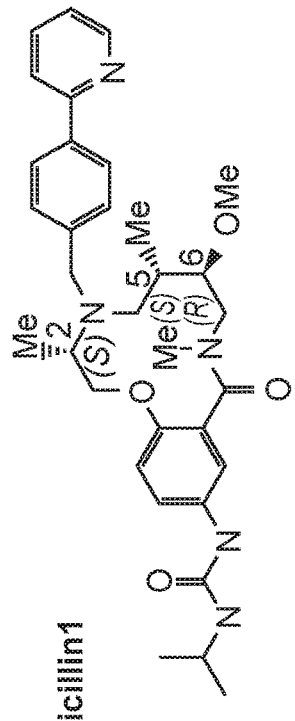

We recently completed a large-scale screen to identify small molecules that result in increased expression of Bmi1, a known genetic target of BAF whose expression is increased about 6- to 12-fold upon deletion of the SMARCA4 ATPase subunit of the BAF complex[29]. Of the initial hits, multiple 12-membered macrocyclic candidates were detected from a library of diversity-oriented-synthesis[30] molecules which exhibited stereospecificity and provided insight into a structure-activity-relationship[29]. While many of the molecules we detected blocked cell cycle progression and had toxic effects[29], (as might be expected from a general inhibitor of the BAF complex) one molecule was both non-toxic and exhibited robust activation of Bmi1 as well as other BAF targets, suggesting that it inhibited selective functions of the large 15-subunit BAF complex. This molecule, which we call Baficillin1 (FIG. 1c) was selected for further analysis for synergy with the ATR inhibitor VE-821 on the viability of the HCT116 colorectal cancer cell line, which contains an intact BAF complex (FIG. 1a). We loosely refer to Baficillin1 as a BAF inhibitor (BAFi) although we have not yet validated direct binding to BAF due to the biochemical limitations of purifying functional multi-subunit BAF complexes and the relatively low IC50 of Baficillin1. Previous studies showed that upon deletion of ARID1A, the IC50 of VE-821 in HCT116 cells shifted from ~10 uM to ~1 uM after 5 days of treatment[27]. In this study, HCT116 cells were treated with increasing doses of VE-821 (1 uM-50 uM) and increasing doses of BAFi (1 uM-30 uM) independently for 5 days to establish the respective dose responses of the two. Then, cells were treated with all possible combinations of 5 doses of both VE-821 (1.25-20 uM) and Baficillin1 (1.25-20 uM) for a total of 25 total combinations (FIG. 2b). By simultaneously treating HCT116 cells with increasing concentrations of VE-821 and a putative BAF inhibitor, we observed dose-responsive decreases in VE-821 IC50s ranging from ~4 uM at the lowest dose of BAFi (1.25 uM) to an IC50 ~1 uM at the highest dose tested in combination (FIG. 2b). This indicated that co-inhibition of both BAF and ATR could phenocopy the dose-response shift previously observed by ARID1A knockdown in HCT116 cells.

Combination BAFi/ATRi Treatment is Synergistic

Figure 1D:
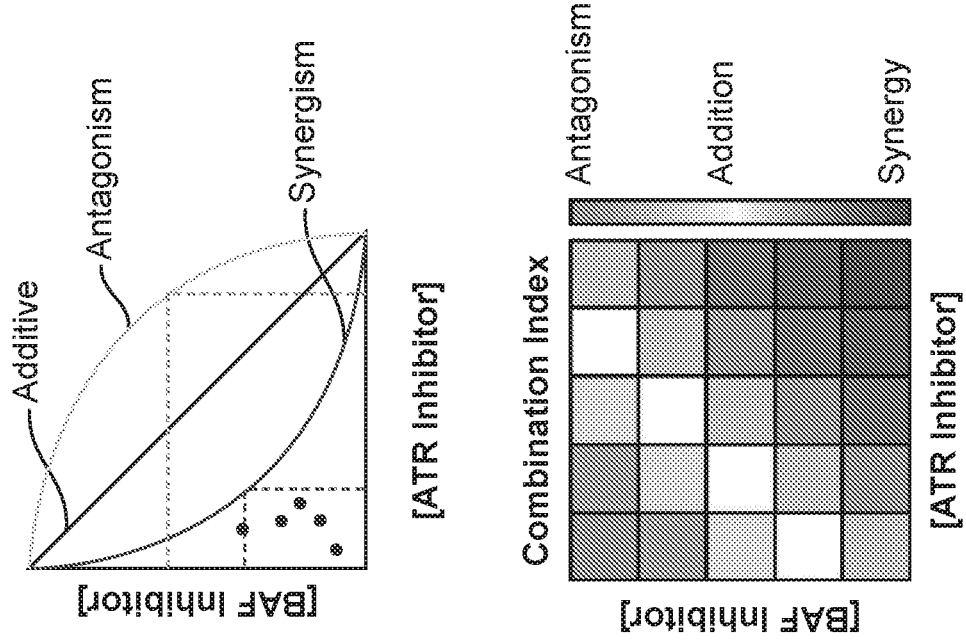
Figure 2E:
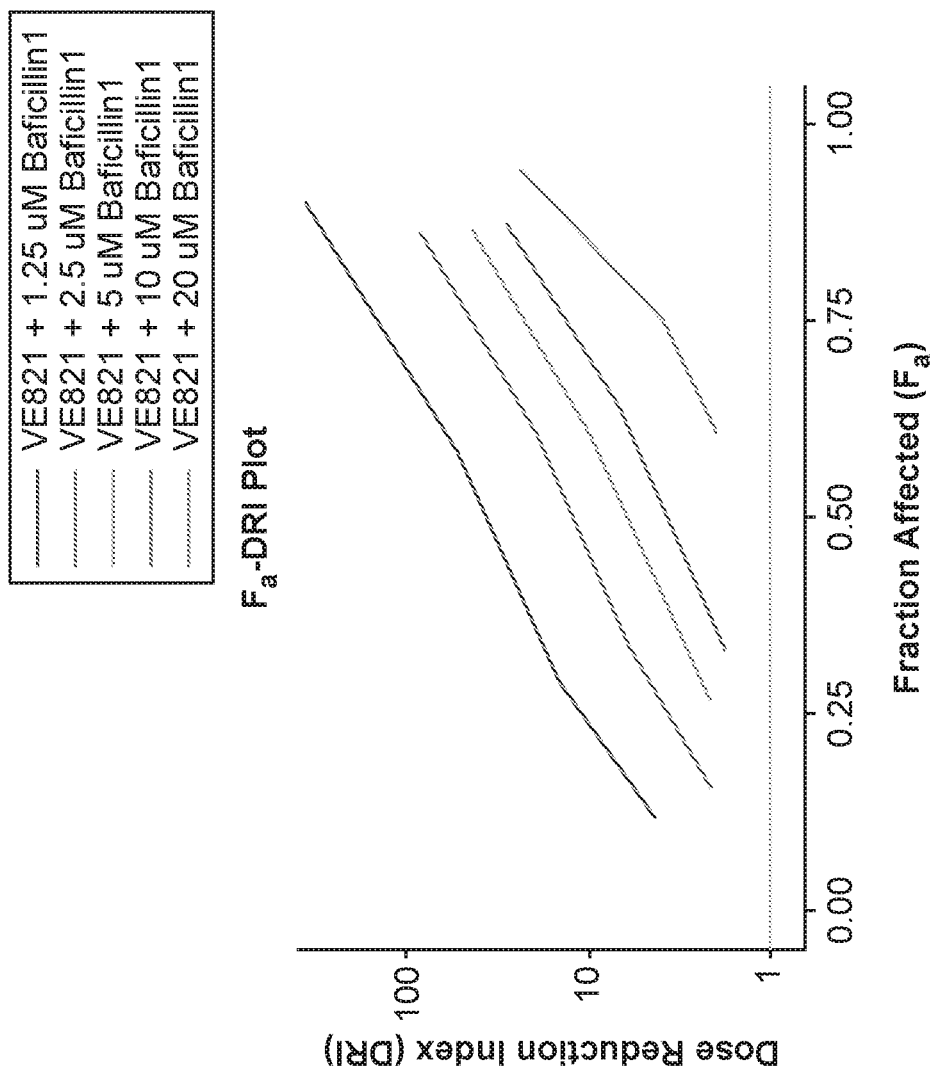
FIG. 2 shows that BAF and ATR inhibition is synergistic.
Figure 2D:
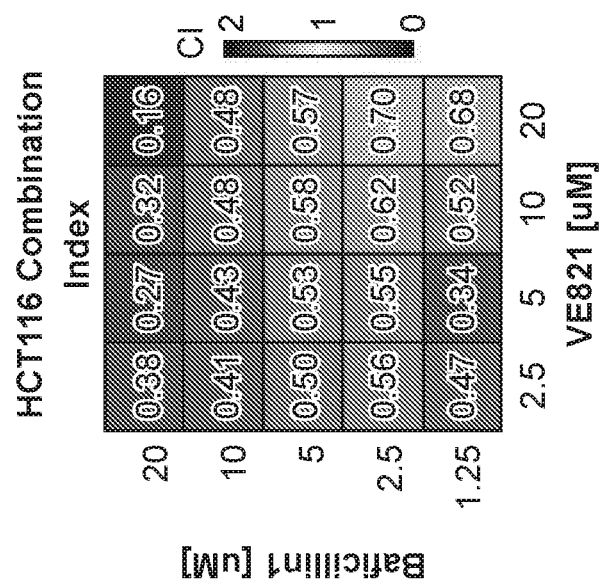

Often, combining two drugs with similar effects will result in enhanced potency. To assess whether the combined affect is greater than the predicted individual potencies, and hence true synergy, required a rigorous quantitative analysis of both the independent and combined effects of the two molecules, through the generation of isobolograms and quantification of a combination index (FIG. 1d). Synergism in drug combinations allows for the use of lower doses of both molecules, which can reduce adverse effects. As a result, drug combination pairs are often highly sought after strategies used in the treatment of cancer. We first aimed to validate that the combination of VE-821 and BAFi for synergistic therapeutic value. To assess drug synergy, the Chou-Talalay method was employed to provide a mechanism-independent method to quantify the synergism of drug interactions. This method combines elements of the Scatchard, Michaelis-menten, Hill, and Henderson-Hasslebalch equations through the law of mass-action[31,32] to generate a quantifiable assessment of synergy. Molecules were tested both independently and then in 25 different combinations in HCT116 cells for 5 days as described above. To determine a combination index (CI), median-effect equations of the two respective molecules were determined from their respective dose responses. The median-effect equation was used to calculate a median-effect dose, and $(Dx)_{ATRi,BAFi}$ values which correspond for the respective doses of the BAFi and ATRi compounds and correlate with a given percentage of cells affected by the individual treatments. Normalized index values ($I_{ATRi}$, $I_{BAFi}$), and the combination index are a ratio between the treatment dose, and the Dx for a given fraction of affected cells. Combination indices less than 0.9 are considered synergistic, while values ranging from 0.9 to 1.1 are additive, and CIs above 1.1 are antagonistic. Combination index values were calculated for the tested dose combinations of VE-821 and BAFi (FIG. 2d). The average combination index observed in HCT116 cells was 0.53±0.05 which indicates clear synergism between the inhibition of ATR and Baficillin1 (FIG. 2d). Further, the dose reduction index (an inverse relation to the combination index) was calculated to demonstrate that at low concentrations, the combination of VE-821 and Baficillin1 can reduce the dosing over 10-fold, while at higher concentrations, the dosing can be reduced upwards of 100-fold (FIG. 2e).

Putative BAF Inhibitor Phenocopies ARID1A Knockdown

Figures 3A, 3B:
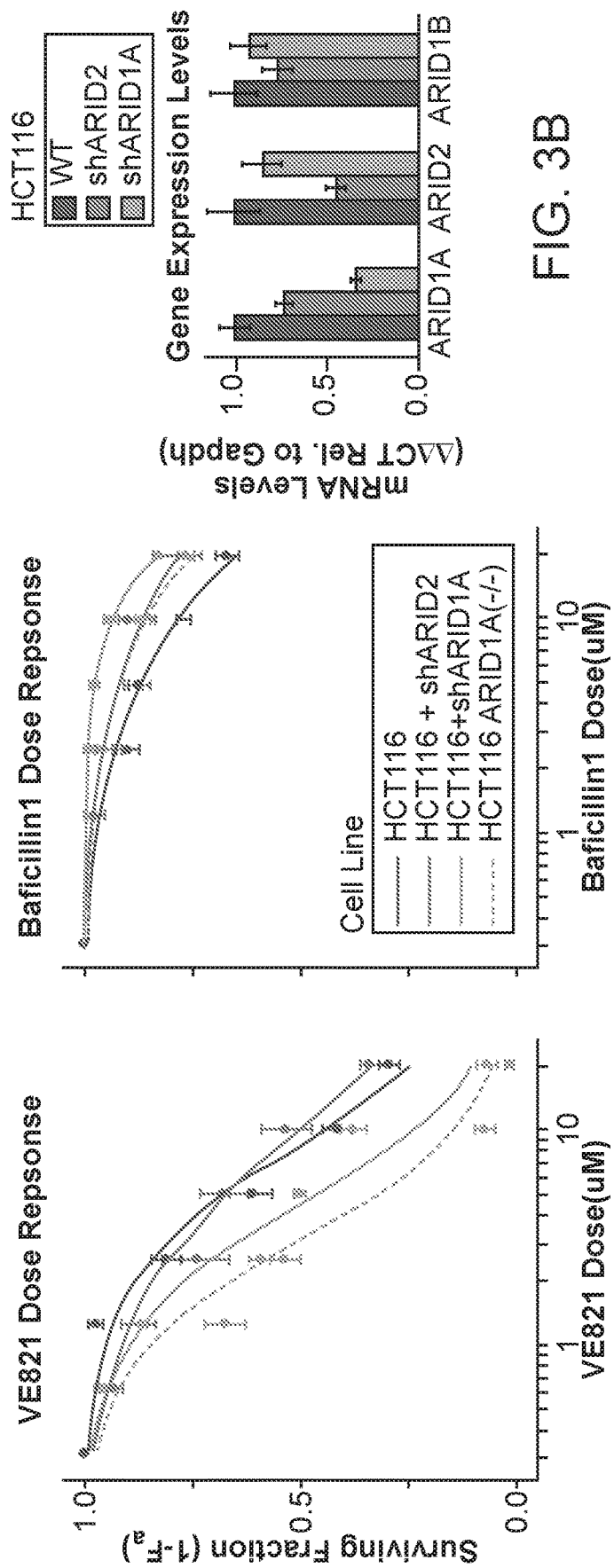
FIG. 3 shows putative BAF Inhibitor, Baficillin1 phenocopies knockdown of ARID1A.
Figures 3C, 3D:
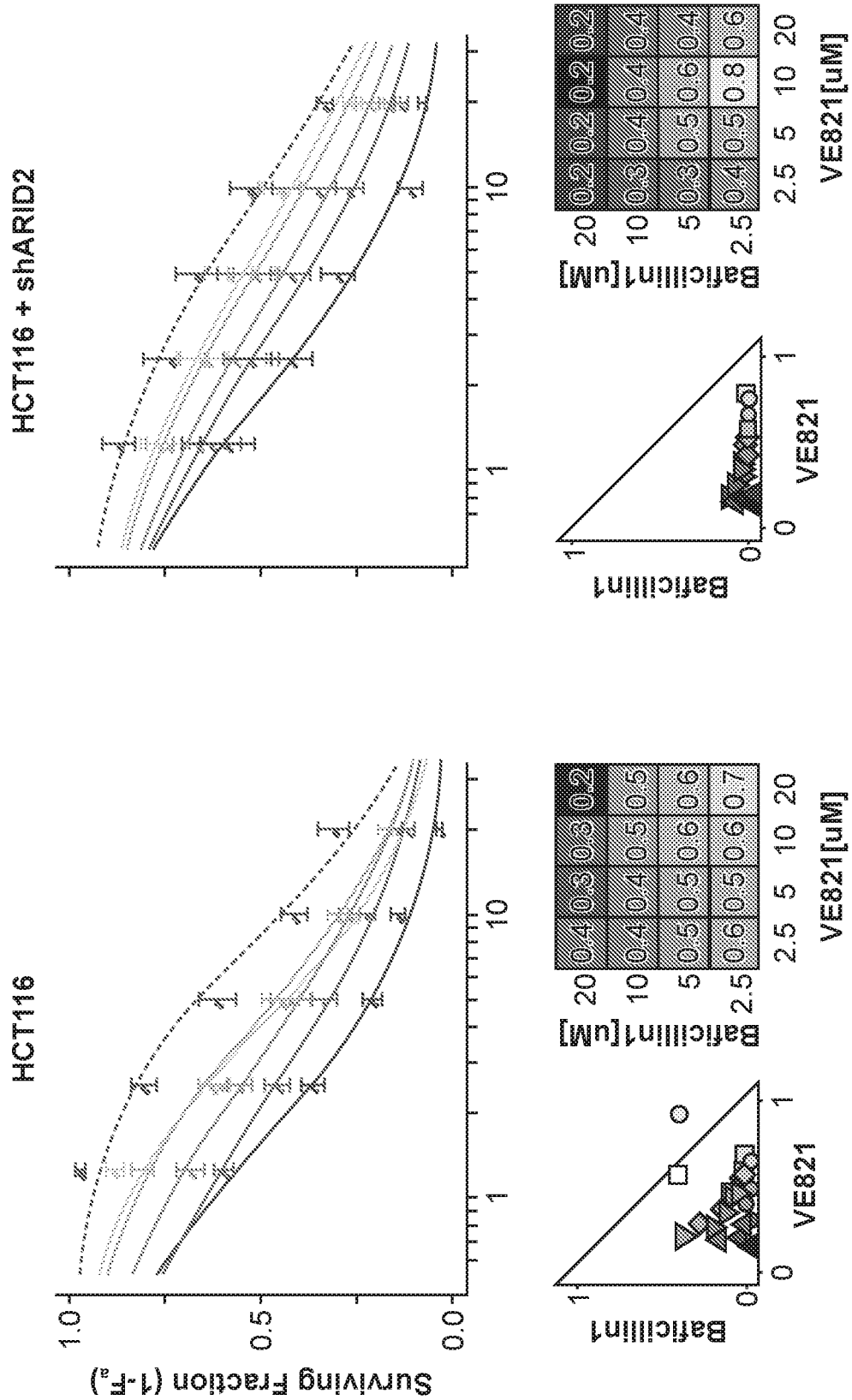
Figure 3F:
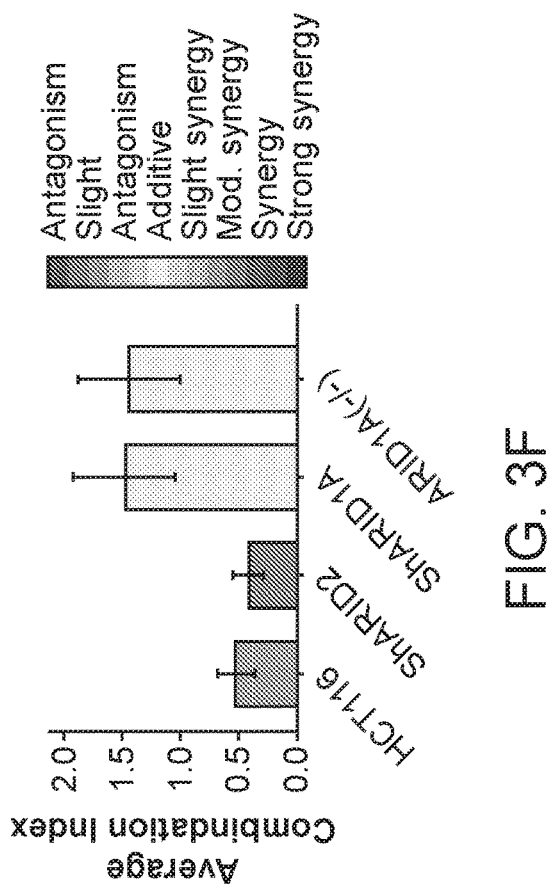
Figure 3E:
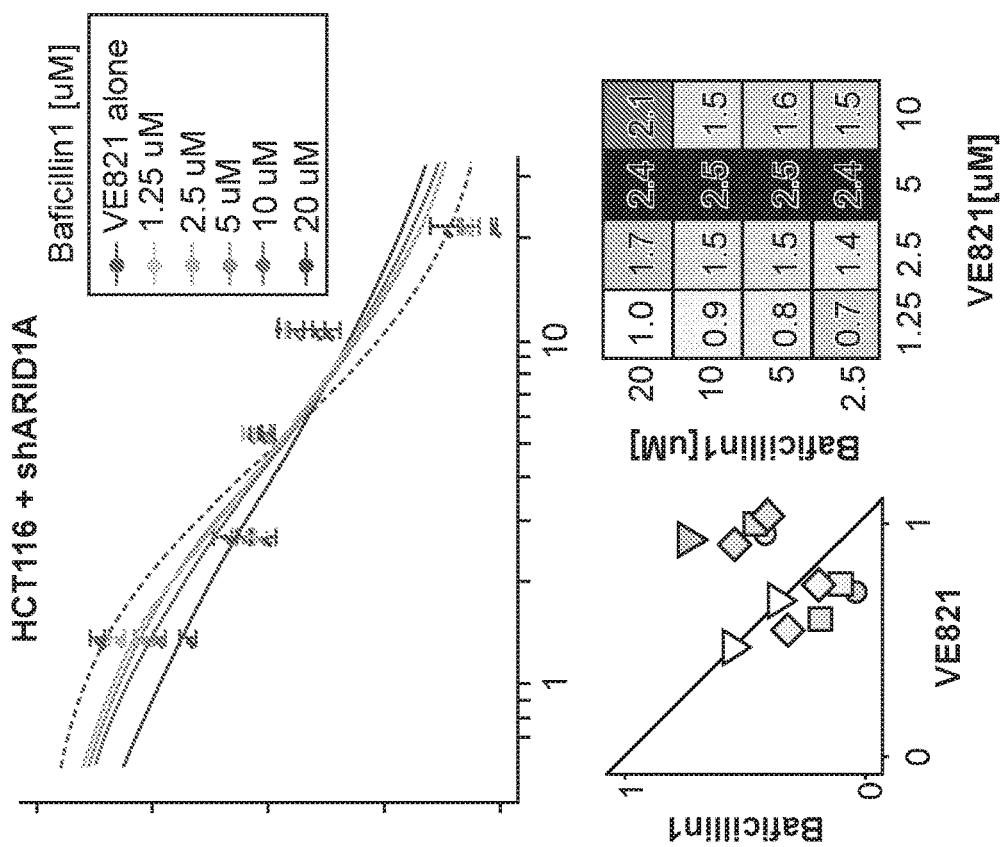
Figure 7:
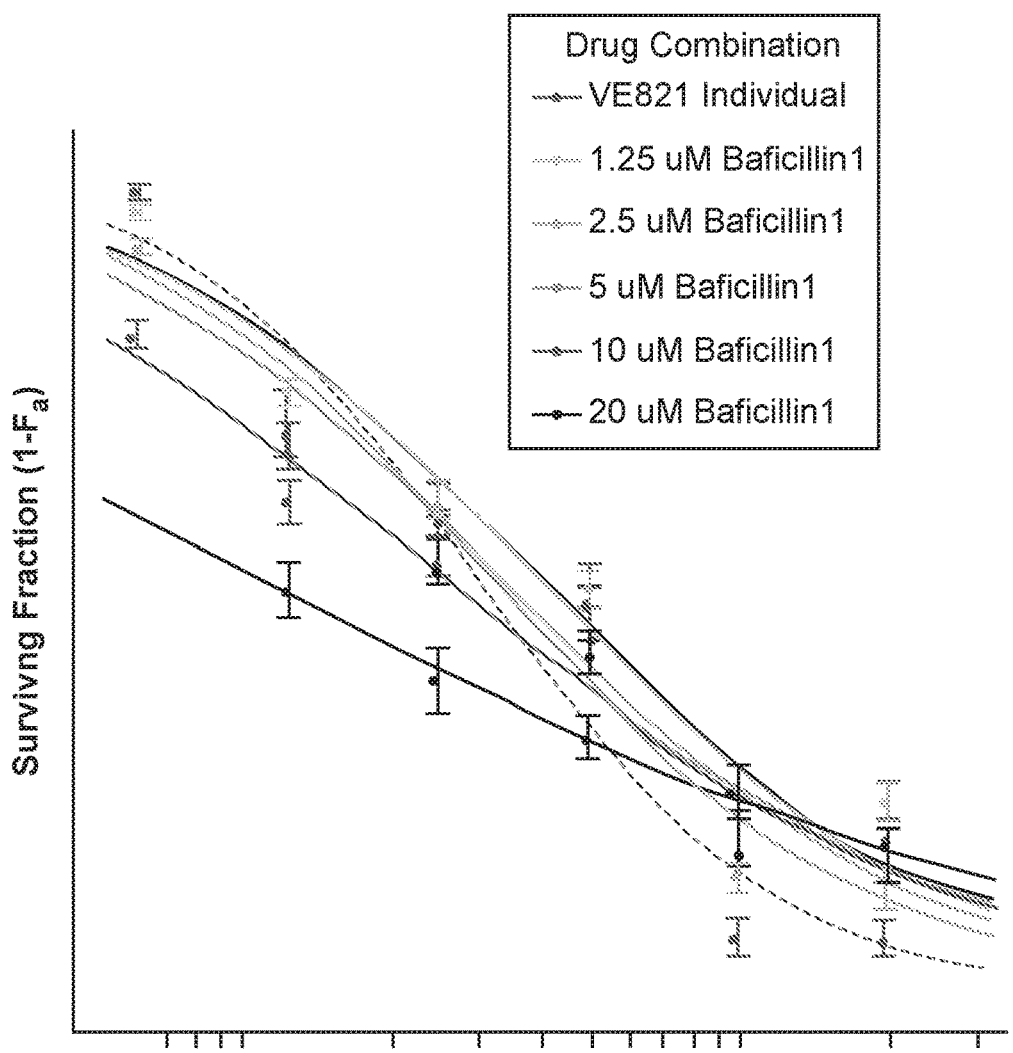
FIG. 7 shows the homozygous loss-of-function HCT116 (ARID1A−/−) cell line (CI−/−=1.44±0.12) which demonstrated slightly antagonistic effects.
Figure 7:
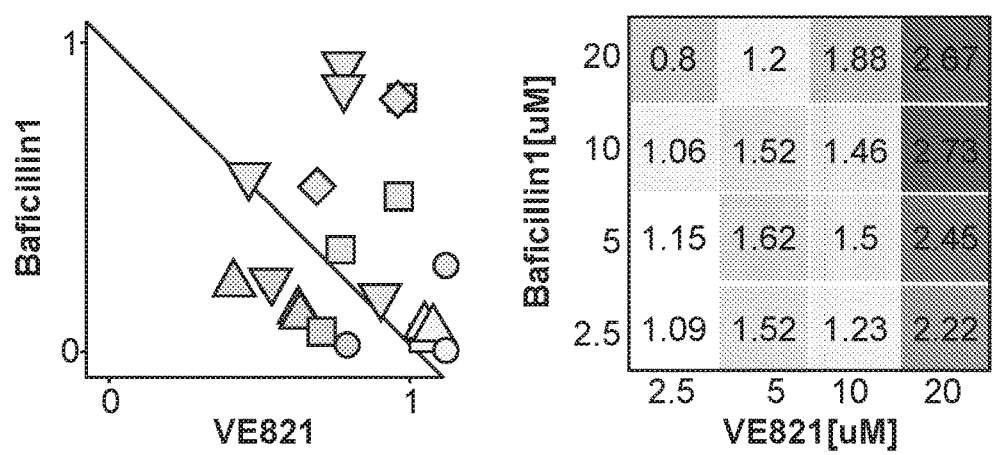

SMARCA4, the primary target of our original screen, is present in both human BAF and PBAF complexes in cancer[12]. PBAF complexes differ from BAF complexes by incorporation of specific subunits. Specifically, PBAF complexes contain ARID2 (as opposed to ARID1A/B), PHF10 (BAF45a) (as opposed to DPF10 (BAF45d)), PBRM1, and lack the BAF-specific subunit SS18. PBAF specific subunits are also frequently mutated in cancer, specifically renal clear cell carcinomas and cholangiocarcinomas[33-36]. To assess whether the lead compound is targeting BAF, PBAF complexes, or both, we constitutively knocked down ARID1A or ARID2 by lentiviral transduction of HCT116 cells and compared the BAFi/ATRi synergy to the wild-type (ARID1A+/+). Cells treated with shARID1A, demonstrated increased sensitivity to VE-821 as expected, as did the homozygous loss-of-function ARID1A HCT116 (ARID1A−/−) cell line which contains mutations p.Q456*/p.Q456*, while shARID2 cells responded to ATR treatment similar to wildtype cells (FIG. 3a). In contrast, both shARID1A and ARID1A-1-cells were slightly less sensitive to Baficillin1 than wild-type HCT116 cells. Further, upon knockdown of ARID1A or ARID2 (FIG. 3b), the synergistic effect observed between Baficillin1 and VE-821 was ablated upon loss of ARID1A (FIG. 3e) ($CI_{shARID1A}$=1.48±0.14), but not loss of shARID2 ($CI_{shARID2}$=0.42±0.04) (FIG. 3c-e). This result was further confirmed using the homozygous loss-of-function HCT116 (ARID1A−/−) cell line (CI−/−=1.44±0.12) which demonstrated slightly antagonistic effects, respectively (FIG. 3f, FIG. 7). This result suggests that that this putative BAF inhibitor is specifically targeting ARID1A-containing BAF complexes or specific sub-units and functions of such complexes.

Structure Activity Analysis of Putative BAF inhibitor

Figure 4A:
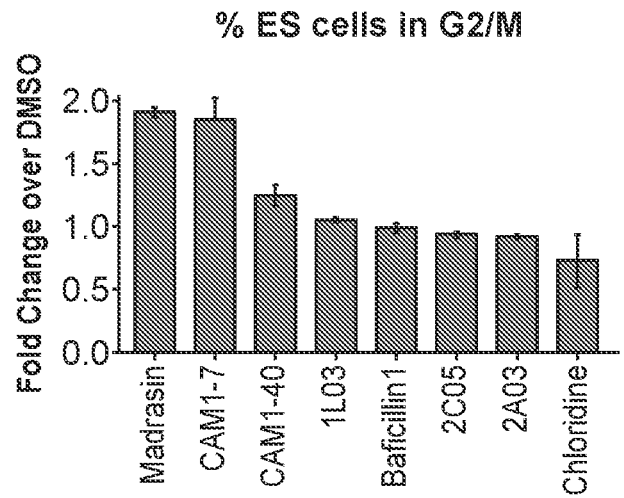
FIG. 4 illustrates a structure Activity Relationship of Putative BAF Inhibitors.
Figure 4B:
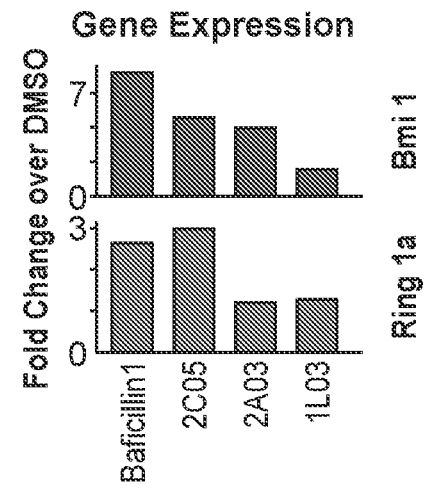
Figure 4C:
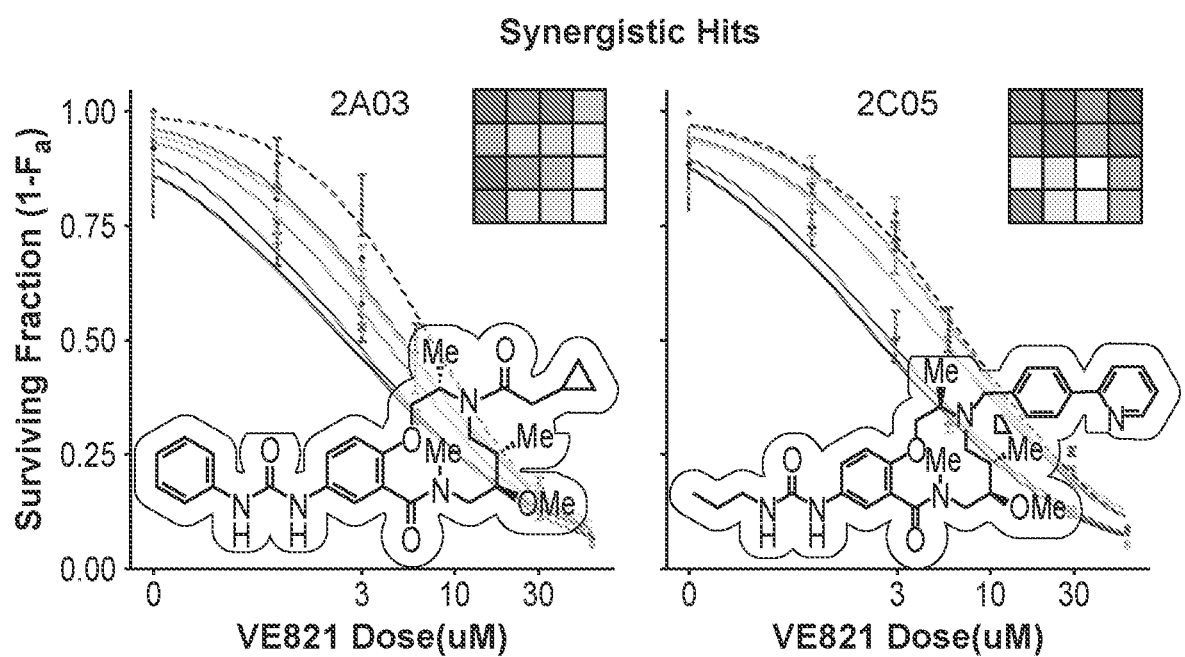
Figure 4E:
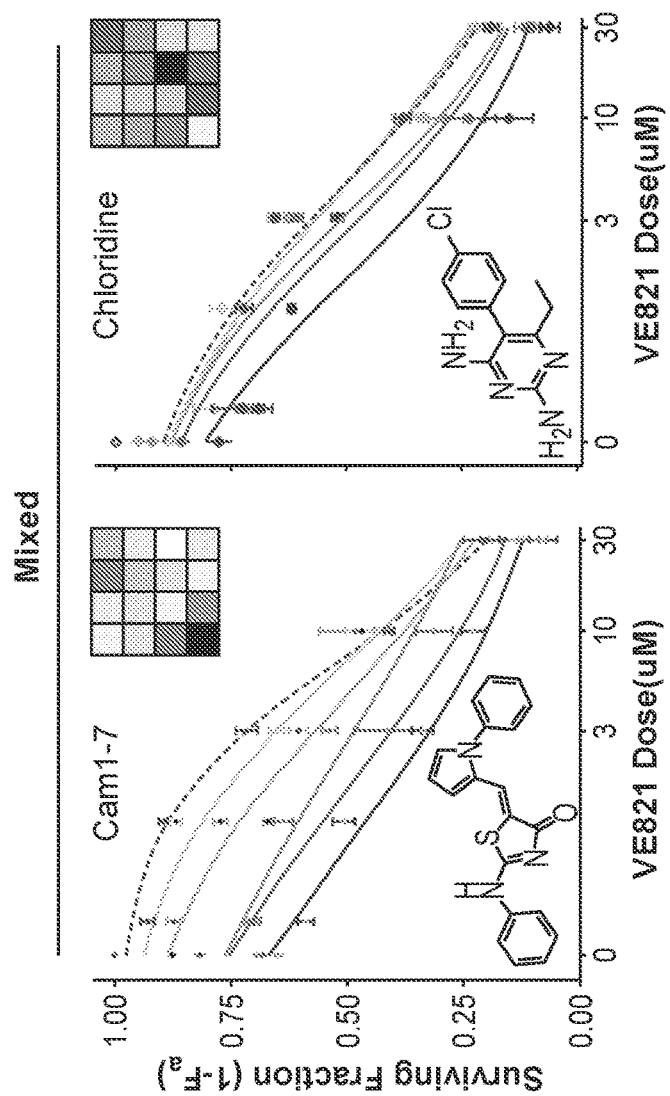
Figure 4D:
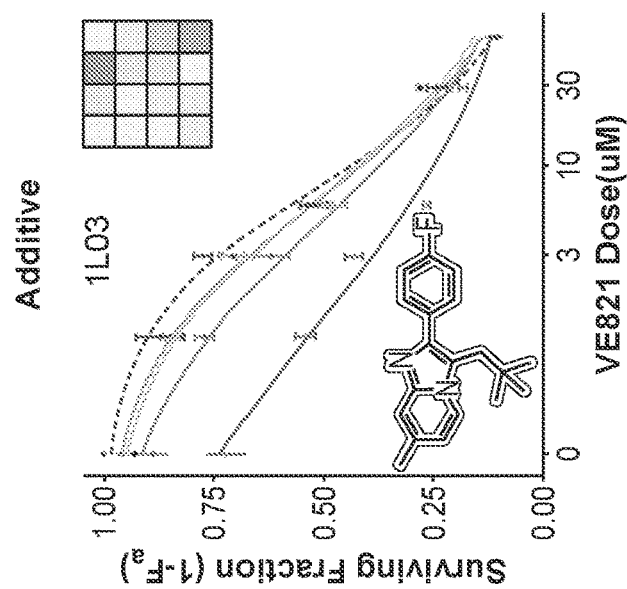
Figure 4F:
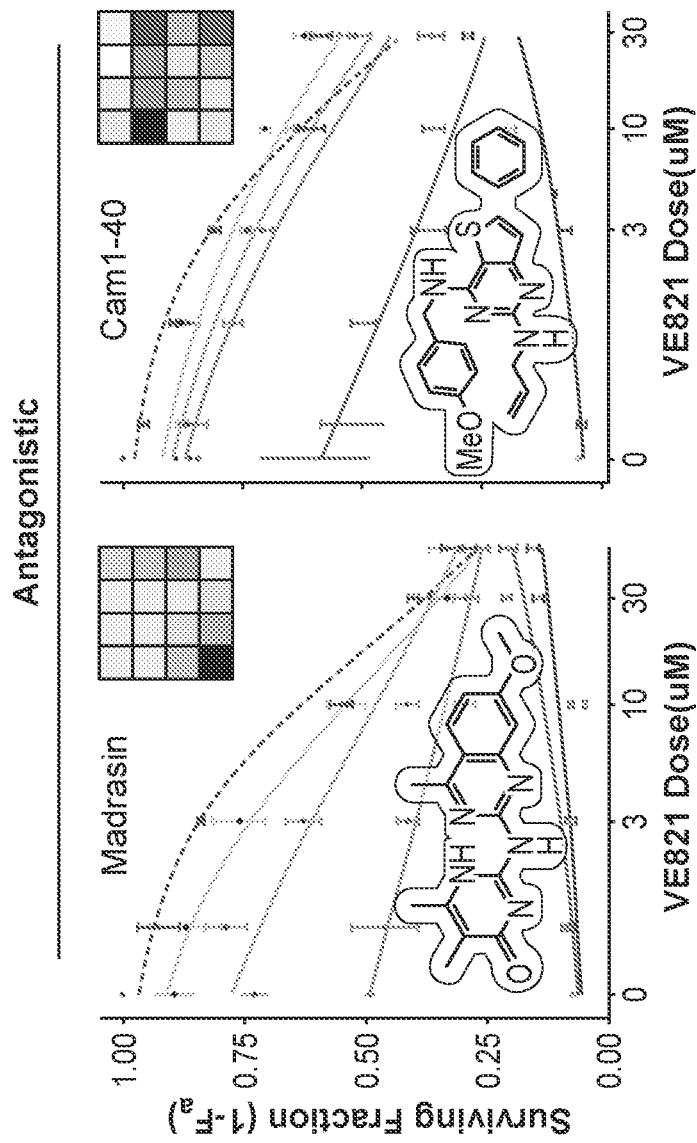
Figure 4G:
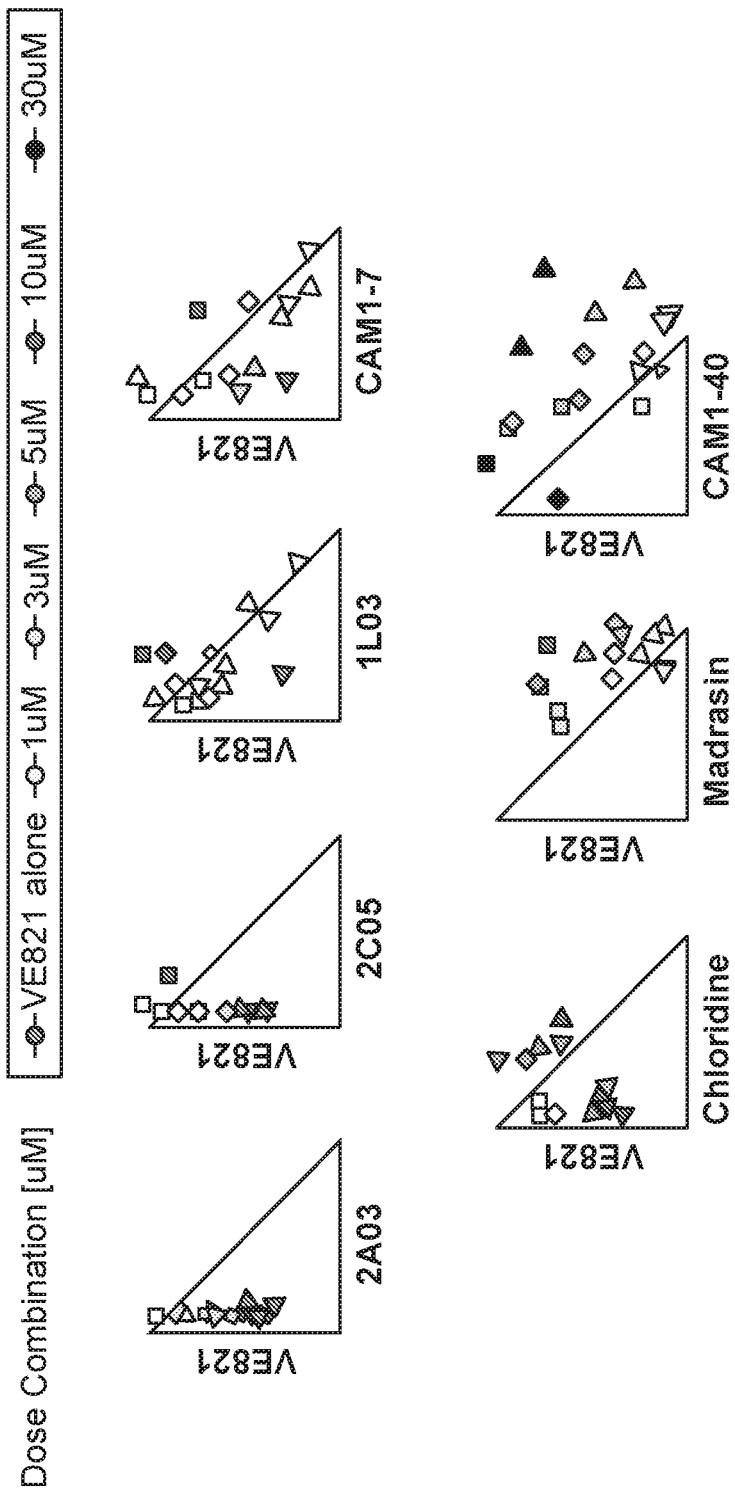
Figure 4H:
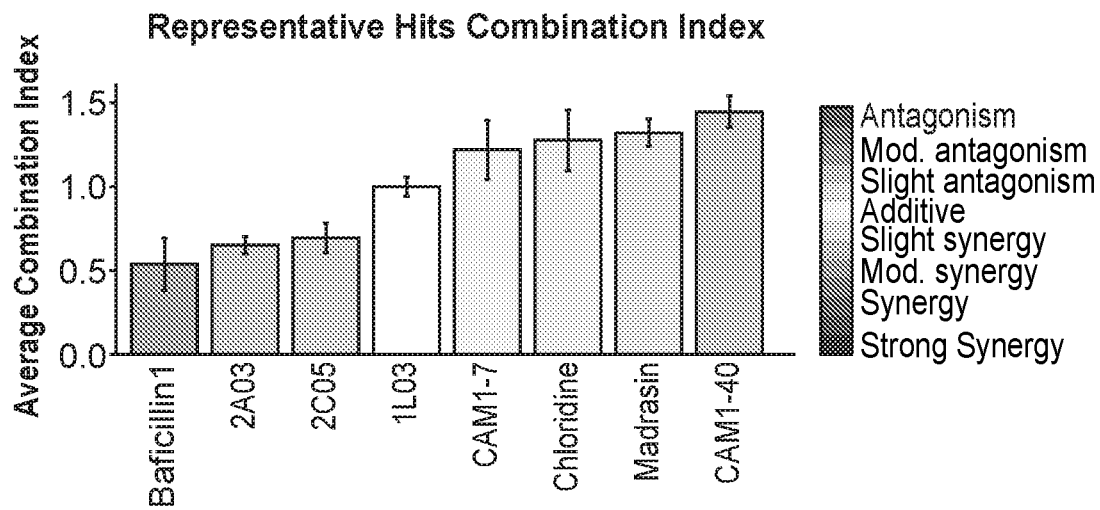
Figure 4I:
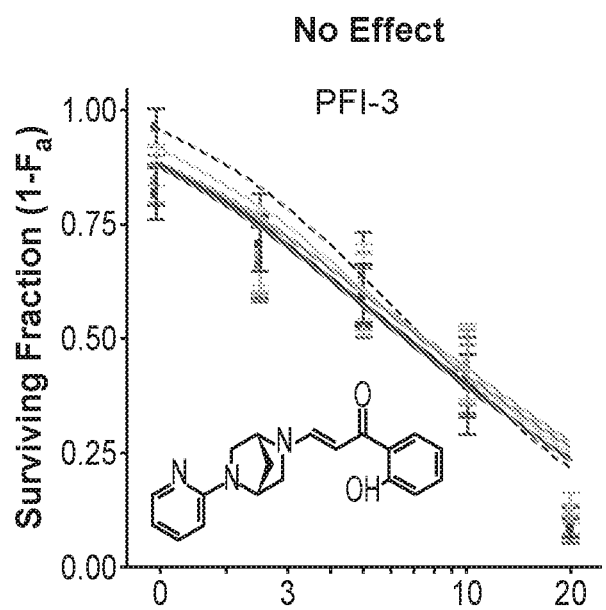

From our initial Bmi1 screen, we chose 8 representative compounds to compare to the lead candidate which were either commercially available, or comprised of the same oxadiazacyclodecone 12-member macrocyclic stereoisomer backbone as Baficillin1. First, we tested their ability to arrest mouse embryonic stem cells (mESCs) in G2/M and found that G2/M arrest in mESCs was inversely correlated with Bmi1 induction (FIG. 4a-b), suggesting that some inhibitors may be disrupting a BAF-complex function beyond inhibition of the Brg1 ATPase, which is relatively toxic. To examine a structure-activity-relationship of the compounds, HCT116 cells were then treated with increasing doses of VE-821 (1 uM-30 uM) and increasing doses of the putative inhibitors (1 uM-30 uM), both independently and with all possible combinations followed by quantification of synergy (FIG. 4c-h). We observed that two top hits (2A03 and 2C05) which contain the same backbone as Baficillin1 indeed demonstrated comparable synergy with VE-821 in HCT116 cells ($CI_{2A03}$=0.65±0.05, $CI_{2C05}$=0.69±0.08) (FIG. 4c,g-h). The administration of one compound when combined with VE-821, resulted in strictly additive effects ($CI_{1L03}$=0.99±.06) (FIG. 4d,g-h), and the four compounds with the highest percentage of G2/M arrest in ES cells demonstrated either mixed behavior or antagonism when combined with VE-821 ($CI_{Cam1-7}$=1.2±0.12, $CI_{Chloroidine}$=1.3±0.18, $CI_{Madrasin}$=1.4±0.04, $CI_{Cam1-40}$=1.5±0.09) (FIG. 4e-h). Interestingly, the published PFI-3 Brg1 bromodomain inhibitor showed no measurable individual dose-response or synergy effects in the ARID1A(+/+) or (−/− condition (FIG. 4i, FIG. 8), suggesting that inhibition of the lysine-binding function of Brg1 is not the major mechanism through which synergy is observed.

ATRi/BAFi Inhibition Results in Cell Cycle Defects

Figure 5A:
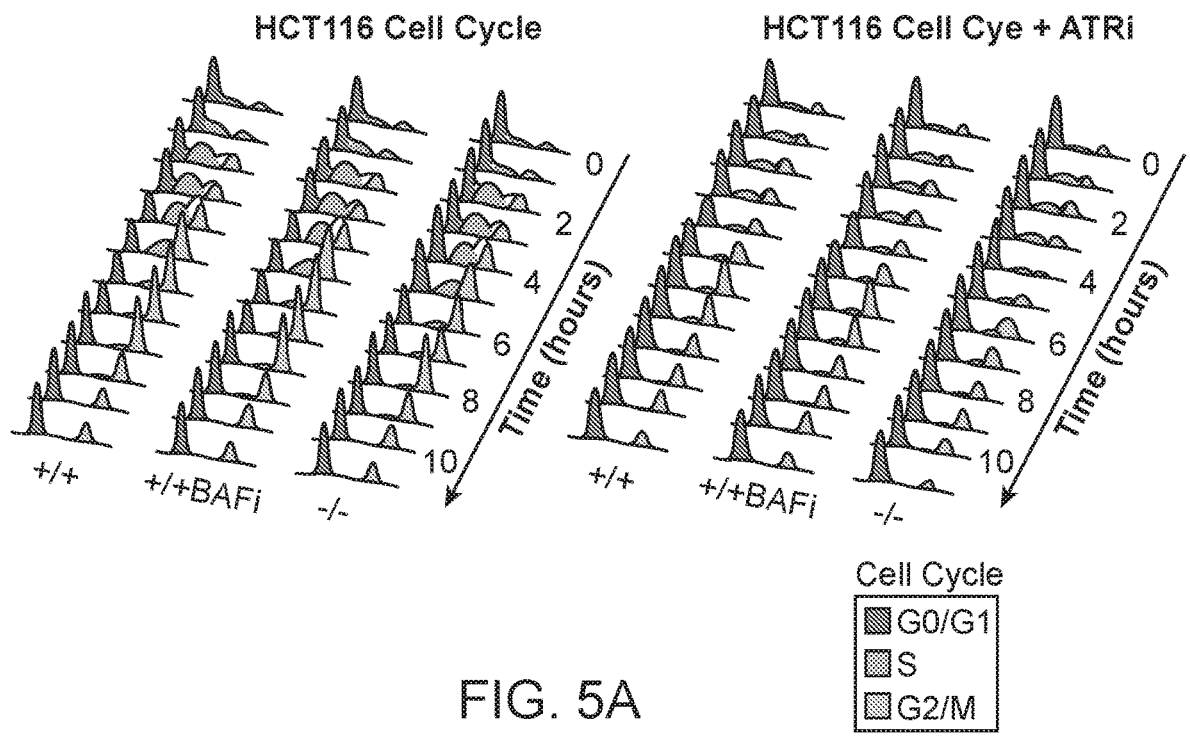
FIG. 5 shows BAF inhibition results in cell cycle defects and is exacerbated by DNA damage.
Figure 5B:
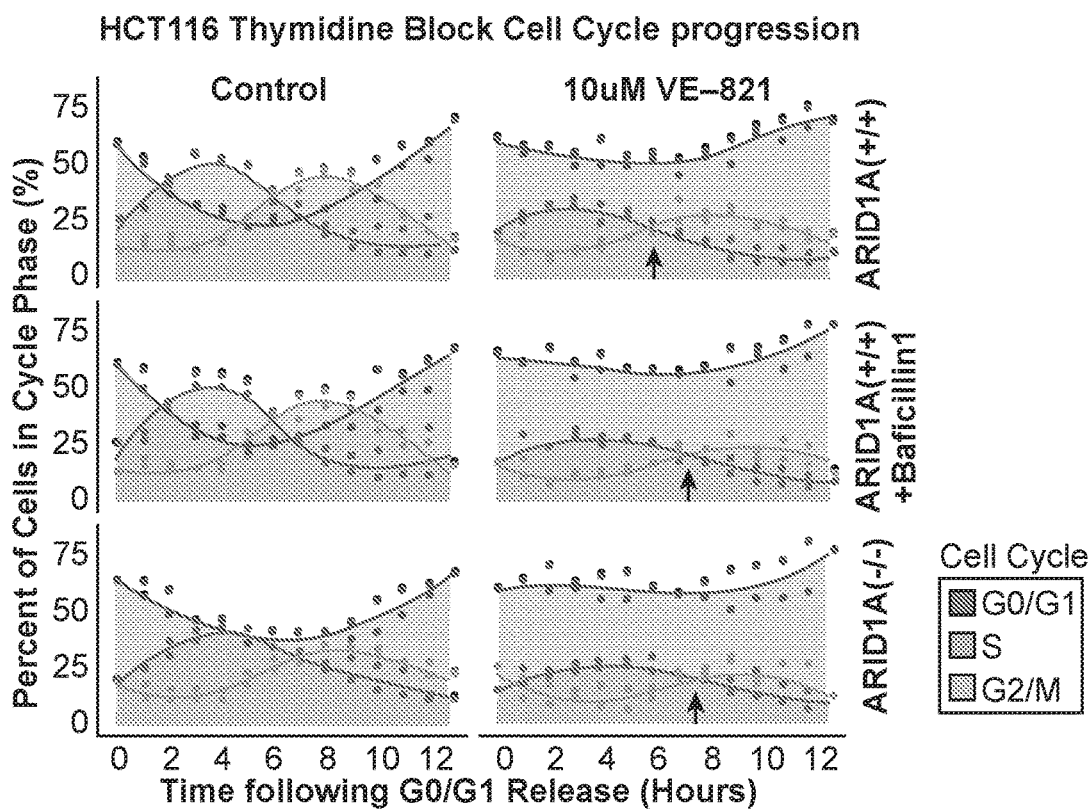

Given that we had previously identified that Baficillin1 is largely non-toxic in mESCs, we sought to assess through what mechanism BAFi may result in such dramatic cell viability phenotypes in the presence of ATR inhibitors. To investigate this, we synchronized cells in the early G1/S phase and then tracked their progression through the cell cycle upon release into media containing BAFi. To assess the full cell cycle, time points were collected beginning at early G0/G1 of the second cycle following release from thymidine block. We observed that HCT116 ARID1A(−/−) cells exhibited delayed progression through the S-Phase compared to both Baficillin1 treated (10 uM) and untreated HCT116 ARID1A(+/+) cells, but progressed through the cell cycle at similar rates (~11 hr per cycle) (FIG. 5a-b). This is consistent with our observation that BAFi independently has minimal toxicity or effects on proliferation. We were curious as to the mechanism by which BAFi in combination with ATRi exhibits unique sensitivity, so we further tracked the progression of cells released into media containing VE-821 (10 uM) in the presence or absence of Baficillin1 and compared to ARID1A(−/−) cells under the same conditions (FIG. 5b). Consistent with previous results[27], we observed that HCT116 ARID1A(−/−) cells displayed delayed progression through S phase and a build-up of cells in G2 (~11 h), which is exacerbated by ATRi through relief of the pile-up and premature entry into mitosis (FIG. 5a-b). In addition, when treated with 10 uM Baficillin1 in combination with ATRi, HCT116 ARID1A(+/+) exhibited delayed progression through S Phase (S/G2 Crossover at ~7.5 h) , similar to HCT116 ARID1A(−/−) cells, as compared to HCT116 ARID1A(+/+) untreated cells (S/G2 Crossover at ~6 h) (FIG. 5b). This result suggests that delayed progression through S Phase as a result of inhibition of ARID1A with Baficillin1, may be due to either an inability to repair DNA damage, or perhaps collapsed/stalled replication forks, in which the BAF complex has been previously implicated[38]. Further, we observe that when BAFi cells are treated with VE-821, their decreased entry and slowed progression through S Phase results in an inability to successfully complete their transition through the cell cycle, akin to knockout of ARID1A.

BAF Inhibition Effects Exacerbated by DNA Damage

Figure 5C:
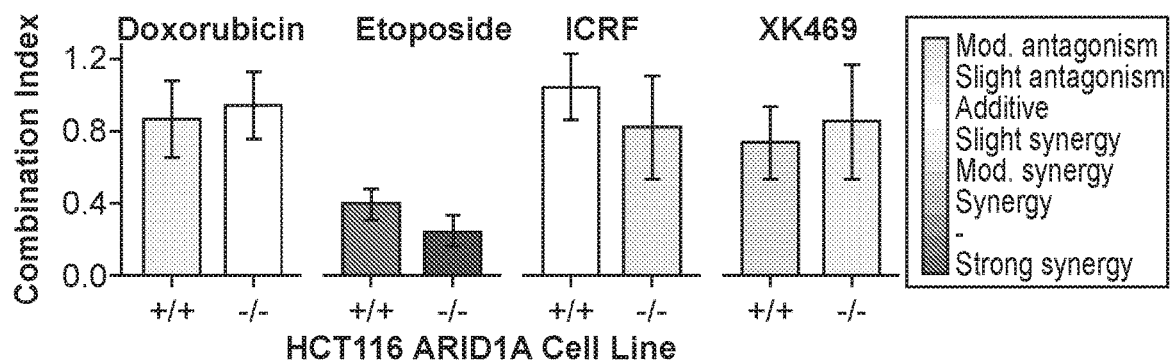
Figure 5D:
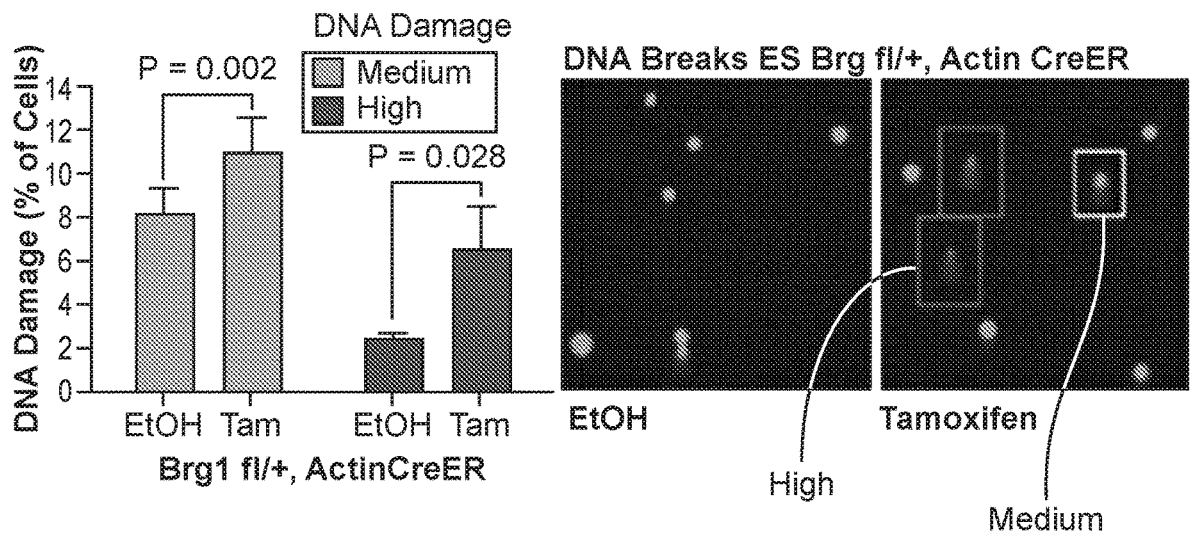
Figure 5E:
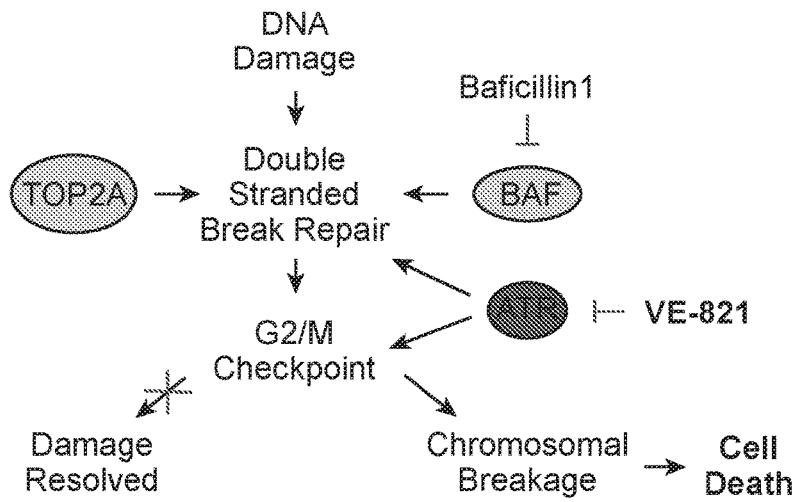
Figure 9:
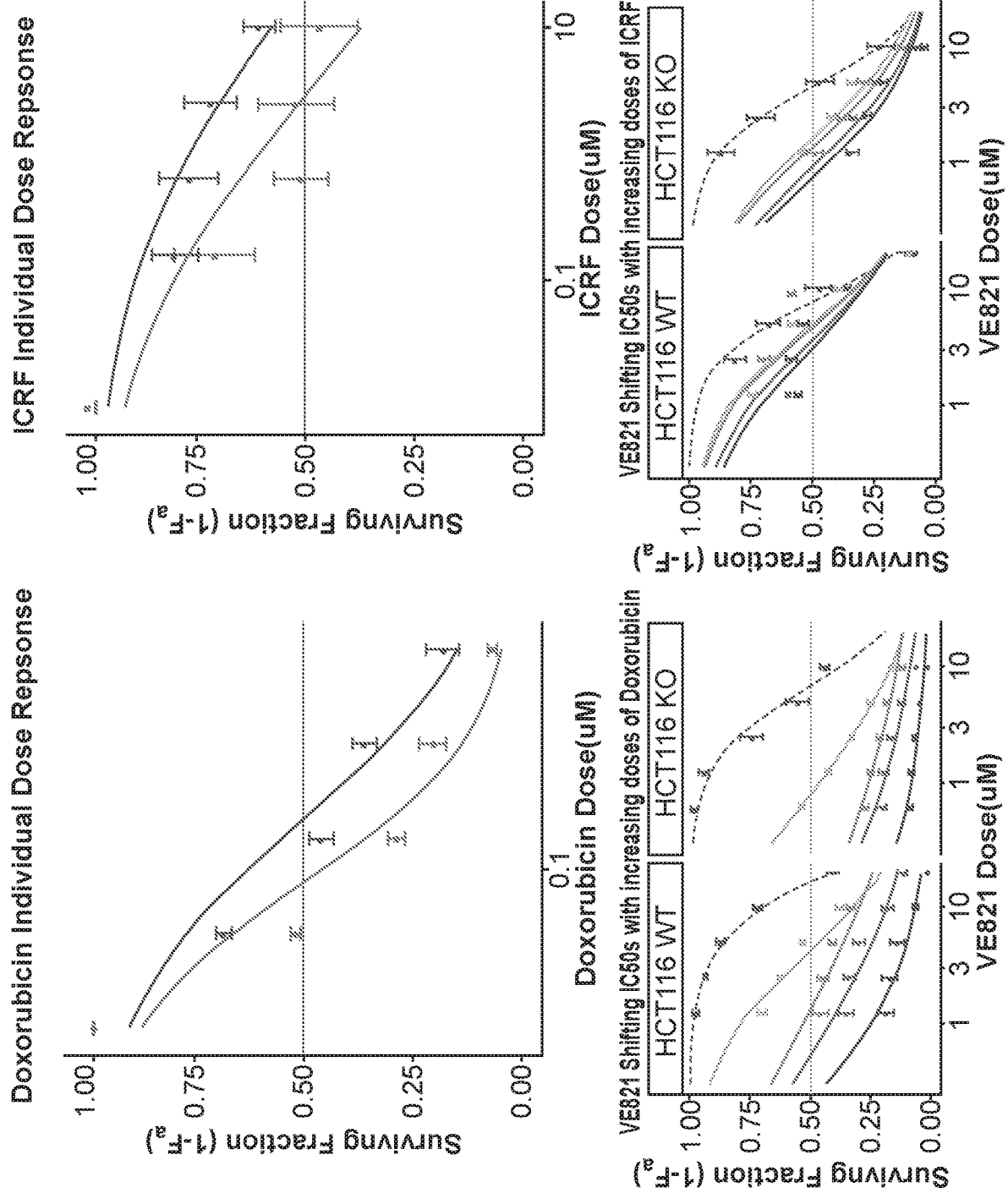
FIG. 9 shows that when +/+and −/−HCT116 ARID1A cells were treated with the TOP2i/ATRi combination, ICRF-193, Doxorubicin and XK469 all behaved as slightly synergistic/additive in both the +/+and −/− HCT116 cell lines.). In contrast, VE-821 and Etoposide demonstrated strong synergy in both the ARID1A(+/+) and ARID1A(−/−line, with "very strong synergy" observed in the knockout.
Figure 9:
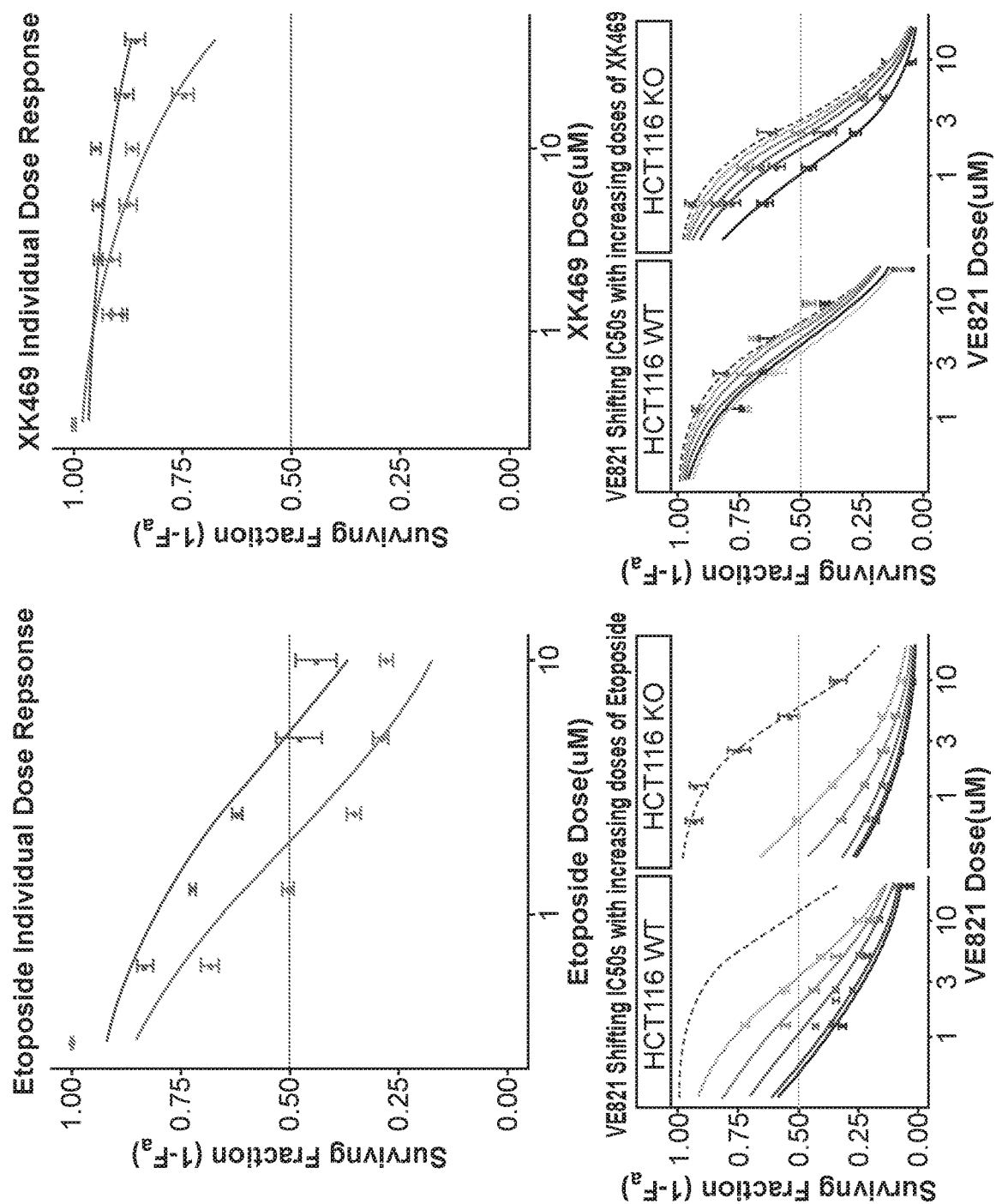

Recent studies have indicated a role in SWI/SNF remodeling complexes in DNA damage repair through either ATR/ATM-dependent phosphorylation of BAF170 which recruits BAF to double stranded breaks (DSB) repair sites[10] or through resolving DNA decatenation through a direct interaction with TOP2A[7]. Previously, it was reported that knockdown of TOP2A in HCT116(ARID1A−/−) cells resulted in high levels of cell death, which was presumed to be a result of a stronger dependency on TOP2A upon loss of ARID1A[27]. To assess the mechanism through which ATR-dependent BAF sensitivity is acting in concert with cancer cells and whether it was truly TOP2A-dependent, synergy was assessed between VE-821 and TOP2A/B inhibitors (TOP2i) in HCT116 (ARID1A+/+) and HCT116 (ARID1A−/−) cells. Both cell lines were treated with increasing doses of three TOP2A inhibitors (ICRF-193, Doxorubicin and Etoposide) and one TOP2B inhibitor (XK469)[39] for 5 days and their synergy in combination with increasing doses of VE-821 was calculated (FIG. 5c). When +/+ and −/− HCT116 ARID1A cells were treated with the TOP2i/ATRi combination, ICRF-193, Doxorubicin and XK469 all behaved as slightly synergistic/additive in both the +/+ and −/− HCT116 cell lines ($CI_{ICRF(+/+)}=1.0\pm0.05$, $CI_{ICRF(-/-)}=0.82\pm0.08$, $CI_{Dox(+/+)}=0.87\pm0.07$, $CI_{Dox(-/-)}=0.95\pm0.06$, $CI_{XK469(+/+)}=0.75\pm0.05$, $CI_{XK469(-/-)}=0.85\pm0.09$) (FIG. 5c, FIG. 9). In contrast, VE-821 and Etoposide demonstrated strong synergy in both the ARID1A (+/+) and ARID1A(−/−) line, with "very strong synergy" observed in the knockout ($CI_{Etop(+/+)}=0.4\pm0.02$, $CI_{Etop(-/-)}=0.24\pm0.02$) (FIG. 5c, FIG. 9). Unlike the TOP2A poisons ICRF-193[40] and Doxorubicin which indirectly generate DNA damage through inhibition of TOP2A[41,42], Etoposide prevents the re-ligation of DNA strands following TOP2-mediated cleavage, resulting in acute DSBs[43]. The increased synergy observed with Etoposide specifically, suggests that the "very strong synergy" observed in HCT116 ARID1A (−/−) may indicate an inability of cancer cells to repair DSBs in the absence of ARID1A. We have previously demonstrated that deletion of Brg1 in mouse embryonic stem cells (mESCs) results in the appearance DNA bridges during anaphase[7]. To confirm whether BAF itself is contributing to an increase in double stranded breaks, we turned to mES cells which have stable genomes, in contrast to HCT116 cells. Using $Brg1^{floxed/+}$ ($Brg1^{fl/+}$) actin-creER mouse embryonic stem cells, we performed single cell gel electrophoresis (comet assay) and observed that tamoxifen-induced deletion of a single copy of the ATPase subunit results in an increase in both medium and high amounts of DSBs (FIG. 5d). This increase in DSBs in the absence of Brg1 may explain the exacerbated synergistic effect observed in the presence of Etoposide (FIG. 5e).

BAF Inhibition Sensitizes Highly-Mutated Cancers to ATRi

Figure 6A:
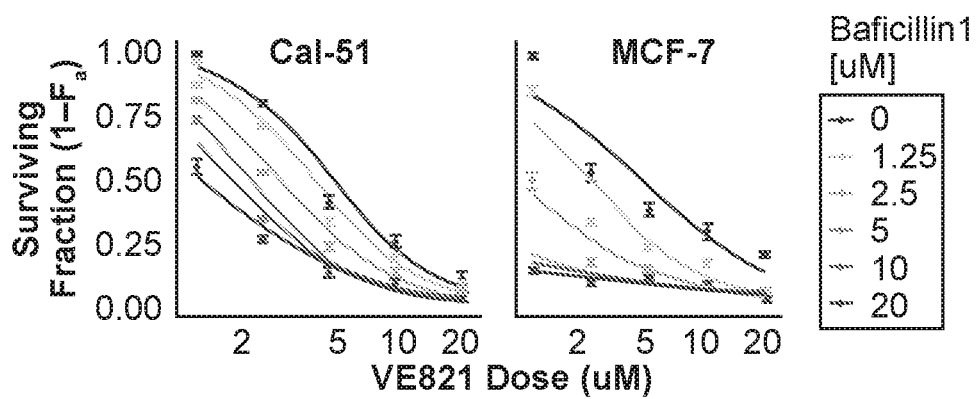
FIG. 6 shows that BAFi sensitizes highly mutated cancers to ATRi.
Figure 6B:
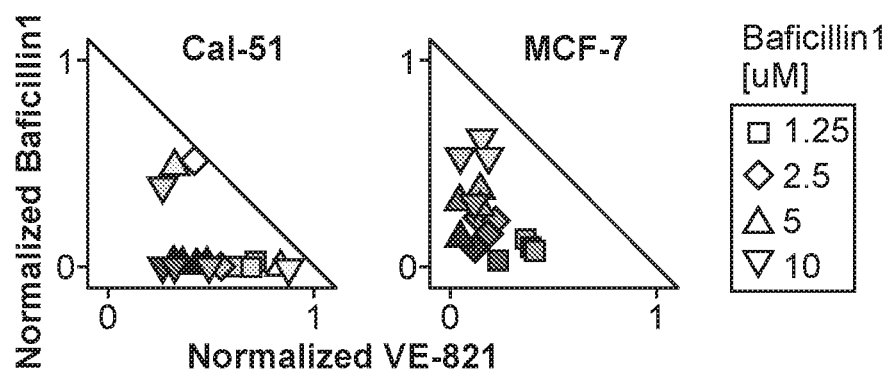
Figure 6C:
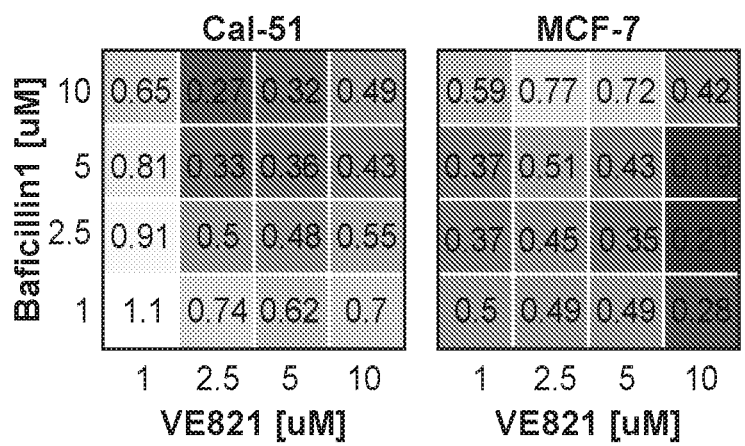
Figure 6D:
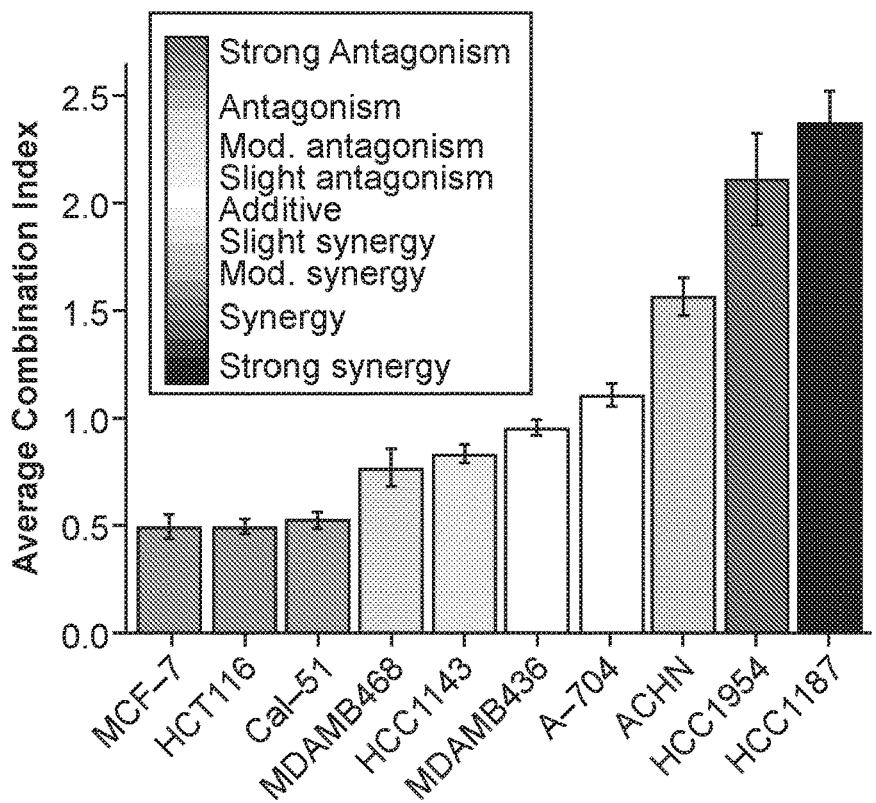
Figure 6E:
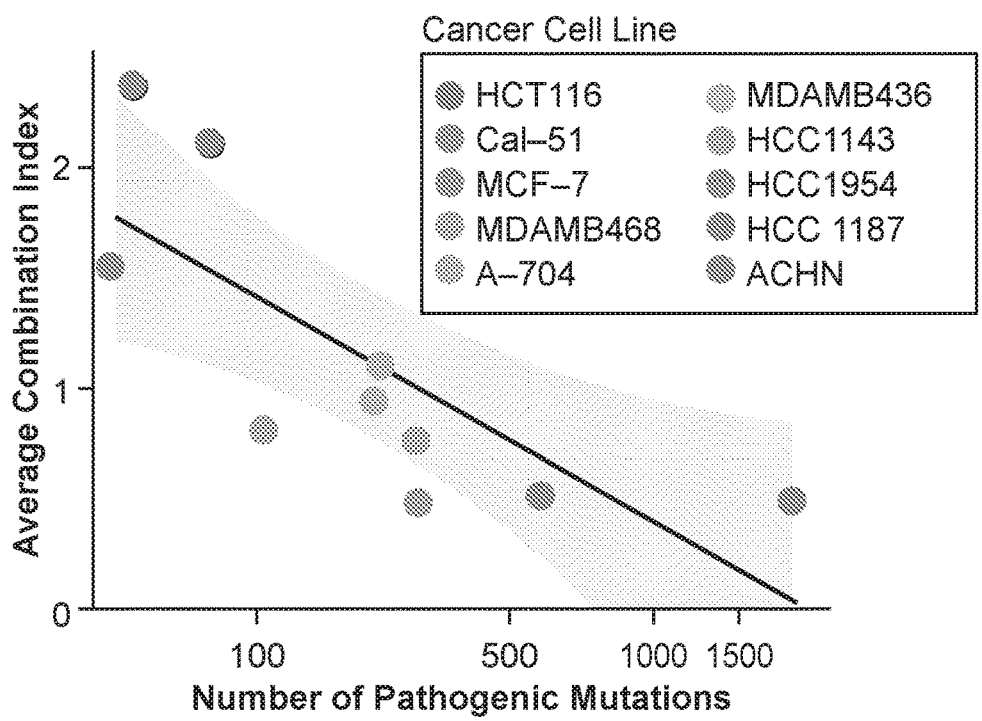
Figure 10:
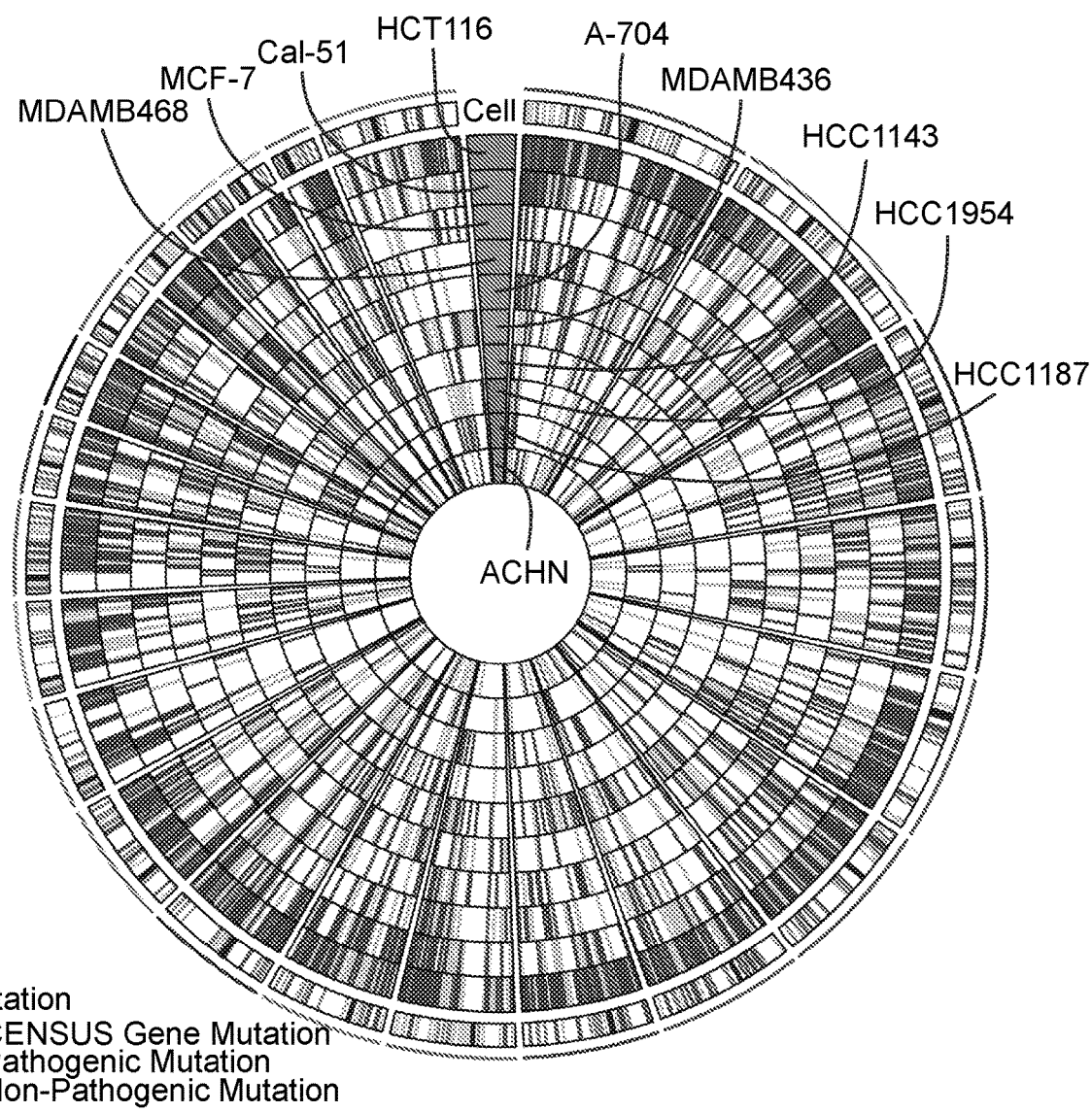
FIG. 10 shows Cal-51 and MCF-7 are both considered aggressive, highly mutated breast cancer cell lines with numerous COSMIC Census gene mutations.

In ARID1A-deficient tumors, ATR inhibition is thought to trigger premature mitotic entry and chromosome instability that cannot be resolved, resulting in mitotic catastrophe[27]. Recent reports have demonstrated that loss-of-function Brg1 mutations have increased sensitivity to topoisomerase II inhibition in the presence of PRC2 inhibitors[44], and that cancers with oncogenic BAF mutations may also exhibit increased sensitivity to PRC2 inhibition[45]. We sought to assess whether generic BAF inhibition might sensitize a host of cancers to ATR inhibition. We tested the efficacy of BAFi and ATRi on nine additional human cancer cell lines including seven Breast cancer cell lines (HCC1143, HCC1954, HCC1187, MDAMB-468, MDA-MB-436, Cal-51, MCF-7) and two renal clear cell carcinoma cell lines (A-704, and ACHN). Cal-51 and MCF-7 are both considered aggressive, highly mutated breast cancer cell lines with numerous COSMIC Census gene mutations (FIG. 10). HCC1143 and MDA-MB-468 are sporadic basal-likecancers, HCC1187 is a triple-negative breast cancer, and HCC1954 and MDA-MB-436 are BRCA1 mutant breast cancers which harbor single driver mutations. To assess synergy, each cell line was treated with 5 doses of VE-821 (1.25 uM-20 uM) and 5 doses of Baficillin1 (1.25 uM-20 uM), both independently and with all possible combinations. Like HCT-116 cells, Baficillin1 sensitized MCF-7 and Cal-51 cells lines to treatment with VE-821 (FIG. 6a). Further, synergy between the two molecules was observed in both cell lines ($CI_{MCF-7}=0.45\pm0.04$, $CI_{Cal-51}=0.57\pm0.09$) (FIG. 6b-c). Interestingly, the BRCA1 mutant line MDA-MB-436 was significantly more sensitive to Baficillin1 independently (FIG. 11), which suggest BAFi as an independent therapeutic strategy for BRCA1 cancers. However, unlike the more mutated cancer cell lines, the combinatorial effects of BAFi/ATRi in MDA-MB-436 cells were strictly additive, while the two renalcell carcinoma lines which harbor a mutation in the PBAF specific subunit PBRM1[36] demonstrated antagonism (FIG. 6d). Of the ten total cancer cell lines tested, we calculated the average combination index for doses ranging from 1.25-10 uM and observed that a lower combination index (higher synergy) was roughly correlated with the number of pathogenic mutations (FIG. 6e), further suggesting that DNA damage exacerbates the effects of Baficillin1 in cancer.

Discussion

In this study, we sought to assess whether small-molecule inhibition of SWI/SNF complexes could serve as a viable therapeutic strategy for the treatment of cancer. The results indicate that novel small-molecule BAF inhibitors act on ARID1A containing BAF complexes. Although inhibitors of BAF subunits have been reported (PFI-3, and ATPase inhibitors), to date, none of these small molecules have been reported to have therapeutic value in cancer. By combining our BAF inhibitor with inhibitors of the ATR kinase, we demonstrate that non-BAF mutated cancer cells undergo a hyper-synthetic lethal effect, particularly in highly mutated cancer lines, despite the relatively non-toxic effects of Baficillin1 independently.

Therapeutic targeting of multi-subunit complexes has been a challenge due to the varied functions and compositions of such complexes, but also the inability to validate target specificity using conventional means. Suspected inhibitors of protein complexes likely lack substrate affinity for a single binding pocket, which poses significant barriers to canonical biochemical characterizations. Further, challenges surrounding complex purification, along with the lack of structural insights (as there is no published crystal structure) into such complexes has kept the development of specific inhibitors largely out-of-reach. Based on the sensitivity of ARID1A mutant cells to ATR inhibition, we reasoned that small molecules that block the function of BAF complexes would also be synergistic with ATR inhibition. Many of the BAF inhibitors that we detected in our screen were highly toxic, as would be expected based on the essential role of most subunits of the BAF complex. However, specific molecules that block the de-repressive function of BAF complexes are not toxic and yet we show are highly synergistic with ATR inhibition in several human cell lines. Of the initial hits that arose from our previous screen, we have observed that the macrocyclic candidates from a diversity-oriented-synthesis (DOS) library[30,46] [6] exhibited stereospecifity which provides insight into structure-activity relationships and will aid in the development of better BAF inhibitors.

The need for active small-molecule probes against SWI/SNF complexes is highlighted by the fact that BAF subunits are one of the most highly mutated genes in human cancer, with no adequate chemical probes to date. Recent reports suggest a critical role for PBAF complexes in the maintenance of cohesion at kinetochores and the recruitment to sites of transcriptional-mediated DSB S[33,47] while BAF regulates the binding of TOP2a to chromatin to mediate DNA decatenation. Our data further suggests that mechanistically, inhibition of the BAF complex sensitizes cancer cells to ATR inhibition through a G2/M checkpoint defect, which is exacerbated by DNA damage either through increased double stranded breaks or a high mutational background in aggressive cancers. This affect is aggravated by ATR inhibition which mitigates the G2/M checkpoint, thereby forcing cells into mitosis without repairing the acquired DNA damage, resulting in mitotic catastrophe and subsequent cellular arrest. The limited toxicity and S-phase effects of Baficillin1 independently suggests that in the context of cancer, ATR-mediated checkpoint bypass may expedite any TOP2A-mediated defects that ARID1A-deficient cells acquire over time. Due to the many unclear functions of the BAF complex, it is possible that the effects observed are either a direct result of loss of ATR-mediated recruitment of BAF to DNA damage points, by-pass of the G2/M checkpoint or a combination of both.

Our results suggest that therapeutic inhibition of BAF complexes in the presence of ATR inhibitors may serve as a viable therapeutic strategy in certain cancers. We observe that this strategy may be effective in cancers that have not only acquired BAF complex mutations, but also in highly mutated cancers which have evolved mechanisms to by-pass important DNA damage checkpoints. This suggests that the development of small molecules targeting human SWI/SNF or BAF complexes is a viable and promising therapeutic strategy.

Further decription of the Figures

FIG. 1: Strategy for assessing hyper-synthetic lethality of combination BAFi and ATRi. (a) Macromolecular assembly of SWI/SNF complexes. BAF/PBAF-specific subunits labelled in blue/red respectively. (b) Workflow of screen used to identify putative BAF inhibitors. (c) Structure of Baficillin1. (d) Summary of results (combination index scores, normalized isobolograms) obtained in Chou-Talalay method for assessment of synergy.

FIG. 2: BAF and ATR Inhibition is synergistic. (a) Dose response curves of HCT116 cell line exposed to increasing concentrations of ATR inhibitor (VE-821) and putative BAF inhibitor (Baficillin1) for 5 days. (b) Shifting IC50 dose-response curves of HCT116 cells treated with VE-821 and increasing doses of Baficillin1 for 5 days (c) Normalized isobologram of synergy between VE-821 and Baficillin1 in HCT116 cells (d) Combination index values quantify synergy between Baficillin1 and VE-821 (e) Plot of the dose reduction index of increasing concentrations of VE-821 and 5 concentrations of Baficillin1 against the fraction of affected cells.

FIG. 3: Putative BAF Inhibitor, Baficillin1 phenocopies knockdown of ARID1A. (a) Cell survival data from HCT116 cells infected with shRNA lentivirus targeting ARID2 (blue), ARID1A (green), Control (red), and HCT116 (ARID1A −/−) cells (green-dashed). Following lentiviral transduction and selection, cells were exposed to VE-821 or Baficillin1 for 5 continuous days. Error bars represent s.d. of eight technical replicates in three separate experiments in 384-well plates. (b) Gene expression (RNA levels) of ARID1A, ARID2, and ARID1B in HCT116 (WT, shARID1A, shARID2). Delta-Delta CT values compared to Gapdh and WT HCT116. (c) Shifting IC50 plots, normalized isobolograms and combination index plots of HCT116 cells treated with VE-821 and increasing doses of Baficillin1 for 5 days. (d) Shifting IC50 plots, normalized isobolograms and combination index plots of HCT116 cells infected with shRNA lentivirus targeting ARID2, treated with VE-821 and increasing doses of Baficillin1 for 5 days. (e) Shifting IC50 plots, normalized isobolograms and combination index plots of HCT116 cells infected with shRNA lentivirus targeting ARID1A, treated with VE-821 and increasing doses of Baficillin1 for 5 days. (f) Average combination indexes for HCT116 cells infected with shRNA lentivirus targeting ARID2, ARID1A, Control, and HCT116(ARID1A −/−) cells.

FIG. 4: Structure Activity Relationship of Putative BAF Inhibitors. (a) Assessment of toxicity of putative inhibitors by cell cycle analysis arrest in ESCs after release from double thymidine block. Data represent three separate cell-cycle analyses. (b) Induction of Bmi1 and Ring1a expression of 5 putative hits. Data represents results from original screen. (c) Structures, shifting dose response, and CI grid of putative inhibitors demonstrating synergism: 2A03 and 2C05 following treatment with increasing doses of VE-821 (1-30 uM) and increasing doses of each putative inhibitor (1-30 uM) for 5 days. (d) Structure, shifting dose response, and CI grid of putative inhibitor (1L03) demonstrating addition (as treated in 4c). (e) Structures, shifting dose response, and CI grid of putative inhibitors demonstrating a mixed response: Cam1-7, Chloridine (as treated in 4c). (f) Structures, shifting dose response, and CI grid of putative inhibitors demonstrating antagonism: Madrasin, and Cam1-40 (as treated in 4c). (g) Normalized isbolograms 8 compounds following treatment with increasing doses of VE-821 (1-30 uM) and increasing doses of each putative inhibitor (1-30 uM) for 5 days. (h) Average combination indexes for HCT116 treated with putative BAF inhibitors and VE-821 (as treated in 4c). (i)

Structure and shifting dose response of PFI-3 Brg1 bromodomain inhibitor demonstrating no measureable effects (as treated in 4c).

FIG. 5: BAF inhibition results in cell cycle defects and is exacerbated by DNA damage. (a) Histogram of the cellular Propidium iodide-stained DNA content determined by FACS, in HCT116 ARID1A +/+, ARID1A −/−, and ARID1A+/+ treated with 10 uM of Baficillin1 at the indicated time points following release from cell synchronization in G0/G1, in the absence (left) or presence of 10 uM VE-821 (right). Time points begin at maximum G0/G1 of second division following release from thymidine block (10 hr post release). (b) Time course illustrating the percentage of cells in G0/G1 (red), S (blue), or G2/M (green) phase of synchronously growing HCT116 ARID1A+/+, ARID1A−/−, and ARID1A+/+treated with 10 uM of Baficillin1 in the absence (left) or presence of 10 uM VE-821 (right) following release from double thymidine block. Time points begin at maximum G0/G1 of second division following release from thymidine block (10 hr post release). (c) Average combination index of HCT116 ARID1A +/+, ARID1A −/− cells following synergy analysis in combination with 5 increasing doses of VE-821 and 5 increasing doses of TOP2A/B inhibitors, Doxorubcin, Etoposide, ICRF-193, and XK469. (d) Comet analyses of Brg1$^{floxed/+}$ (Brg1$^{fl/+}$) actin-creER ESCs following treatment with tamoxifen (Left) Quantitative analysis of three independent experiments. Percentage of cells medium or high levels of DNA damage. (Right) Representative images. (e) Model of BAFi/ATRi induced hyper-synthetic lethality mechanism and sensitivity to DNA damage response.

FIG. 6: BAFi sensitizes highly mutated cancers to ATRi. (a) Shifting IC50 dose response survival curves, (b) Normalized isobolograms, (c) combination index grids of cancer cell lines Cal-51 and MCF-7 to increasing doses of VE-821 and Baficillin1. (d) Average combination indices between 1.25-10 uM of cancer cell lines HCT116, HCC1143, HCC1954, HCC1187, MDA-MB-468, MDAMB-436, Cal-51, MCF-7, A-704, and ACHN, ranked from lowest to highest synergy. (e) Average combination index, plotted against number of pathogenic cancer mutations obtained from the COSMIC cancer cell line database of ten cancer cell lines tested.

FIG. 7 shows the homozygous loss-of-function HCT116 (ARID1A−/−) cell line (CI−/−=1.44±0.12) which demonstrated slightly antagonistic effects.

Figure 8B:
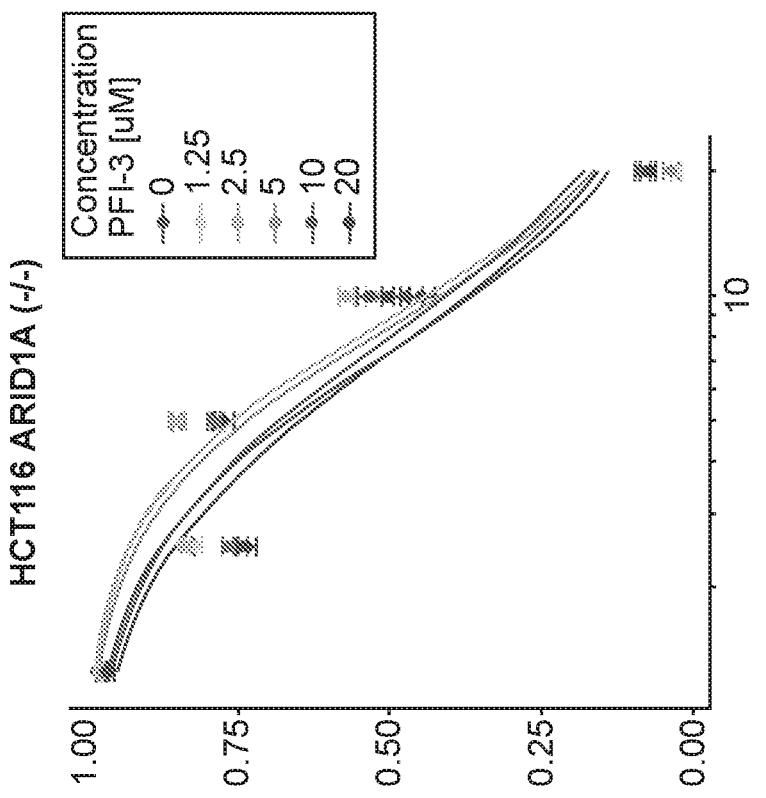
FIG. 8 shows the PFI-3 Brg1 bromodomain inhibitor showed no measurable individual dose-response or synergy effects in the ARID1A(+/+) or (−/−condition.
Figure 8A:
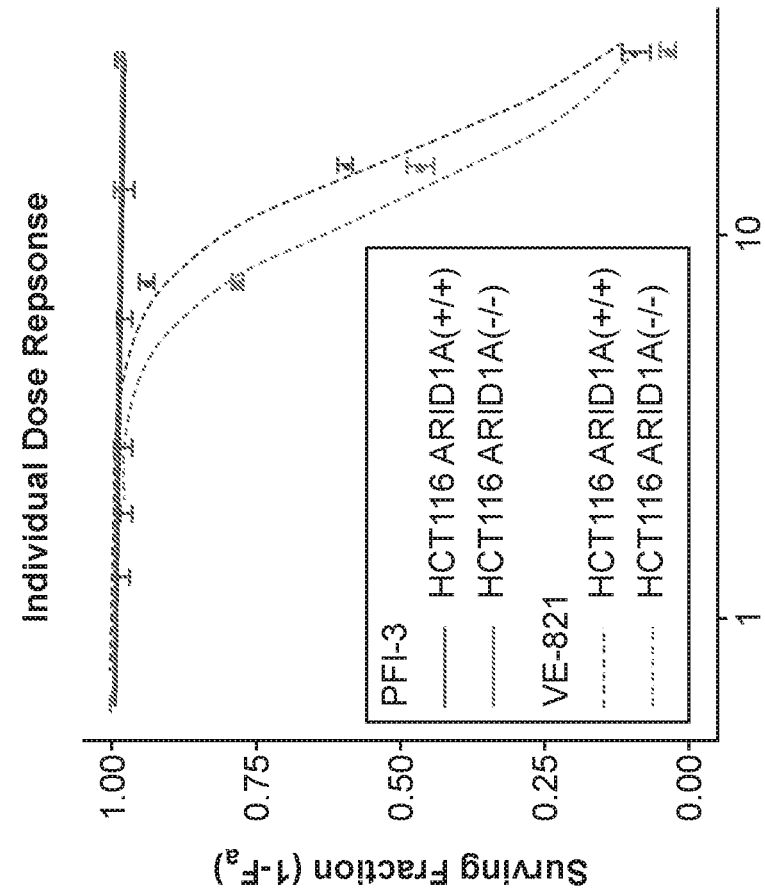

FIG. 8 shows the PFI-3 Brg1 bromodomain inhibitor showed no measurable individual dose-response or synergy effects in the ARID1A(+/+) or (−/−) condition.

FIG. 9 shows that when +/+and −/− HCT116 ARID1A cells were treated with the TOP2i/ATRi combination, ICRF-193, Doxorubicin and XK469 all behaved as slightly synergistic/additive in both the +/+and −/− HCT116 cell lines.). In contrast, VE-821 and Etoposide demonstrated strong synergy in both the ARID1A(+/+) and ARID1A(−/−) line, with "very strong synergy" observed in the knockout.

FIG. 10 shows Cal-51 and MCF-7 are both considered aggressive, highly mutated breast cancer cell lines with numerous COSMIC Census gene mutations.

Figure 11:
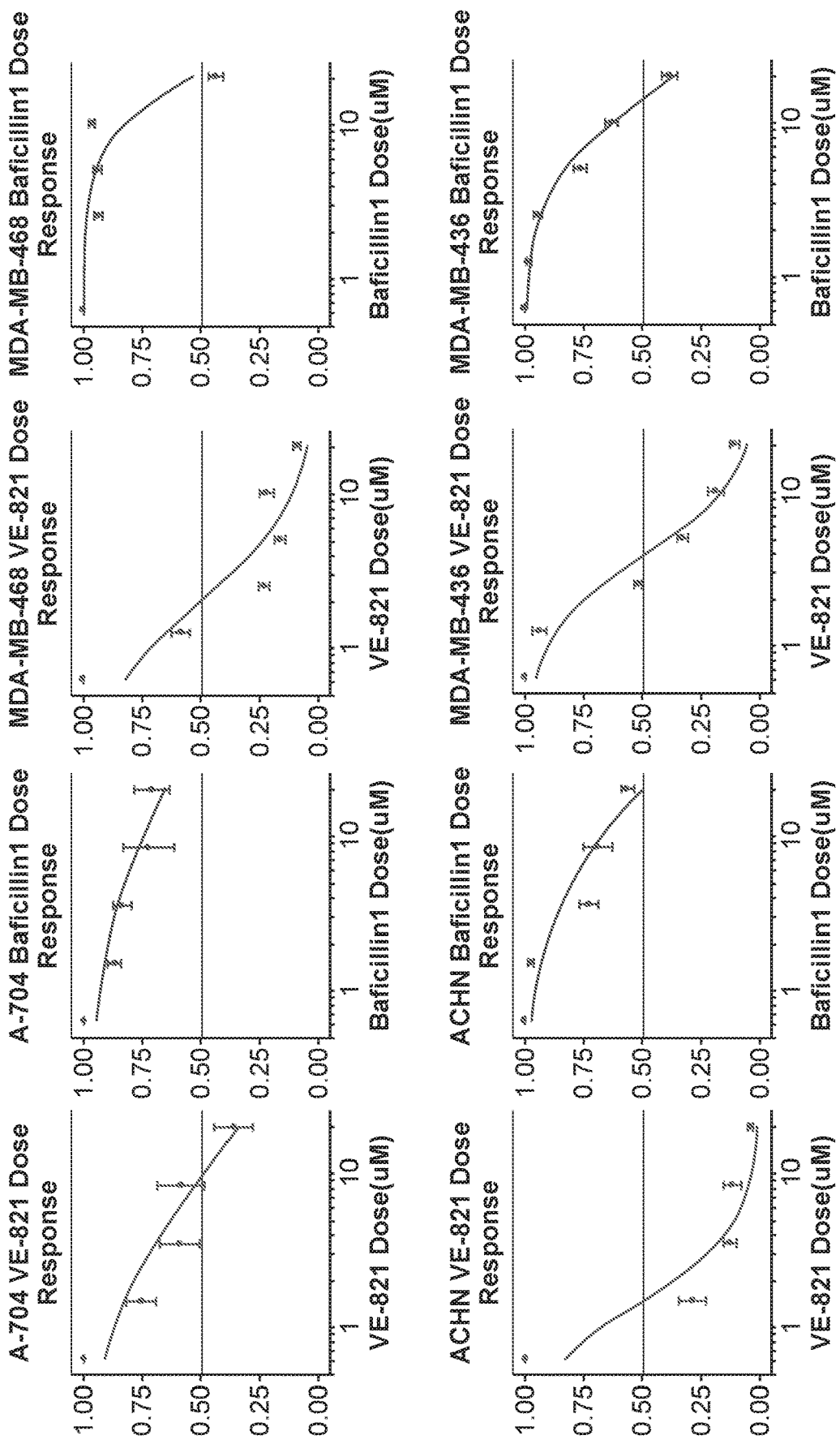
FIG. 11 shows the BRCA1 mutant line MDA-MB-436 was significantly more sensitive to Baficillin1 independently, hich suggest BAFi as an independent therapeutic strategy for BRCA1 cancers.
Figure 11:
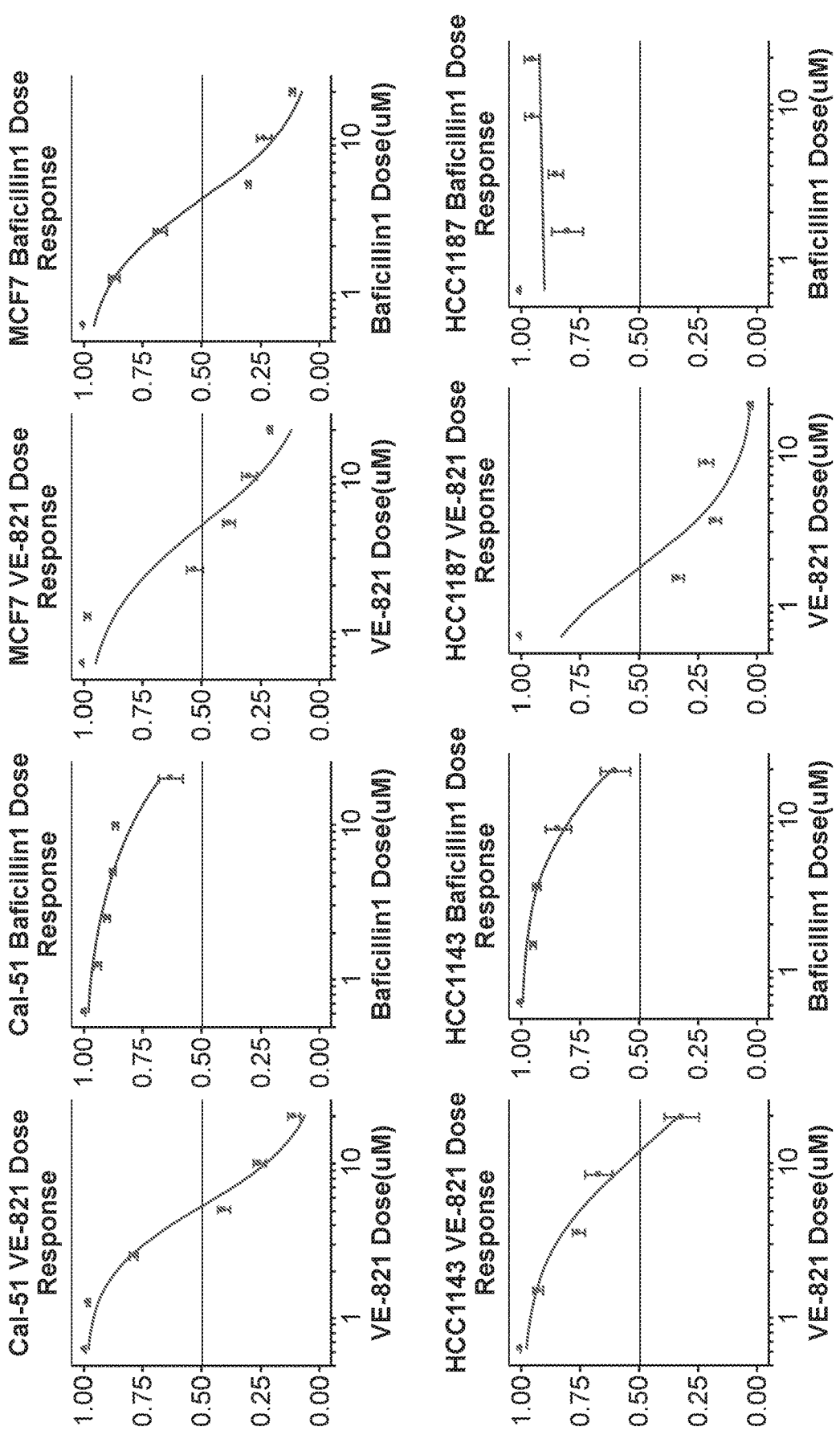

FIG. 11 shows the BRCA1 mutant line MDA-MB-436 was significantly more sensitive to Baficillin1 independently, hich suggest BAFi as an independent therapeutic strategy for BRCA1 cancers.

Materials and Methods

Cell Culture

Isogenic HCT116 ARID1A(+/+) and ARID1A(−/−) cell lines were originally obtained from Horizon Discovery. MCF-7, Cal-51, A-704, and MDA-MB-436, MDA-MB-468, HCC1143, HCC1187, HCC1954, and ACHN cell lines were obtained from American Type Tissue Collection. All cell lines were grown in McCoy's 5a Media supplemented with 10% FBS.

Chemicals

VE-821 and SU-6656 were purchased from Selleck Chem. Baficillin1 was synthesized as described by Fitzgerald and colleagues[48]. Chloridine (Pyrimethamine), Madrasin, ICRF-193, Etoposide, and XK469 were purchased from Sigma-Aldrich. Doxorubicin was purchased from AK Scientific. Cam1-7 and Cam1-40 (Pubchem CID 49792165) were purchased through Evotec. 1L03 (Pubchem CID 46902783), 2A03 (Pubchem CID 54631898), and 2C05 (Pubchem CID 54631408) were obtained.

Synergy Viability Assays

Viability assays were performed in 384-well plates. Cells were plated at 500 cells/well. Each drug was administered in 5-doses with 4 replicates per plate, and each 5×5 drug combination was administered with 8 replicates per plate, 24 hours after seeding. All error bars represent 4 or 8 technical replicates averaged over 3 independent experiments. Media containing fresh drug was replaced every 48 hours. After 5 days, cellular viability was measured using CellTitre blue, as described by the manufacturer.

Lentiviral Preparation and Infection

Lentiviruses were produced in Lenti-X 293T cells (Clonetech) via spinfection with polyethylenimine transfection. 293T-x cells were transfected with PEI (Polysciences Inc., 24765) with lentiviral PLKO shARID1A or GIPZ shARID2 knockdown vectors, co-transfected with packaging vectors pspax2 and pMD2.G as previously described[49]. PLKO shRNA construct targeting ARID1A (TRCN0000059090: shRNA-2) was obtained[50] and GIPZ Human ARID2 shRNA was purchased from Dharmacon (CloneId:V2LHS_74399). 12 h after transfection, media was changed and after another 48 h media was collected and supernatant was used to spinfect cells in the presence of 10 µg/ml Polybrene (Santa Cruz Biotechnology) at 1000 g for 1 hr. Cells were selected with 2 µg/ml puromycin beginning 48 hr after infection.

RT-qPCR Analysis

RNA was extracted from cells using Trisure (Bioline) and cDNA was synthesized from 1 ug RNA using the SensiFAST SYBR Lo-Rox (Bioline). Delta Samples were run on a QuantStudio 6 Flex system (Life Technologies). $2^{-\Delta\Delta CT}$ was calculated as described by Livak and Schmittgen[51] where $-\Delta\Delta CT=(CT_{GOI}-CT_{Gapdh})_{ARID1A(-/-)}-(CT_{GOI}-CT_{Gapdh})_{ARID1A(+/+)}$. Primers for qPCR are included in Table 1.

TABLE 1 qPCR primers

| Gene Sequence | Gene Sequence | SEQ ID NO: |
|---|---|---|
| hARID1A F1 | ACCTCTATCGCCTCTATGTGTCTGT | 1 |
| hARID1A R1 | CTGGCAGCACTGCTTGATGT | 2 |
| hARID1B F2 | GCAAGGTGTGAGTGGTTACTG | 3 |
| hARID1B R2 | GGACTGGGACGGCAGATACT | 4 |
| hARID2 F2 | CAAGTGCAGGGCCAGCCTAAC | 5 |
| hARID2 R2 | AACCTGTGAGGGTGTCTGAAACC | 6 |
| hTOP2A F1 | GAATGTGACAGTGAAGAAGACAGC | 7 |
| hTOP2A R1 | AGACACCAGAATTCAAAGCTGGATC | 8 |
| hTOP2B F1 | CGGATTCAGAATTTGGCATTCCAAAGA | 9 |
| hTOP2B R1 | GCTTGTTGTTTTGGATGTTTTCCTGC | 10 |
| hGAPDH F1 | GCCAGCCGAGCCACAT | 11 |
| hGAPDH R1 | CTTTACCAGAGTTAAAAGCAGCCC | 12 |

Cell Synchronization

HCT116 cells were plated at 2E6 cells/well in 6-well plates and incubated with 2 mM thymidine for 18 hr, released into fresh media for 8 h, and incubated with thymidine again for 16 hr, washed several times with PBS, and released into fresh media containing either 10 uM Baficillin1, 10 uM VE-821, or both to synchronize into G1/early S. To begin collection at the maximum percent of cells in G0/G1, cells were allowed to proceed through one cell cycle for 9 hours, and then collected at respective time points. The maximum G0/G1 time point occurred at 10 hours post-release from thymidine block. ESCs were incubated with 2 mM thymidine for 7-8 h, released into fresh media for 7 h, and then incubated with thymidine again for 7 h. Cells were washed several times with PBS, released into fresh media, and collected at respective time points.

Cell Cycle Analysis

For hour-by-hour analysis, cells were collected, rinsed with PBS, and vortexed while adding 1mL ice cold 70% ethanol. Cells fixed overnight, pelleted at 1000×g, rinsed in PBS, resuspended in PBS containing 50 ug/mL RnaseA and 10 ug/mL Propidium Iodide and incubated at 37C for 30 min. Flow cytometry analysis was performed on a BD Accuri Flow Cytometer. Individual cells were gated based on forward and side scatter, auto fluorescent cells were omitted, and remaining cells were then analyzed for propidium iodide levels. To determine the percent of cells in each phase, DNA content histograms histograms were analyzed using R-package "mixtools" EM algorithm for mixtures of univariate normals. The areas of each mixed normal distribution were calculated to represent the total number of cells in each phase of the cell cycle. For ESCs, cell cycle analysis was performed using BD Biosciences BrdU-FITC FACS kits. ESCs were incubated with BrdU for 1 h and the percent of cells in G2/M, stained with 7-AAD and analyzed on a BD FACScan.

Comet Assay

Briefly, cells were trypsinized and double-strand break (DSB) repair was analyzed by single cell gel electrophoresis (comet assay) using Cell BioLab's OxiSelect Comet Assay Kit according to the manufacturer's instructions. After staining with vista Green DNA dye, comet images were captured by fluorescence microscopy. For each experiment, >300 cells were counted from >20 images per experiment for 3-4 experiments for each condition. In each sample, the percentage of cells with medium and high tail moments was calculated to represent the cells with intact DNA. $Brg1^{floxed/+}$ actin-creER mESCs were analyzed 72 hr after treatment.

REFERENCES

1. Khavari, P. A., Peterson, C. L., Tamkun, J. W. & Mendel, D. B. BRG 1 contains a conserved domain of the SWI 2/SNF 2 family necessary for normal mitotic growth and transcription. *Nature* (1993).
2. Wang, W., Côté, J., Xue, Y., Zhou, S. & Khavari, P. A. Purification and biochemical heterogeneity of the mammalian SWI-SNF complex. *The EMBO Journal* (1996). 3. Zhang, X. et al. Transcriptional repression by the BRG1—SWI/SNF complex affects the pluripotency of human embryonic stem cells. *Stem Cell Reports* 3, 460-474 (2014).
4. Lessard, J. et al. An Essential Switch in Subunit Composition of a Chromatin Remodeling Complex during Neural Development. *Neuron* 55, 201-215 (2007).
5. Ho, L. & Crabtree, G. R. Chromatin remodelling during development. *Nature* 463, 474-484 (2010).
6. Narlikar, G. J., Fan, H.-Y. & Kingston, R. E. Cooperation between complexes that regulate chromatin structure and transcription. *Cell* 108, 475-487 (2002).
7. Dykhuizen, E. C. et al. BAF complexes facilitate decatenation of DNA by topoisomerase IIα. *Nature* 497, 624-627 (2013).
8. Kadoch, C. et al. Dynamics of BAF-Polycomb complex opposition on heterochromatin in normal and oncogenic states. *Nat Genet* 49, 213-222 (2017).
9. Miller, E. L. et al. TOP2 synergizes with BAF chromatin remodeling for both resolution and formation of facultative heterochromatin. *Nat Struc & Mol Biol* 33, 1492 (2017).
10. Peng, G. et al. BRIT1/MCPH1 links chromatin remodelling to DNA damage response. *Nat. Cell Biol.* 11, 865-872 (2009).
11. Stanton, B. Z. et al. Smarca4 ATPase mutations disrupt direct eviction of PRC1 from chromatin. *Nat Genet* 49, 282-288 (2017).
12. Hodges, C., Kirkland, J. G. & Crabtree, G. R. The Many Roles of BAF (mSWI/SNF) and PBAF Complexes in Cancer. *Cold Spring Harb Perspect Med* 6, a026930 (2016).
13. Kadoch, C. & Crabtree, G. R. Reversible disruption of mSWI/SNF (BAF) complexes by the SS18—SSX oncogenic fusion in synovial sarcoma. *Cell* 153, 71-85 (2013).
14. Mathur, R. et al. ARID1A loss impairs enhancer-mediated gene regulation and drives colon cancer in mice. *Nat Genet* 49, 296-302 (2017).
15. Deciphering Developmental Disorders Study. Large-scale discovery of novel genetic causes of developmental disorders. *Nature* 519, 223-228 (2015).
16. Dykhuizen, E. C., Carmody, L. C., Tolliday, N., Crabtree, G. R. & Palmer, M. A. J. Screening for Inhibitors of an Essential Chromatin Remodeler in Mouse Embryonic Stem Cells by Monitoring Transcriptional Regulation. *Journal of Biomolecular Screening* 17, 1221-1230 (2012).
17. Wang, X. et al. SMARCB1-mediated SWI/SNF complex function is essential for enhancer regulation. *Nat Genet* 49, 289-295 (2017).
18. Ho, L. et al. An embryonic stem cell chromatin remodeling complex, esBAF, is essential for embryonic stem cell self-renewal and pluripotency. *PNAS* 106, 5181-5186 (2009).
19. Fedorov, O. et al. Selective targeting of the BRG/PB1 bromodomains impairs embryonic and trophoblast stem cell maintenance. *Science Advances* 1, e1500723-e1500723 (2015).
20. Kia, S. K., Gorski, M. M., Giannakopoulos, S. & Verrijzer, C. P. SWI/SNF mediates polycomb eviction and epigenetic reprogramming of the INK4b-ARF-INK4a locus. *Molecular and Cellular Biology* 28, 3457-3464 (2008).
21. Muthuswami, R. et al. Phosphoaminoglycosides inhibit SWI2/SNF2 family DNA-dependent molecular motor domains. *Biochemistry* 39, 4358-4365 (2000).
22. Vangamudi, B. et al. The SMARCA2/4 ATPase Domain Surpasses the Bromodomain as a Drug Target in SWI/SNF-Mutant Cancers: Insights from cDNA Rescue and PFI-3 Inhibitor Studies. *Cancer Research* 75, 3865-3878 (2015).
23. Shiloh, Y. & Ziv, Y. The ATM protein kinase: regulating the cellular response to genotoxic stress, and more. *Nat Rev Mol Cell Biol* 14, 197-210 (2013).
24. Zou, L. & Elledge, S. J. Sensing DNA damage through ATRIP recognition of RPA-ssDNA complexes. *Science* 300, 1542-1548 (2003).
25. Karnitz, L. M. & Zou, L. Molecular Pathways: Targeting ATR in Cancer Therapy. *Clin. Cancer Res.* 21, 4780-4785 (2015).
26. Weber, A. M. & Ryan, A. J. ATM and ATR as therapeutic targets in cancer. *Pharmacology and Therapeutics* 149, 124-138 (2015).
27. Williamson, C. T. et al. ATR inhibitors as a synthetic lethal therapy for tumours deficient in ARID1A. *Nature Communications* 7, 13837 (2016).
28. Ho, L. et al. An embryonic stem cell chromatin remodeling complex, esBAF, is an essential component of the core pluripotency transcriptional network. *PNAS* 106, 5187-5191 (2009).

29. National Center for Biotechnology Information. *PubChem BioAssay Database* doi:AID=602436, https://pubchem.ncbi.nlm.nih.gov/bioassay/602436
30. Tan, D. S. Diversity-oriented synthesis: exploring the intersections between chemistry and biology. *Nature Chemical Biology* 1, 74-84 (2005).
31. Chou, T. C. Drug Combination Studies and Their Synergy Quantification Using the Chou-Talalay Method. *Cancer Research* 70, 440-446 (2010).
32. Chou, T. C. & Talalay, P. Quantitative analysis of dose-effect relationships: the combined effects of multiple drugs or enzyme inhibitors. *Adv. Enzyme Regul.* 22, 27-55 (1984).
33. Brownlee, P. M., Chambers, A. L., Cloney, R., Bianchi, A. & Downs, J. A. BAF180 Promotes Cohesion and Prevents Genome Instability and Aneuploidy. *Cell Rep* 6, 973-981 (2014).
34. Chowdhury, B. et al. PBRM1 Regulates the Expression of Genes Involved in Metabolism and Cell Adhesion in Renal Clear Cell Carcinoma. *PLoS ONE* 11, e0153718 (2016).
35. Jiao, Y. et al. Exome sequencing identifies frequent inactivating mutations in BAP1, ARID1A and PBRM1 in intrahepatic cholangiocarcinomas. *Nat Genet* 45, 1470-1473 (2013).
36. Macher Goeppinger, S. et al. PBRM1 (BAF180) protein is functionally regulated by p53-induced protein degradation in renal cell carcinomas. *The Journal of Pathology* 237, 460-471 (2015).
37. Arai, R. et al. Simultaneous inhibition of Src and Aurora kinases by SU6656 induces therapeutic synergy in human synovial sarcoma growth, invasion and angiogenesis in vivo. *European Journal of Cancer* 48, 2417-2430 (2012).
38. Takebayashi, S.-I. et al. Murine esBAF chromatin remodeling complex subunits BAF250a and Brg1 are necessary to maintain and reprogram pluripotency-specific replication timing of select replication domains. *Epigenetics & Chromatin* 6, 42 (2013).
39. Gao, H. et al. XK469, a selective topoisomerase IIbeta poison. *PNAS* 96, 12168-12173 (1999).
40. Tanabe, K., Ikegami, Y., Ishida, R. & Andoh, T. Inhibition of topoisomerase II by antitumor agents bis(2,6-dioxopiperazine) derivatives. *Cancer Research* 51, 4903-4908 (1991).
41. Yang, F., Kemp, C. J. & Henikoff, S. Doxorubicin Enhances Nucleosome Turnover around Promoters. *Current Biology* 23, 782-787 (2013).
42. Yang, F., Teves, S. S., Kemp, C. J. & Henikoff, S. Doxorubicin, DNA torsion, and chromatin dynamics. *Biochimica et biophysica acta* 1845, 84-89 (2014).
43. Hande, K. R. Etoposide: four decades of development of a topoisomerase II inhibitor. *European Journal of Cancer* (1998). doi:10.1016/S0959-8049(98)00228-7
44. Fillmore, C. M. et al. EZH2 inhibition sensitizes BRG1 and EGFR mutant lung tumours to TopoII inhibitors. *Nature* 520, 239-242 (2015).
45. Pang, B., de Jong, J., Qiao, X., Wessels, L. F. A. & Neefjes, J. Chemical profiling of the genome with anticancer drugs defines target specificities. *Nature Chemical Biology* 11, 472-480 (2015).
46. Marcaurelle, L. A. et al. An Aldol-Based Build/Couple/Pair Strategy for the Synthesis of Medium- and Large-Sized Rings: Discovery of Macrocyclic Histone Deacetylase Inhibitors. *J. Am. Chem. Soc.* 132, 16962-16976 (2010).
47. Meisenberg, C. & Downs, J. A. The SWI/SNF chromatin remodelling complex: Its role in maintaining genome stability and preventing tumourigenesis. *DNA Repair* 32, 127-133 (2015).
48. Fitzgerald, M. E. et al. Build/Couple/Pair Strategy for the Synthesis of Stereochemically Diverse Macrolactams via Head-to-Tail Cyclization. *ACS Comb. Sci.* 14, 89-96 (2012).
49. Tiscornia, G., Singer, O. & Verma, I. M. Production and purification of lentiviral vectors. *Nat Protoc* 1, 241-245 (2006).
50. Raab, J. R., Resnick, S. & Magnuson, T. Genome-Wide Transcriptional Regulation Mediated by Biochemically Distinct SWI/SNF Complexes. *PLoS Genet.* 11, e1005748 (2015).
51. Schmittgen, T. D. & Livak, K. J. Analyzing real-time PCR data by the comparative CT method. *Nat Protoc* 3, 1101-1108 (2008).

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the embodiments shown and described herein. Rather, the scope and spirit of present invention is embodied by the appended embodiments.

What is claimed is:

1. A method of modulating a BAF complex in a cell, the method comprising:
contacting a cell comprising a BAF complex with a BAF complex modulating compound to modulate the activity of a BAF complex in the cell, wherein the BAF complex modulating compound is a compound of formula (IA):

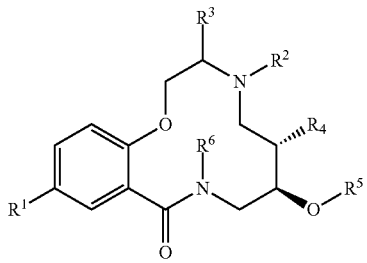

(IA)

wherein:
R$^1$ is amine, substituted amine, alkylaminocarbonylamino, substituted alkylaminocarbonylamino, alkanoylamino, substituted alkanoylamino, arylaminocarbonylamino, substituted arylaminocarbonlamino, carbamate, substituted carbamate, aroylamino or substituted aroylamino;
R$^2$ is heteroaryl-aryl-alkyl, substituted heteroaryl-aryl-alkyl, aryl-heteroaryl-alkyl, substituted aryl-heteroaryl alkyl, alkanoyl or substituted alkanoyl; and
R$^3$ to R$^6$ are each independently H, alkyl or substituted alkyl;
or a pharmaceutically acceptable salt thereof.

2. The method of claim 1, wherein the cell is in vitro.

3. A method of treating cancer, the method comprising:
co-administering to a subject with cancer:
a therapeutically effective amount of a pharmaceutical composition comprising BAF complex modulating compound of formula (IA):

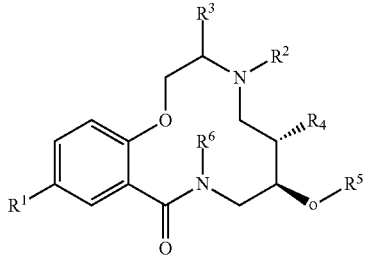

(IA)

wherein:
R$^1$ is amine, substituted amine, alkylaminocarbonylamino, substituted alkylaminocarbonylamino, alkanoylamino, substituted alkanoylamino, arylaminocarbonylamino, substituted arylaminocarbonlamino, carbamate, substituted carbamate, aroylamino or substituted aroylamino;
R$^2$ is heteroaryl-aryl-alkyl, substituted heteroaryl-aryl-alkyl, aryl-heteroaryl-alkyl, substituted aryl-heteroaryl alkyl, alkanoyl or substituted alkanoyl; and
R$^3$ to R$^6$ are each independently H, alkyl or substituted alkyl;
or a pharmaceutically acceptable salt thereof; and
an ATR inhibitor;
to treat the subject for cancer.

4. The method of claim 3, wherein the subject has cancer cells having a ARID1A-containing BAF complex and administration of the BAF complex modulating compound sensitizes the cancer cells to inhibition of ATR kinase.

5. The method of claim 4, wherein the pharmaceutical composition and the ATR inhibitor act synergistically to kill cancer cells of the subject.

6. The method of claim 5, wherein the synergistic action provides a reduction in the effective dose of the ATR inhibitor to an amount below a threshold of toxicity.

7. The method of claim 3, wherein the subject has cancer cells harboring a BAF complex mutation.

8. A method of treating a BRCA1 cancer, the method comprising:
administering to a subject with a BRCA1 cancer a therapeutically effective amount of a pharmaceutical composition comprising BAF complex modulating compound of formula (IA):

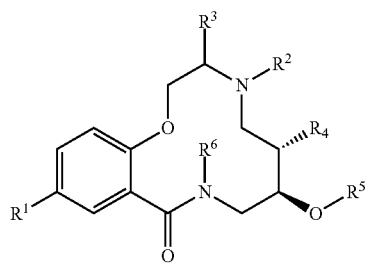

(IA)

wherein:
R$^1$ is amine, substituted amine, alkylaminocarbonylamino, substituted alkylaminocarbonylamino, alkanoylamino, substituted alkanoylamino, arylaminocarbonylamino, substituted arylaminocarbonlamino, carbamate, substituted carbamate, aroylamino or substituted aroylamino;
R$^2$ is heteroaryl-aryl-alkyl, substituted heteroaryl-aryl-alkyl, aryl-heteroaryl-alkyl, substituted aryl-heteroaryl alkyl, alkanoyl or substituted alkanoyl; and
R$^3$ to R$^6$ are each independently H, alkyl or substituted alkyl;
or a pharmaceutically acceptable salt thereof;
to treat the BRCA1 cancer.

9. The method of claim 8, wherein the cancer is Breast Cancer, Prostate Cancer, Pancreatic Cancer, Lung Cancer, Colon Cancer, Ovarian Cancer, Liver Cancer, Melanoma, Renal Cancer, Central Nervous System Cancer or Leukemia Lymphoma.

* * * * *

SEQUENCE LISTING

<160> NUMBER OF SEQ ID NOS: 12

<210> SEQ ID NO 1
<211> LENGTH: 25
<212> TYPE: DNA
<213> ORGANISM: Artificial Sequence
<220> FEATURE:
<223> OTHER INFORMATION: Synthetic sequence

<400> SEQUENCE: 1
acctctatcg cctctatgtg tctgt                                              25

<210> SEQ ID NO 2
<211> LENGTH: 20
<212> TYPE: DNA
<213> ORGANISM: Artificial Sequence
<220> FEATURE:
<223> OTHER INFORMATION: Synthetic sequence

<400> SEQUENCE: 2
ctggcagcac tgcttgatgt                                                    20

<210> SEQ ID NO 3
<211> LENGTH: 21
<212> TYPE: DNA
<213> ORGANISM: Artificial Sequence
<220> FEATURE:
<223> OTHER INFORMATION: Synthetic sequence

<400> SEQUENCE: 3
gcaaggtgtg agtggttact g                                                  21

<210> SEQ ID NO 4
<211> LENGTH: 20
<212> TYPE: DNA
<213> ORGANISM: Artificial Sequence
<220> FEATURE:
<223> OTHER INFORMATION: Synthetic sequence

<400> SEQUENCE: 4
ggactgggac ggcagatact                                                    20

<210> SEQ ID NO 5
<211> LENGTH: 21
<212> TYPE: DNA
<213> ORGANISM: Artificial Sequence
<220> FEATURE:
<223> OTHER INFORMATION: Synthetic sequence

<400> SEQUENCE: 5
caagtgcagg gccagcctaa c                                                  21

<210> SEQ ID NO 6
<211> LENGTH: 23
<212> TYPE: DNA
<213> ORGANISM: Artificial Sequence
<220> FEATURE:
<223> OTHER INFORMATION: Synthetic sequence

<400> SEQUENCE: 6
aacctgtgag ggtgtctgaa acc                                                23

<210> SEQ ID NO 7
<211> LENGTH: 24
<212> TYPE: DNA
<213> ORGANISM: Artificial Sequence

```
<220> FEATURE:
<223> OTHER INFORMATION: Synthetic sequence

<400> SEQUENCE: 7
gaatgtgaca gtgaagaaga cagc                                          24

<210> SEQ ID NO 8
<211> LENGTH: 25
<212> TYPE: DNA
<213> ORGANISM: Artificial Sequence
<220> FEATURE:
<223> OTHER INFORMATION: Synthetic sequence

<400> SEQUENCE: 8
agacaccaga attcaaagct ggatc                                         25

<210> SEQ ID NO 9
<211> LENGTH: 27
<212> TYPE: DNA
<213> ORGANISM: Artificial Sequence
<220> FEATURE:
<223> OTHER INFORMATION: Synthetic sequence

<400> SEQUENCE: 9
cggattcaga atttggcatt ccaaaga                                       27

<210> SEQ ID NO 10
<211> LENGTH: 26
<212> TYPE: DNA
<213> ORGANISM: Artificial Sequence
<220> FEATURE:
<223> OTHER INFORMATION: Synthetic sequence

<400> SEQUENCE: 10
gcttgttgtt ttggatgttt tcctgc                                        26

<210> SEQ ID NO 11
<211> LENGTH: 16
<212> TYPE: DNA
<213> ORGANISM: Artificial Sequence
<220> FEATURE:
<223> OTHER INFORMATION: Synthetic sequence

<400> SEQUENCE: 11
gccagccgag ccacat                                                   16

<210> SEQ ID NO 12
<211> LENGTH: 24
<212> TYPE: DNA
<213> ORGANISM: Artificial Sequence
<220> FEATURE:
<223> OTHER INFORMATION: Synthetic sequence

<400> SEQUENCE: 12
ctttaccaga gttaaaagca gccc                                          24
```